United States Patent
Wang et al.

(10) Patent No.: US 9,669,095 B2
(45) Date of Patent: Jun. 6, 2017

(54) CYCLOSPORIN ANALOGUES FOR PREVENTING OR TREATING HEPATITIS C INFECTION

(71) Applicant: Enanta Pharmaceuticals, Inc., Watertown, MA (US)

(72) Inventors: Guoqiang Wang, Belmont, MA (US); In Jong Kim, Lexington, MA (US); Yat Sun Or, Watertown, MA (US)

(73) Assignee: ENANTA PHARMACEUTICALS, INC., Watertown, MA (US)

( * ) Notice: Subject to any disclaimer, the term of this patent is extended or adjusted under 35 U.S.C. 154(b) by 0 days.

(21) Appl. No.: 14/931,384

(22) Filed: Nov. 3, 2015

(65) Prior Publication Data

US 2016/0130304 A1 May 12, 2016

Related U.S. Application Data

(60) Provisional application No. 62/074,165, filed on Nov. 3, 2014.

(51) Int. Cl.

| A61K 38/13 | (2006.01) |
|---|---|
| C07K 7/64 | (2006.01) |
| A61K 45/06 | (2006.01) |
| A61K 38/21 | (2006.01) |
| A61K 31/7056 | (2006.01) |

(52) U.S. Cl.
CPC .......... *A61K 45/06* (2013.01); *A61K 31/7056* (2013.01); *A61K 38/13* (2013.01); *A61K 38/21* (2013.01); *C07K 7/645* (2013.01)

(58) Field of Classification Search
CPC ................. A61K 38/13; C07K 7/645
See application file for complete search history.

(56) References Cited

U.S. PATENT DOCUMENTS

| 4,108,985 A | 8/1978 | Ruegger et al. |
|---|---|---|
| 4,220,641 A | 9/1980 | Traber et al. |
| 4,288,431 A | 9/1981 | Traber et al. |
| 4,384,996 A | 5/1983 | Bollinger et al. |
| 4,396,542 A | 8/1983 | Wenger |
| 4,554,351 A | 11/1985 | Wenger |
| 4,771,122 A | 9/1988 | Seebach |
| 4,798,823 A | 1/1989 | Witzel |
| 5,239,057 A | 8/1993 | Wang et al. |
| 5,284,826 A | 2/1994 | Eberle |
| 5,525,590 A | 6/1996 | Bollinger et al. |
| 5,604,092 A | 2/1997 | Erlanger et al. |
| 6,784,156 B2 | 8/2004 | Or et al. |
| 6,809,077 B2 | 10/2004 | Or et al. |
| 6,927,208 B1 | 8/2005 | Wenger et al. |
| 6,979,671 B2 | 12/2005 | Or et al. |
| 7,012,064 B2 | 3/2006 | Or et al. |
| 7,012,065 B2 | 3/2006 | Or et al. |
| 7,438,920 B1 | 10/2008 | Kim et al. |
| 7,468,419 B2 | 12/2008 | Wu et al. |
| 8,178,531 B2 | 5/2012 | Or et al. |
| 8,349,312 B2 | 1/2013 | Wang et al. |
| 8,367,053 B2 | 2/2013 | Long et al. |
| 8,367,618 B2 | 2/2013 | Or et al. |
| 8,481,483 B2 | 7/2013 | Or et al. |
| 8,623,814 B2 | 1/2014 | Or et al. |
| 8,685,917 B2 | 4/2014 | Gao et al. |
| 8,906,853 B2 | 12/2014 | Or et al. |
| 9,221,878 B2 | 12/2015 | Or et al. |
| 2002/0142946 A1 | 10/2002 | Or et al. |
| 2003/0087813 A1 | 5/2003 | Or et al. |
| 2003/0104992 A1 | 6/2003 | Or et al. |
| 2006/0069015 A1 | 3/2006 | Molino et al. |
| 2007/0213301 A1 | 9/2007 | Zhang et al. |
| 2007/0249527 A1 | 10/2007 | Wu et al. |
| 2008/0214447 A1 | 9/2008 | Kobayashi et al. |
| 2010/0196316 A1 | 8/2010 | Or et al. |
| 2010/0209390 A1 | 8/2010 | Or et al. |
| 2011/0008284 A1 | 1/2011 | Gao et al. |
| 2011/0008285 A1 | 1/2011 | Long et al. |
| 2011/0008286 A1 | 1/2011 | Wang et al. |
| 2011/0206637 A1 | 8/2011 | Or et al. |
| 2011/0218175 A1 | 9/2011 | Or et al. |
| 2012/0264679 A1 | 10/2012 | Fliri et al. |
| 2013/0183267 A1 | 7/2013 | Or et al. |

FOREIGN PATENT DOCUMENTS

| EP | 0034567 A2 | 8/1981 |
|---|---|---|
| EP | 0056782 A1 | 7/1982 |
| EP | 0300784 A2 | 1/1989 |
| EP | 0300785 A2 | 1/1989 |
| GB | 2206119 A | 12/1988 |
| GB | 2207678 A | 2/1989 |

(Continued)

OTHER PUBLICATIONS

Wilson, et al., "RNA interference blocks gene expression and RNA synthesis from hepatitis C replicons propagated in human liver cells," PNAS, 100(5):2783-2788, 2003.

Nakagawa, et al., "Suppression of Hepatitis C Virus Replication by Cyclosporin A Is Mediated by Blockade of Cyclophilins", Gastroenterology, Elsevier, Philadelphia, PA,129(3):1031-1041, 2005.

Freidinger, R.M., et al., "Synthesis of 9-Fluorenylmethyloxycarbonyl-Protected N-Alkyl Amino Acids by Reduction of Oxazolidinones", J. Org. Chem., 48:77-81, 1983.

Paeshuyse et al. "The Non-Immunosuppressive Cyclosporin DEBIO-025 Is a Potent Inhibitor of Hepatitis C Virus Replication In Vitro", Hepatology, pp. 761-770, 2006.

(Continued)

*Primary Examiner* — Jeffrey E Russel
(74) *Attorney, Agent, or Firm* — Edgar W. Harlan; Carolyn S. Elmore; Elmore Patent Law Group, P.C.

(57) ABSTRACT

The present invention relates to novel cyclosporine analogs having antiviral activity against HCV and useful in the treatment of HCV infections. More particularly, the invention relates to novel cyclosporine analog compounds, compositions containing such compounds and methods for using the same, as well as processes for making such compounds.

12 Claims, No Drawings

(56) References Cited

FOREIGN PATENT DOCUMENTS

| WO | 8602080 | A1 | 4/1986 |
|---|---|---|---|
| WO | 9918120 | A1 | 4/1999 |
| WO | 03033526 | A2 | 4/2003 |
| WO | 2004099241 | A1 | 11/2004 |
| WO | 2005021028 | A1 | 3/2005 |
| WO | 2006005610 | A1 | 1/2006 |
| WO | 2006038088 | A1 | 4/2006 |
| WO | 2006039668 | A2 | 4/2006 |
| WO | 2007041631 | A1 | 4/2007 |
| WO | 2007049803 | A1 | 5/2007 |
| WO | 2007112345 | A2 | 10/2007 |
| WO | 2007112352 | A2 | 10/2007 |
| WO | 2007112357 | A2 | 10/2007 |
| WO | 2008139986 | A1 | 11/2008 |
| WO | 2012009715 | A2 | 1/2012 |
| WO | 2012021796 | A2 | 2/2012 |

OTHER PUBLICATIONS

Kobel, et al., "Directed Biosynthesis of Cyclosporins," Europ. J. Applied Microbiology and Biotechnology, 14:273-240 1982.

Von Wartburg, et al., "Chemistry of the Natural Cyclosporin Metabolites", Progress in Allergy, 38:28-45, 1986.

Wenger, R., "Synthesis of Cyclosporine and Analogues: Structure, Activity, Relationships of New Cycloporine Derivatives", Transpl. Proc., XV(4):Suppl. 1, pp. 2230-2241, 1983.

Wenger, "Cyclosporine and Analogues—Isolation and Synthesis—Mechanism of Action and Structural Requirements for Pharmacological Activity," Progress in the Chemistry of Organic Natural Products, 50:123-168, 1986.

Watashi et al., "Cyclosporin A Suppresses Replication of Hepatitis C Virus Genome in Cultured Hepatocytes," Hepatology, 38(5):1282-1288, 2003.

Nakagawa et al., "Specific Inhibition of Hepatitis C Virus Replication by Cyclosporin A", Biochem. Biophys. Res. Commun., 313:42-47, 2004.

Shimotohno, et al., "Inhibitory Role of Cyclosporin A and Its Derivatives on Replication of Hepatitis C Virus", American Transplant Congress, Abstract No. 648 (American Journal of Transplantation, 4(s8):334-335, 2004.

Inoue, et al., "Combined Interferon α2b and Cyclosporin A in the Treatment of Chronic Hepatitis C: Controlled Trial", Journal of Gastroenterology, 38:567-572, 2003.

Papageorgiou, C., et al., "Improved Binding Affinity for Cyclophilin A by a Cyclosporin Derivative Singly Modified at Its Effector Domain", J. Med. Chem. 37:3674-3676, 1994.

Paeshuyse, et al., "Potent and Selective Inhibition of Hepatitis C Virus Replication by the Non-Immunosuppressive Cyclosporin Analogue DEBIO-025," Antiviral Research 65(3):A41, 2005.

Flisiak, R., et al., "The Cyclophilin Inhibitor Debio-025 Shows Potent Anti-Hepatitis C Effect in Patients Coinfected with Hepatitis C and Human Immunodeficiency Virus", Hepatology, 47(3):817-826, 2008.

Ma, S., et al., "NIM811, a Cyclophilin Inhibitor, Exhibits Potent In Vitro Activity against Hepatitis C Virus Alone or in Combination with Alpha Interferon", Antimicrobial Agents and Chemotherapy, 50(9):2976-2982, 2006.

Robida, J.M., et al., "Characterization of Hepatitis C Virus Subgenomic Replicon Resistance to Cyclosporine in Vitro", Journal of Virology, 81(11):5829-5840, 2007.

Flisiak, R., et al., "Cyclophilin Inhibitors in Hepatitis C Viral Infection", Expert Opin. Investig. Drugs, 16(9):1345-1354, 2007.

Papageorgiou, C., et al., "Calcineurin Has a Very Tight-Binding Pocket for the Side Chain of Residue 4 of Cyclosporin", Bioorganic & Medicinal Chemistry Letters, 4(2):267-272, 1994.

CYCLOSPORIN ANALOGUES FOR PREVENTING OR TREATING HEPATITIS C INFECTION

RELATED APPLICATION

This application claims the benefit of U.S. Provisional Application No. 62/074,165, filed on Nov. 3, 2014. The entire teachings of the above application is incorporated herein by reference.

TECHNICAL FIELD

The present invention relates to novel cyclosporine analogues having antiviral activity against HCV and useful in the treatment of HCV infections. More particularly, the invention relates to novel cyclosporine analogue compounds, compositions containing such compounds and methods for using the same, as well as processes for making such compounds.

BACKGROUND OF THE INVENTION

Infection with HCV is a major cause of human liver disease throughout the world. In the US, an estimated 4.5 million Americans are chronically infected with HCV. Although only 30% of acute infections are symptomatic, greater than 85% of infected individuals develop chronic, persistent infection. Treatment costs for HCV infection have been estimated at $5.46 billion for the US in 1997. Worldwide over 200 million people are estimated to be infected chronically. HCV infection is responsible for 40-60% of all chronic liver disease and 30% of all liver transplants. Chronic HCV infection accounts for 30% of all cirrhosis, end-stage liver disease, and liver cancer in the U.S. The CDC estimates that the number of deaths due to HCV will minimally increase to 38,000/year by the year 2010.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Due to the high degree of variability in the viral surface antigens, existence of multiple viral genotypes, and demonstrated specificity of immunity, the development of a successful vaccine in the near future is unlikely. Only two approved therapies for HCV infection are currently available. The original treatment regimen generally involves a 3-12 month course of intravenous interferon-α (IFN-α), while a new approved second-generation treatment involves co-treatment with IFN-α and the general antiviral nucleoside mimics like ribavirin. Both of these treatments suffer from interferon related side effects as well as low efficacy against HCV infections. There exists a need for the development of effective antiviral agents for treatment of HCV infection due to the poor tolerability and disappointing efficacy of existing therapies.

Cyclosporin A (CsA), a neutral cyclic undecapeptide isolated from the fungus *Tolypocladium injlaturn* and currently marketed as Neoral and sandimmunem (Novartis, Basel, Switzerland), has been widely used for the prevention of organ transplant rejection. The molecular basis for the immunosuppressant activity of cyclosporin A and cyclosporin analogues begins with the passive diffusion of the cyclosporin (Cs) molecule into the cell, followed by binding to its intracellular receptor, cyclophilin A (CypA). CypA belongs to a family of proteins that catalyze cis-trans peptidyl-prolyl isomerization, i.e., PPIase, a rate-limiting step in protein folding. CsA and other cyclosporin analogues bind to the active site of CypA. However, immunosuppression is not believed to be due to the inhibition of CypA PPIase activity. The target of the CsA-CypA complex is a $Ca^{2+}$-calmodulin-dependent serine-threonine-specific protein phosphatase, calcineurin. In T-cells responding to antigen presentation, an increase in intracellular $Ca^{2+}$ activates calcineurin, which subsequently dephosphorylates the transcription factor called the nuclear factor of activated T-cells ("NFAT"). Dephosphorylated NFAT undergoes a molecular change, e.g., homodimerization that allows it to cross into the nucleus, and promotes the expression of T-cell activation genes. CsA and other immunosuppressive cyclosporin derivatives inhibit calcineurin which results in the inhibition of expression of cytokine genes, e.g., interleukin-2 (IL-2) that promotes T-cell activation and proliferation, i.e., immunosuppressive activity.

Cyclosporine A and certain derivatives have been reported as having anti-HCV activity, see Watashi et al., Hepatology, 2003, Volume 38, pp 1282-1288, Nakagawa et al., Biochem. Biophys. Res. Commun. 2004, Volume 3 13, pp 42-7, and Shimotohno and K. Watashi, 2004 American Transplant Congress, Abstract No. 648 (American Journal of Transplantation 2004, Volume 4, Issue s8, Pages 1-653). The authors of the Nakagawa et al. paper state that certain chaperone activities, such as those of cyclophilins, may be crucial for the processing and maturation of the viralproteins and for viral replication. Cyclosporine derivatives having HCV activity are known from International Publication No's. WO 2005/021028, WO 2006/039668, WO 2006/038088, WO 2006/039688, WO 2007/112352, WO 2007/112357, WO 2007/112345 and WO 2007/041631.

A subsequent controlled clinical trial showed that a combination of cyclosporin A with interferon α2b is more effective than interferon monotherapy, especially in patients with high viral loads (Inoue et al., "Combined Interferon α2b nd Cyclosporin A in the Treatment of Chronic Hepatitis C: Controlled Trial," *J. Gastroenterol.* 38:567-572 (2003)).

PCT International Patent Publication No. WO 2006/005610 recently described the use of a combination of cyclosporin A and pegylated interferon for treating hepatitis C viral infection. In addition, PCT International Patent Publication No. WO 2005/021028 relates to the use of non-immunosuppressive cyclosporine for treatment of HCV disorders. Also, Paeshuyse et al., "Potent and Selective Inhibition of Hepatitis C Virus Replication by the Non-Immunosuppressive Cyclosporin Analogue DEBIO-025," *Antiviral Research* 65(3):A41 (2005) recently published results for a non-immunosuppressive cyclosporin analogue, DEBIO-025, that exhibited potent and selective inhibition of hepatitis C virus replication. Debio-025 does possess potent binding affinity for cyclophilin A.

SUMMARY OF THE INVENTION

The present invention relates to novel Cyclosporin analogues represented herein below, pharmaceutical compositions comprising such compounds, and methods for the treatment of viral (particularly hepatitis C viral) infection in a subject in need of such therapy with said compounds.

In its principal embodiment, the present invention provides a compound of Formula (I), or a pharmaceutically acceptable salt thereof;

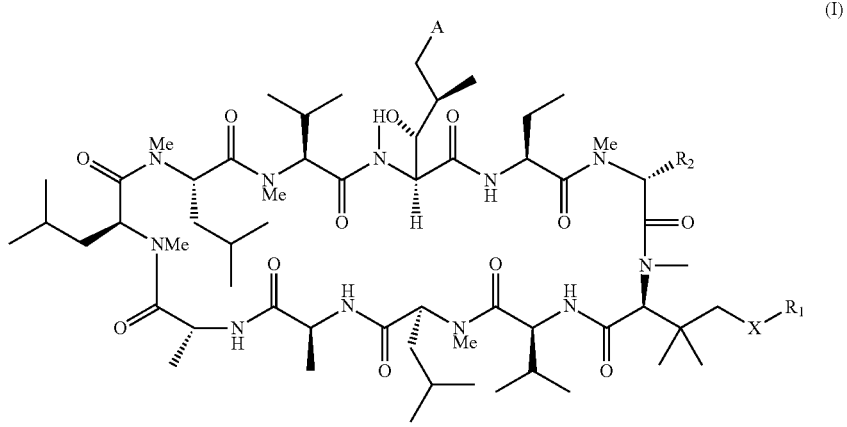

(I)

$R_1$ and A are each independently selected from:
a) $R_{11}$, where $R_{11}$ is selected from:
1) Hydrogen;
2) Deuterium;
3) $C_1$-$C_8$ alkyl;
4) Substituted $C_1$-$C_8$ alkyl;
5) $C_2$-$C_8$ alkenyl;
6) Substituted $C_2$-$C_8$ alkenyl;
7) $C_2$-$C_8$ alkynyl;
8) Substituted $C_2$-$C_8$ alkynyl;
9) $C_3$-$C_{12}$ cycloalkyl;
10) Substituted $C_3$-$C_{12}$ cycloalkyl;
11) Aryl;
12) Substituted aryl;
13) Heterocycloalkyl;
14) Substituted heterocycloalkyl;
15) Heteroaryl; and
16) Substituted heteroaryl;
b) —C(O)O$R_{11}$, wherein $R_{11}$ is as previously defined;
c) —C(O)$R_{11}$, wherein $R_{11}$ is as previously defined;
d) —C(O)OCH$_2$-T-$R_{12}$, wherein T is —O— or —S— and $R_{12}$ is selected from:
1) $C_1$-$C_8$ alkyl;
2) Substituted $C_1$-$C_8$ alkyl;
3) $C_2$-$C_8$ alkenyl;
4) Substituted $C_2$-$C_8$ alkenyl;
5) $C_2$-$C_8$ alkynyl;
6) Substituted $C_2$-$C_8$ alkynyl;
7) $C_3$-$C_{12}$ cycloalkyl;
8) Substituted $C_3$-$C_{12}$ cycloalkyl;
9) Aryl;
10) Substituted aryl;
11) Heterocycloalkyl;
12) Substituted heterocycloalkyl;
13) Heteroaryl; or
14) Substituted heteroaryl;
e) —C(O)N($R_{13}$)($R_{14}$), wherein $R_{13}$ and $R_{14}$ are independently selected from $R_{11}$ and $R_{11}$ is as previously defined or $R_{13}$ and $R_{14}$, together with the nitrogen atom to which they are attached, form a substituted or unsubstituted heterocycloalkyl;
f) —C(O)S$R_{11}$, wherein $R_{11}$ is as previously defined;
g) —C(S)O$R_{11}$, wherein $R_{11}$ is as previously defined;
h) —C(O)OCH$_2$OC(O)$R_{12}$, wherein $R_{12}$ is as previously defined;
i) —C(S)S$R_{11}$, wherein $R_{11}$ is as previously defined;

X is or selected from the group of consisting of: O, S(O)$_m$, wherein m is 0, 1, or 2, and N($R_{12}$), wherein $R_{12}$ is $R_{11}$, and $R_{11}$ is as previously defined or $R_{12}$ and $R_1$ are taken together with the nitrogen atom to which they are attached to form a substituted or unsubstituted heterocycloalkyl; and $R_2$ is selected from hydrogen and methyl. In a preferred embodiment, $R_2$ is methyl.

In another embodiment, the present invention provides a pharmaceutical composition comprising a therapeutically effective amount of a compound or combination of compounds of the present invention, or a pharmaceutically acceptable salt form, prodrug, salt of a prodrug, stereoisomer, tautomer, solvate, or combination thereof, in combination with a pharmaceutically acceptable carrier or excipient.

In yet another embodiment, the present invention provides a method of inhibiting the replication of an RNA-containing virus comprising contacting said virus with a therapeutically effective amount of a compound or a combination of compounds of the present invention, or a pharmaceutically acceptable salt, prodrug, salt of a pro drug, stereoisomer, tautomer, solvate, or combination thereof. Particularly, this invention is directed to methods of inhibiting the replication of hepatitis C virus.

In still another embodiment, the present invention provides a method of treating or preventing infection caused by an RNA-containing virus comprising administering to a patient in need of such treatment a therapeutically effective amount of a compound or combination of compounds of the present invention, or a pharmaceutically acceptable salt form, prodrug, salt of a prodrug, stereoisomer, or tautomer, solvate, or combination thereof. Particularly, this invention is directed to methods of treating or preventing infection caused by hepatitis C virus.

Yet another embodiment of the present invention provides the use of a compound or combination of compounds of the present invention, or a therapeutically acceptable salt form, prodrug, salt of a prodrug, stereoisomer or tautomer, solvate, or combination thereof, as defined hereinafter, in the preparation of a medicament for the treatment or prevention of infection caused by RNA-containing virus, specifically hepatitis C virus (HCV).

DETAILED DESCRIPTION OF THE INVENTION

In a first embodiment of the present invention is a compound of Formula (I) as illustrated above, or a pharmaceutically acceptable salt, ester or prodrug thereof.

In one embodiment, compounds of the invention are represented by Formula (II):

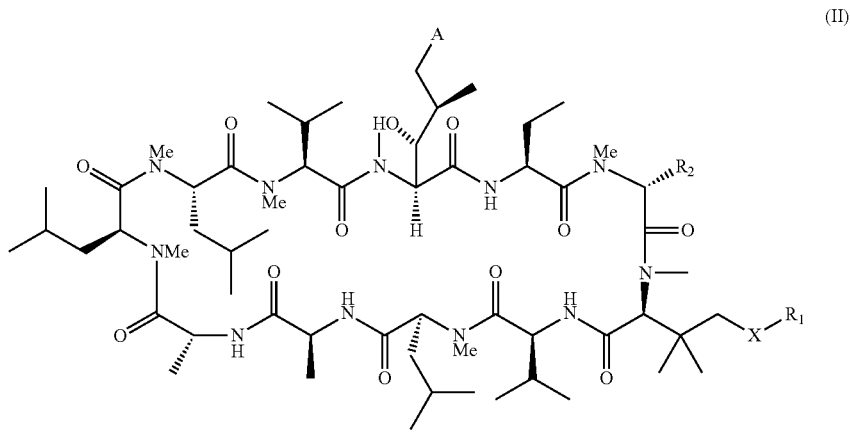

(II)

wherein $R_1$, X and A are as defined in Formula (I).

In one embodiment, compounds of the invention are represented by Formula (III):

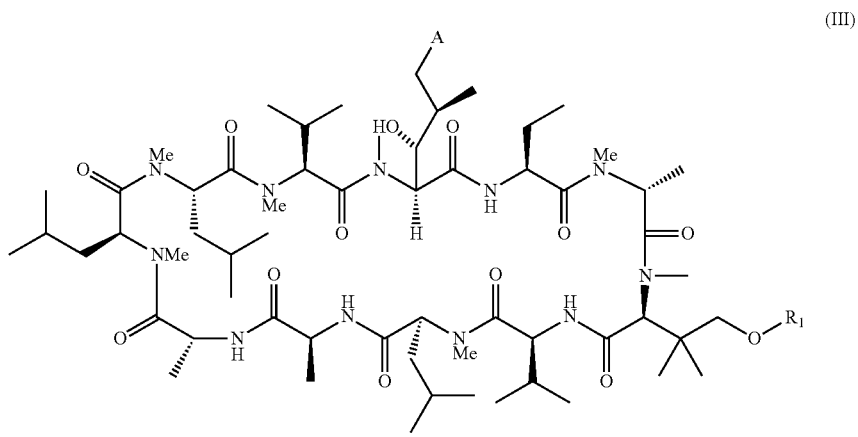

(III)

wherein $R_1$ and A are as defined in Formula (I).

In one embodiment, compounds of the invention are represented by Formula (IV):

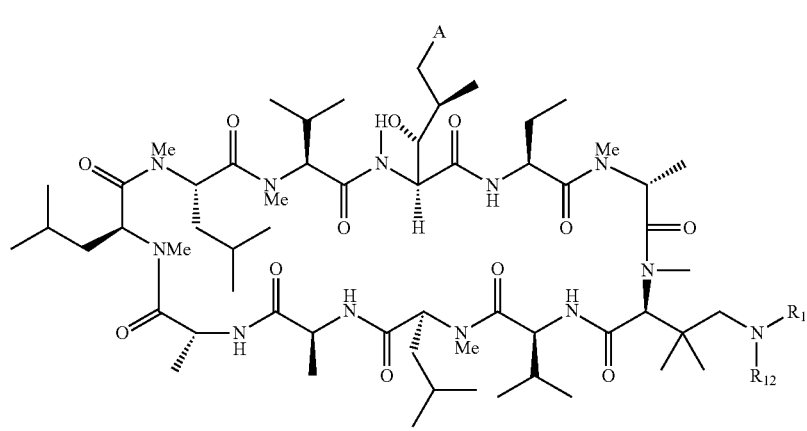

(IV)

wherein $R_1$, $R_{12}$ and A are defined in Formula (I).

In certain embodiments of the compounds of Formulas (I)-(IV), A is W—$C_1$-$C_6$-alkyl- or W—$C_2$-$C_6$-alkenyl-. In another embodiment of the compounds of Formulas (I)-(IV), A is W—$C_1$-$C_4$-alkyl- or W—$C_2$-$C_4$-alkenyl-. W is hydrogen, hydroxyl, heterocyclyl, heteroaryl, heteroaryl-S, heteroaryl-O, heteroaryl-NH—, heterocyclyl-C(O)O—, —OC(O)N($R_{13}$)($R_{14}$), or —C(O)N($R_{13}$)($R_{14}$).

In certain embodiments, A in Formulas (I)-(IV) is selected from the groups

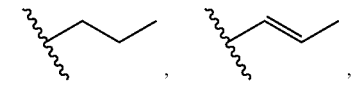

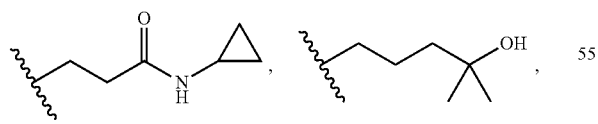

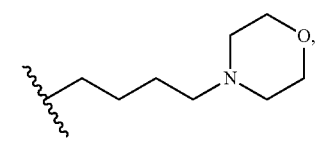

-continued

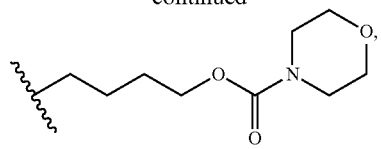

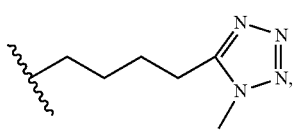

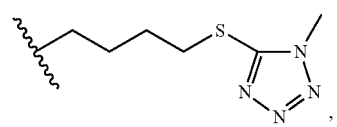

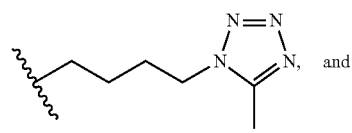 and

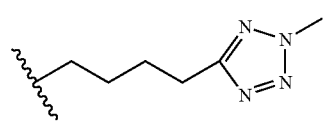

In one embodiment, compounds of the invention are represented by Formula (V),

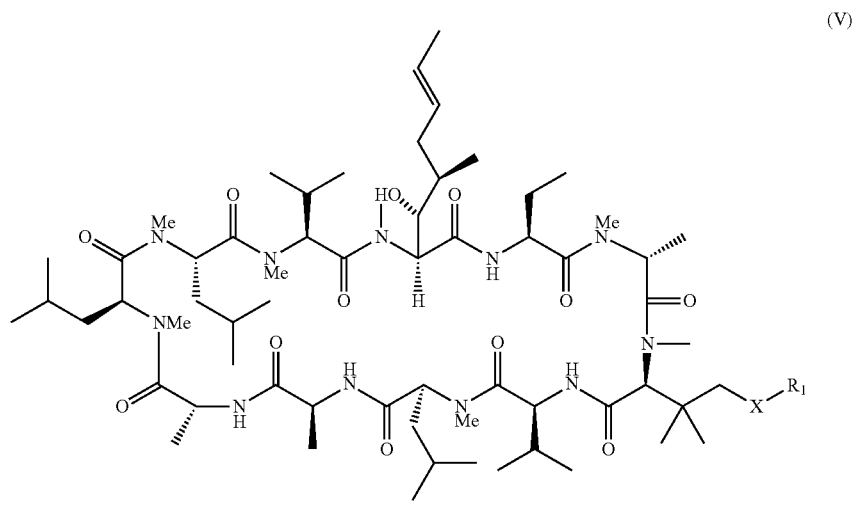

(V)

wherein X and $R_1$ are defined in Formula (I).

In certain embodiments of the compounds of Formulas (I)-(V), $R_1$ is selected from the group consisting of:

1) Hydrogen;
2) Deuterium;
3) —C(O)O$R_{11}$, wherein $R_{11}$ is as previously defined;
4) —C(O) $R_{11}$, wherein $R_{11}$ is as previously defined;
5) —C(O)N($R_{13}$)($R_{14}$), wherein $R_{13}$ and $R_{14}$ are independently selected from $R_{11}$ and $R_{11}$ is as previously defined; or $R_{13}$ and $R_{14}$ are taken together with the nitrogen atom to which they are attached to form a substituted or unsubstituted heterocycloalkyl;
6) —C(O)S$R_{11}$, wherein $R_{11}$ is as previously defined;
7) —C(S)O$R_{11}$, wherein $R_{11}$ is as previously defined;
8) —C(O)OCH$_2$OC(O) $R_{12}$, wherein $R_{12}$ is as previously defined;
9) —C(S)S $R_{11}$, wherein $R_{11}$ is as previously defined.

In certain embodiments of the compounds of Formulas (I), (II) and (V), X is N($R_{12}$), wherein $R_{12}$ is hydrogen, —C(O)OR', substituted or unsubstituted $C_1$-$C_4$-alkyl or phenyl, or $R_{12}$ and $R_1$ are taken together with the nitrogen atom to which they are attached to form a substituted or unsubstituted heterocyclyl or heteroaryl group; preferably $R_{12}$ is hydrogen or methyl.

In certain embodiments of the compounds of Formulas (I), (II) and (V), X is N($R_{12}$) and $R_1$ is —C(O)CH(R)NHC(O)OR', wherein R is hydrogen, $C_1$-$C_6$-alkyl optionally substituted with aryl or heteroaryl, —C(O)OR', phenyl, substituted phenyl; preferably R is $C_1$-$C_4$-alkyl. R' is $C_1$-$C_4$-alkyl, preferably R' is methyl or ethyl.

In certain embodiments of the compounds of Formulas (I), (II) and (V), X is O, and $R_1$ is —C(O)R'', where R'' is phenyl, heteroaryl, or $C_1$-$C_6$-alkyl; or $R_1$ is —C(O)N($R_{13}$)($R_{14}$) and $R_{13}$ and $R_{14}$ are previously defined.

In certain embodiments, the invention relates to compounds of Formulas (I), (II) and (V) wherein X—$R_1$ is selected from the groups set forth below:

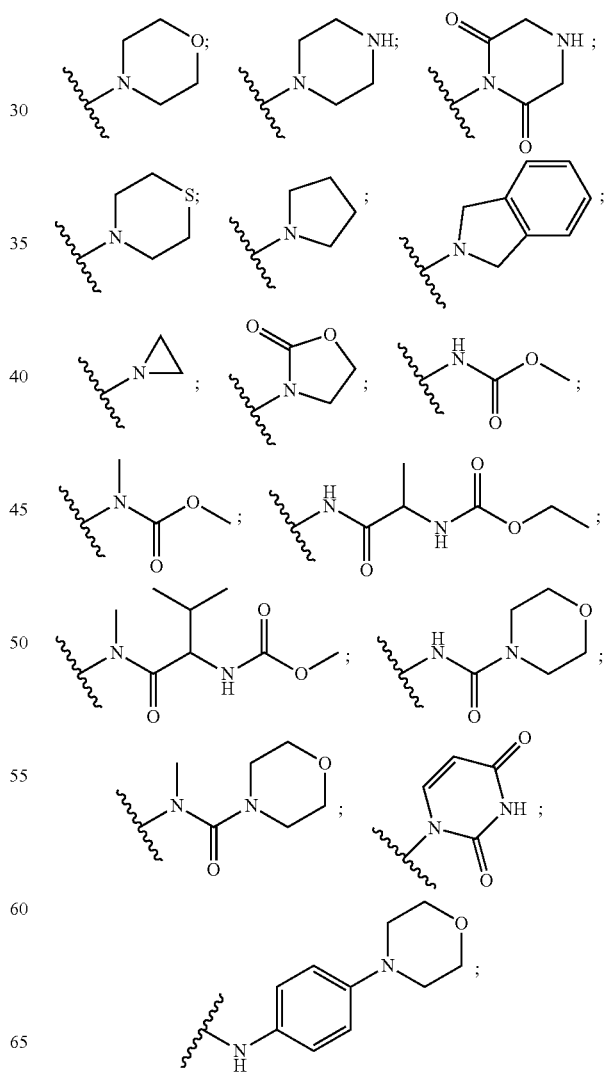

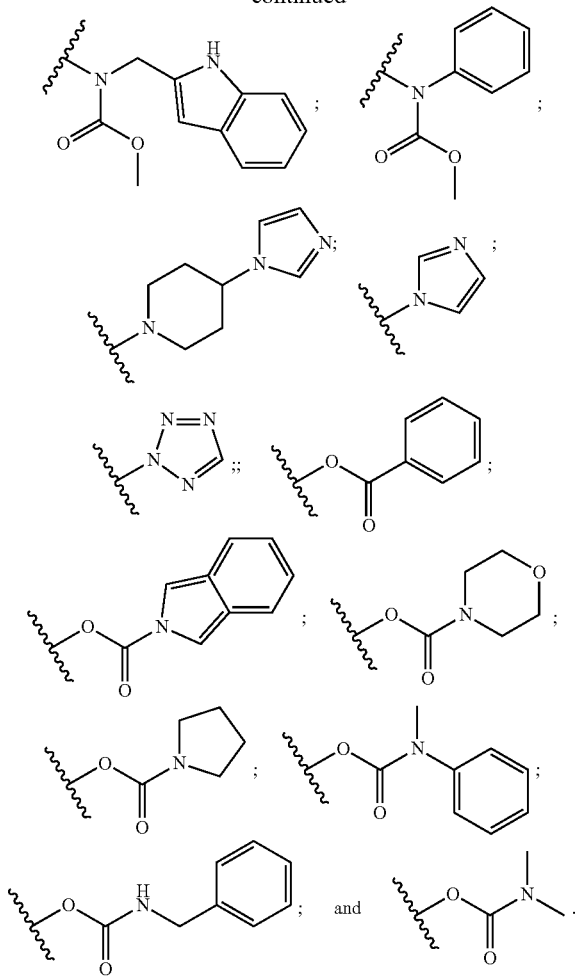

A further embodiment of the present invention includes pharmaceutical compositions comprising a compound of the invention, or a pharmaceutically acceptable salt, ester, solvate, or prodrug thereof, with a pharmaceutically acceptable carrier or excipient.

Yet another embodiment of the present invention is a pharmaceutical composition comprising a combination of two or more compounds delineated herein, or a pharmaceutically acceptable salt, ester, solvate, or prodrug thereof, with a pharmaceutically acceptable carrier or excipient.

Yet a further embodiment of the present invention is a pharmaceutical composition comprising any single compound delineated herein in combination with one or more anti-HCV compounds known in the art, or a pharmaceutically acceptable salt, ester, solvate, or prodrug thereof, with a pharmaceutically acceptable carrier or excipient.

It will be appreciated that reference herein to therapy and/or treatment includes, but is not limited to prevention, retardation, prophylaxis, therapy and cure of the disease. It will further be appreciated that references herein to treatment or prophylaxis of HCV infection includes treatment or prophylaxis of HCV-associated disease such as liver fibrosis, cirrhosis and hepatocellular carcinoma.

It will be further appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

It will be further appreciated that the compounds of the invention, or their pharmaceutically acceptable salts, stereoisomers, tautomers, prodrugs or salt of a prodrug thereof, can be administered as the sole active pharmaceutical agent, or used in combination with one or more agents to treat or prevent hepatitis C infections or the symptoms associated with HCV infection. Other agents to be administered in combination with a compound or combination of compounds of the invention include therapies for disease caused by HCV infection that suppresses HCV viral replication by direct or indirect mechanisms. These include agents such as host immune modulators (for example, interferon-alpha, pegylated interferon-alpha, interferon-beta, interferon-gamma, CpG oligonucleotides and the like), or antiviral compounds that inhibit host cellular functions such as inosine monophosphate dehydrogenase (for example, ribavirin and the like). Also included are cytokines that modulate immune function. Also included are vaccines which comprise HCV antigens or antigen adjuvant combinations directed against HCV. Also included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7 and the like. Other agents to be administered in combination with a compound of the present invention include any agent or combination of agents that inhibit the replication of HCV by targeting proteins of the viral genome involved in the viral replication. These agents include but are not limited to other inhibitors of HCV RNA dependent RNA polymerase such as, for example, nucleoside type polymerase inhibitors described in WO 01/90121 (A2), or U.S. Pat. No. 6,348,587B1 or WO 01/60315 or WO 01/32153 or non-nucleoside inhibitors such as, for example, benzimidazole polymerase inhibitors described in EP 1 162196A1 or WO 02/04425.

Accordingly, one aspect of the invention is directed to a method for treating or preventing an infection caused by an RNA-containing virus comprising co-administering to a patient in need of such treatment one or more agents selected from the group consisting of a host immune modulator and a second antiviral agent, or a combination thereof, with a therapeutically effective amount of a compound or combination of compounds of the invention, or a pharmaceutically acceptable salt, stereoisomer, tautomer, prodrug, salt of a prodrug, or combination thereof. Examples of the host immune modulator include, but are not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

A further aspect of the invention is directed to a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound or combination of compounds of the invention, or a pharmaceutically acceptable salt, stereoisomer, tautomer, prodrug, salt of a prodrug, or combination thereof. Yet another aspect of the invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound or a combination of compounds of the invention, or a pharmaceutically acceptable salt, stereoisomer, tautomer, prodrug, salt of a prodrug, or combination thereof. An agent that treats patients for disease caused by hepatitis B (HBV) infection may be for example, but not limited thereto, L-deoxythymidine, adefovir, lamivudine or tenfovir, or any combination thereof. An example of the RNA-containing virus includes, but not limited to, hepatitis C virus (HCV).

Another aspect of the invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound or a combination of compounds of the invention, or a pharmaceutically acceptable salt, stereoisomer, tautomer, prodrug, salt of a prodrug, or combination thereof. The agent that treats patients for disease caused by human immunodeficiency virus (HIV) infection may include, but is not limited thereto, ritonavir, lopinavir, indinavir, nelfmavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide (T-20) or T-1249, or any combination thereof. Example of the RNA-containing virus includes, but not limited to, hepatitis C virus (HCV). In addition, the present invention provides the use of a compound or a combination of compounds of the invention, or a therapeutically acceptable salt form, stereoisomer, or tautomer, prodrug, salt of a prodrug, or combination thereof, and one or more agents selected from the group consisting of a host immune modulator and a second antiviral agent, or a combination thereof, to prepare a medicament for the treatment of an infection caused by an RNA-containing virus in a patient, particularly hepatitis C virus. Examples of the host immune modulator are, but not limited to, interferon-alpha, pegylated-interferon-alpha, interferon-beta, interferon-gamma, a cytokine, a vaccine, and a vaccine comprising an antigen and an adjuvant, and said second antiviral agent inhibits replication of HCV either by inhibiting host cellular functions associated with viral replication or by targeting proteins of the viral genome.

When used in the above or other treatments, combination of compound or compounds of the invention, together with one or more agents as defined herein above, can be employed in pure form or, where such forms exist, in pharmaceutically acceptable salt form, prodrug, salt of a prodrug, or combination thereof. Alternatively, such combination of therapeutic agents can be administered as a pharmaceutical composition containing a therapeutically effective amount of the compound or combination of compounds of interest, or their pharmaceutically acceptable salt form, prodrugs, or salts of the prodrug, in combination with one or more agents as defined hereinabove, and a pharmaceutically acceptable carrier. Such pharmaceutical compositions can be used for inhibiting the replication of an RNA-containing virus, particularly Hepatitis C virus (HCV), by contacting said virus with said pharmaceutical composition. In addition, such compositions are useful for the treatment or prevention of an infection caused by an RNA-containing virus, particularly Hepatitis C virus (HCV).

Hence, further aspect of the invention is directed to a method of treating or preventing infection caused by an RNA-containing virus, particularly a hepatitis C virus (HCV), comprising administering to a patient in need of such treatment a pharmaceutical composition comprising a compound or combination of compounds of the invention or a pharmaceutically acceptable salt, stereoisomer, or tautomer, prodrug, salt of a prodrug, or combination thereof, one or more agents as defined hereinabove, and a pharmaceutically acceptable carrier.

When administered as a combination, the therapeutic agents can be formulated as separate compositions which are given at the same time or within a predetermined period of time, or the therapeutic agents can be given as a single unit dosage form.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from another anti-HCV agent; an HIV inhibitor; an HAV inhibitor; and an HBV inhibitor.

Other anti-HCV agents include those agents that are effective for diminishing or preventing the progression of hepatitis C related symptoms or disease. Such agents include but are not limited to immunomodulatory agents, inhibitors of HCV NS3 protease, other inhibitors of HCV polymerase, inhibitors of another target in the HCV life cycle and other anti-HCV agents, including but not limited to ribavirin, amantadine, levovirin and viramidine.

Immunomodulatory agents include those agents (compounds or biologicals) that are effective to enhance or potentiate the immune system response in a mammal. Immunomodulatory agents include, but are not limited to, inosine monophosphate dehydrogenase inhibitors such as VX-497 (merimepodib, Vertex Pharmaceuticals), class I interferons, class II interferons, consensus interferons, asialo-interferons pegylated interferons and conjugated interferons, including but not limited to interferons conjugated with other proteins including but not limited to human albumin. Class I interferons are a group of interferons that all bind to receptor type I, including both naturally and synthetically produced class I interferons, while class II interferons all bind to receptor type II. Examples of class I interferons include, but are not limited to, [alpha]-, [beta]-, [delta]-, [omega]-, and [tau]-interferons, while examples of class II interferons include, but are not limited to, [gamma]-interferons.

Inhibitors of HCV NS3 protease include agents (compounds or biologicals) that are effective to inhibit the function of HCV NS3 protease in a mammal Inhibitors of HCV NS3 protease include, but are not limited to, those compounds described in WO 99/07733, WO 99/07734, WO 00/09558, WO 00/09543, WO 00/59929, WO 03/064416, WO 03/064455, WO 03/064456, WO 2004/030670, WO 2004/037855, WO 2004/039833, WO 2004/101602, WO 2004/101605, WO 2004/103996, WO 2005/028501, WO 2005/070955, WO 2006/000085, WO 2006/007700 and WO 2006/007708 (all by Boehringer Ingelheim), WO 02/060926, WO 03/053349, WO03/099274, WO 03/099316, WO 2004/032827, WO 2004/043339, WO 2004/094452, WO 2005/046712, WO 2005/051410, WO 2005/054430 (all by BMS), WO 2004/072243, WO 2004/093798, WO 2004/113365, WO 2005/010029 (all by Enanta), WO 2005/037214 (Intermune) and WO 2005/

051980 (Schering), and the candidates identified as VX-950, ITMN-191 and SCH 503034.

Inhibitors of HCV polymerase include agents (compounds or biologicals) that are effective to inhibit the function of an HCV polymerase. Such inhibitors include, but are not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367, WO 2005/080388 and WO 2006/007693 (all by Boehringer Ingelheim), WO 2005/049622 (Japan Tobacco), WO 2005/014543 (Japan Tobacco), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates XTL-2125, HCV 796, R-1626 and NM 283.

Inhibitors of another target in the HCV life cycle include agents (compounds or biologicals) that are effective to inhibit the formation and/or replication of HCV other than by inhibiting the function of the HCV NS3 protease. Such agents may interfere with either host or HCV viral mechanisms necessary for the formation and/or replication of HCV. Inhibitors of another target in the HCV life cycle include, but are not limited to, entry inhibitors, agents that inhibit a target selected from a helicase, a NS2/3 protease and an internal ribosome entry site (IRES) and agents that interfere with the function of other viral targets including but not limited to an NS5A protein and an NS4B protein.

It can occur that a patient may be co-infected with hepatitis C virus and one or more other viruses, including but not limited to human immunodeficiency virus (HIV), hepatitis A virus (HAV) and hepatitis B virus (HBV). Thus also contemplated is combination therapy to treat such co-infections by co-administering a compound according to the present invention with at least one of an HIV inhibitor, an HAV inhibitor and an HBV inhibitor.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system including, but not limited to, phenyl, naphthyl, tetrahydronaphthyl, indanyl, idenyl.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl.

In accordance with the invention, any of the aryls, substituted aryls, heteroaryls and substituted heteroaryls described herein, can be any aromatic group. Aromatic groups can be substituted or unsubstituted.

The term "alkyl" as used herein, refers to saturated, straight- or branched-chain hydrocarbon radicals. For example, the terms "$C_1$-$C_4$ alkyl", "$C_1$-$C_6$ alkyl", "$C_1$-$C_8$ alkyl" and "$C_1$-$C_{12}$ alkyl," refer to alkyl groups containing one to four, one to six, one to eight, or one to twelve carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals; and examples of $C_1$-$C_{12}$ alkyl radicals include, but are not limited to, ethyl, propyl, isopropyl, n-hexyl, octyl, decyl, dodecyl radicals.

The term "alkenyl," as used herein, refers to straight- or branched-chain hydrocarbon radicals having at least one carbon-carbon double bond. For example, the terms "$C_2$-$C_4$ alkenyl", "$C_2$-$C_6$ alkenyl," and "$C_2$-$C_8$ alkenyl" refer to alkenyl groups containing two to four, two to six or two to eight carbon atoms respectively. Alkenyl groups include, but are not limited to, for example, ethenyl, propenyl, butenyl, 1-methyl-2-buten-1-yl, heptenyl, octenyl, and the like.

The term "alkynyl," as used herein, refers to straight- or branched-chain hydrocarbon radicals having at least one carbon-carbon triple bond. For example, the terms "$C_2$-$C_4$ alkynyl", "$C_2$-$C_6$ alkynyl," and "$C_2$-$C_8$ alkynyl" refer to alkynyl groups containing two to four, two to six or two to eight carbon atoms respectively. Representative alkynyl groups include, but are not limited to, for example, ethynyl, 1-propynyl, 1-butynyl, heptynyl, octynyl, and the like.

The term "alkylene", as used herein, refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through two single bonds. The points of attachment of the alkylene chain to the rest of the molecule can be through any two carbons within the chain.

The term "alkenylene", as used herein, refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through two double bonds, through two single bonds or through one single bond and one double bond. The points of attachment of the alkenylene chain to the rest of the molecule can be through any two carbons within the chain.

The term "alkynylene", as used herein, refers straight or branched divalent hydrocarbon chain linking the rest of the molecule to a radical group, consisting solely of carbon and hydrogen, containing at least one triple bond and having from two to twelve carbon atoms, for example, propynylene, n-butynylene, and the like. The alkynylene chain is attached to the rest of the molecule through two double bonds, through two single bonds or through one single bond and one double bond. The points of attachment of the alkynylene chain to the rest of the molecule can be through any two carbons within the chain.

The term "Cycloalkylene", as used herein, refers to a divalent cycloalkyl group, as defined above, which is attached to the rest of the molecule through two different carbons in the cycloalkylene group. An example of an cycloalkylene group is shown below:

The cycloalkylene group may be optionally substituted as defined above for an cycloalkyl group.

The term "cycloalkyl" as used herein, refers to monocyclic or polycyclic saturated carbocyclic ring radicals. For example, the terms "$C_3$-$C_8$-cycloalkyl" and "$C_3$-$C_{12}$-cycloalkyl" refer to cycloalkyl groups containing three to eight or three to twelve carbon atoms respectively. Examples of $C_3$-$C_8$-cycloalkyl groups include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1]heptyl, and bicyclo[2.2.2]octyl.

The term "cycloalkenyl", as used herein, refers to monocyclic or polycyclic carbocyclic ring radicals having at least one carbon-carbon double bond. For example, the terms "$C_3$-$C_8$ cycloalkenyl" or "$C_3$-$C_{12}$ cycloalkenyl" refer to cycloalkenyl groups containing three to eight or three to twelve carbon atoms respectively. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$ cycloalkenyl include, but not limited to, cyclopropenyl, cyclobutenyl, cyclopentenyl, cyclohexenyl, cycloheptenyl, cyclooctenyl, and the like.

It is understood that any alkyl, alkenyl, alkynyl and cycloalkyl moiety described herein can also be an aliphatic group, an alicyclic group or a heterocyclic group. An "aliphatic" group is a non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The term "alicyclic," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocyclic groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted.

The term "substituted" refers to substitution by independent replacement of one, two, or three or more of the hydrogen atoms thereon with substituents including, but not limited to, —F, —Cl, —Br, —I, —OH, protected hydroxy, —$NO_2$, —CN, —$N_3$, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted.

The term "halogen," as used herein, refers to an atom selected from fluorine, chlorine, bromine and iodine.

The term "hydroxy activating group", as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxy", as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bz or —C(O)C$_6$H$_5$), and trimethylsilyl (TMS or —Si(CH$_3$)$_3$).

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group", as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992).

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. *Wuts, Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "protected amino," as used herein, refers to an amino group protected with an amino protecting group as defined above.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

The term "protic solvent" as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2$^{nd}$ Ed. Wiley-VCH (1999); T. W. Greene and P. G. M. Wuts, *Protective Groups in Organic Synthesis,*

3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of the invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., *Journal of Drug Deliver Reviews*, 8:1-38(1992); Bundgaard, *J. of Pharmaceutical Sciences*, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The present invention also relates to solvates of the compounds of Formula (I), for example hydrates.

This invention also encompasses pharmaceutical compositions containing, and methods of treating viral infections through administering, pharmaceutically acceptable prodrugs of compounds of the invention. For example, compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the Formula described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the invention described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (eg N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Unless otherwise defined, all technical and scientific terms used herein are accorded the meaning commonly known to one of ordinary skill in the art. All publications, patents, published patent applications, and other references mentioned herein are hereby incorporated by reference in their entirety.

Abbreviations

Abbreviations which may be used in the descriptions of the scheme and the examples that follow are:
Ac for acetyl;
Boc$_2$O for di-tert-butyl-dicarbonate;
Boc for t-butoxycarbonyl;
Bz for benzoyl;
Bn for benzyl;
BocNHOH for tert-butyl N-hydroxycarbamate;
t-BuOK for potassium tert-butoxide;
BOP for (benzotriazol-1-yloxy)tris(dimethylamino)phosphonium Hexafluorophosphate;
Brine for sodium chloride solution in water;
CDI for carbonyldiimidazole;
$CH_2Cl_2$ for dichloromethane;
$CH_3$ for methyl;
$CH_3CN$ for acetonitrile;
$Cs_2CO_3$ for cesium carbonate;
dba for dibenzylidene acetone;
dppb for diphenylphosphino butane;
dppe for diphenylphosphino ethane;
DBU for 1,8-diazabicyclo[5.4.0]undec-7-ene;
DCC for N,N'-dicyclohexylcarbodiimide;
DEAD for diethylazodicarboxylate;
DIAD for diisopropyl azodicarboxylate;
DIPEA or (i-Pr)$_2$EtN for N,N,-diisopropylethyl amine;
Dess-Martin periodinane for 1,1,1-tris(acetyloxy)-1,1-dihydro-1,2-benziodoxol-3-(1H)-one;
DMAP for 4-dimethylaminopyridine;
DME for 1,2-dimethoxyethane;
DMF for N,N-dimethylformamide;
DMSO for dimethyl sulfoxide;
DPPA for diphenylphosphoryl azide;
EDC for N-(3-dimethylaminopropyl)-N'-ethylcarbodiimide;
EDC HCl for N-(3-dimethylaminopropyl)-N'-ethylcarbodiimide hydrochloride;
EtOAc for ethyl acetate;
EtOH for ethanol;
Et$_2$O for diethyl ether;
HATU for O-(7-azabenzotriazol-1-yl)-N,N,N',N',-tetramethyluronium Hexafluorophosphate;
HCl for hydrogen chloride;
HOBT for 1-hydroxybenzotriazole;
K$_2$CO$_3$ for potassium carbonate;
MeOH for methanol;
Ms for mesyl or —SO$_2$—CH$_3$;
Ms$_2$O for methanesulfonic anhydride or mesyl-anhydride;
NaHCO$_3$ for sodium bicarbonate or sodium hydrogen carbonate;
Na$_2$CO$_3$ sodium carbonate;
NaOH for sodium hydroxide;
Na$_2$SO$_4$ for sodium sulfate;
NaHSO$_3$ for sodium bisulfite or sodium hydrogen sulfite;
Na$_2$S$_2$O$_3$ for sodium thiosulfate;
NH$_2$NH$_2$ for hydrazine;
NH$_4$HCO$_3$ for ammonium bicarbonate;
NH$_4$Cl for ammonium chloride;
NMMO for N-methylmorpholine N-oxide;
NaIO$_4$ for sodium periodate;
OH for hydroxy;
OsO$_4$ for osmium tetroxide;
TEA or Et$_3$N for triethylamine;
TFA for trifluoroacetic acid;
THF for tetrahydrofuran;
TPP or PPh$_3$ for triphenylphosphine;
Ts for tosyl or —SO$_2$—C$_6$H$_4$CH$_3$;
Ts$_2$O for tolylsulfonic anhydride or tosyl-anhydride;
TsOH for p-tolylsulfonic acid;
Pd for palladium;
Ph for phenyl;
Pd$_2$(dba)$_3$ for tris(dibenzylideneacetone) dipalladium (O);
Pd(PPh$_3$)$_4$ for tetrakis(triphenylphosphine)palladium (O);
TBS for tert-butyl dimethylsilyl; or
TMS for trimethylsilyl;
TMSCl for trimethylsilyl chloride;

CsA for cyclosporine A.

Synthetic Methods

The compounds and processes of the present invention will be better understood in connection with the following synthetic schemes that illustrate the methods by which the compounds of the invention may be prepared.

As shown in Scheme 1, novel cyclosporine analogues of the present invention are prepared from cyclosporine A derivative, the compound of formula (1-11), which can be obtained from polypeptide, the compound of formula (1-7) and dipeptide, the compound of formula (1-4). The dipeptide compound of formula (1-4) is prepared from glycine derivative compound of formula (1-1). Also, polypeptide compound of formula (1-7) is prepared by selective removal of two amino acids in position three and four of cyclosporine A according to the procedure described in WO 2010/088573. Glycine derivative compound of formula (1-1) is prepared by the modified procedure from Corcella, F.; Rossi, F.; Caldarelli, F. S.; Heidempergher, F.; Marchionni, C.; Auguadro, M.; Cattaneo, M.; Ceriani, L.; Visentin, G.; Ventrella, G.; Pinciroli, V.; Ramella, G.; Candiani, I.; Bedeschi, A.; Tomasi, A.; Kline, B. J.; Martinez, C. A.; Yazbeck, D.; Kucera, D. J., *Orgnic Process Research & Development*, 2008, 12, 322. Then, compound of formula (1-1) is converted to benzyl or methyl ester, herein $P_1$ is Boc, followed by N-methylation to give the compound of formula (1-3). The compound of formula (1-3) is deprotected in acidic condition and then be coupled with Fmoc protected N-methyl-D-alanine to afford dipeptide, the compound of formula (1-4). The acid for deprotection can be selected from, but not limited to, TFA, HCl in dioxane, methanesulfonic acid. A more detailed discussion of the procedures, reagents and conditions for removing protecting groups is described in literature, for example, by T. W. Greene and P. G. M. Wuts in "*Protective Groups in Organic Synthesis*" $3^{rd}$ ed., John Wiley & Son, Inc., 1999. The coupling regent can be selected from, but not limited to, DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, $CH_2Cl_2$, DMF or THF. The reaction temperature can vary from 0° C. to about 50° C. Dipeptide, the compound of formula (1-4) is further subjected to oxidative cleavage to give an aldehyde which subsequently is protected to give the compound of formula (1-5). Oxidative cleavage includes, but not limited to ozonolysis and osmium teroxide/sodium periodate. Aldehyde protections include, but not limited to dimethoxy acetal, dioxolane acetal and cyanohydrin. Then, the compound of formula (1-5) is converted to the compound of formula (1-6) by either hydrogenation or alkaline hydrolysis. Thus, coupling of polypeptide compound of formula (1-7) and the compound of formula (1-6) provides the compound of formula (1-8).

Scheme 1

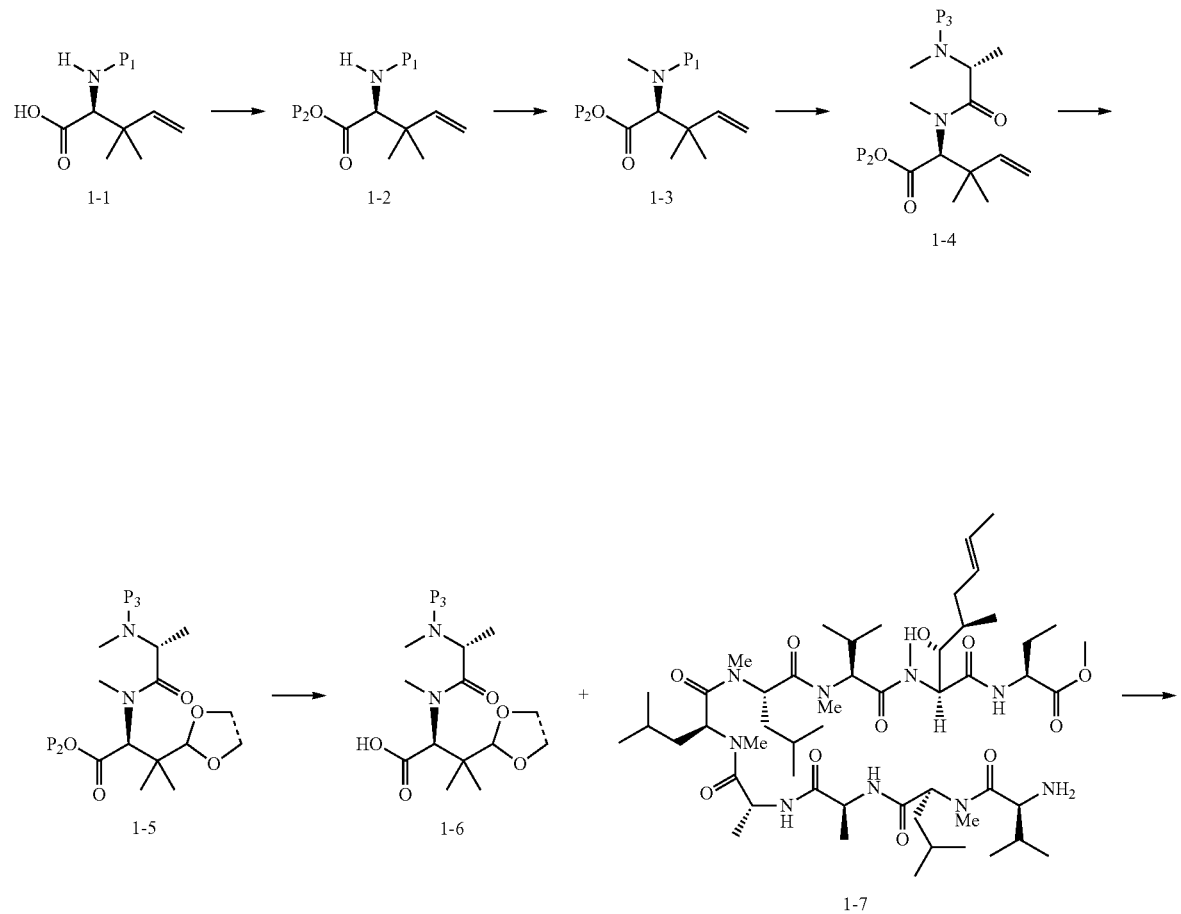

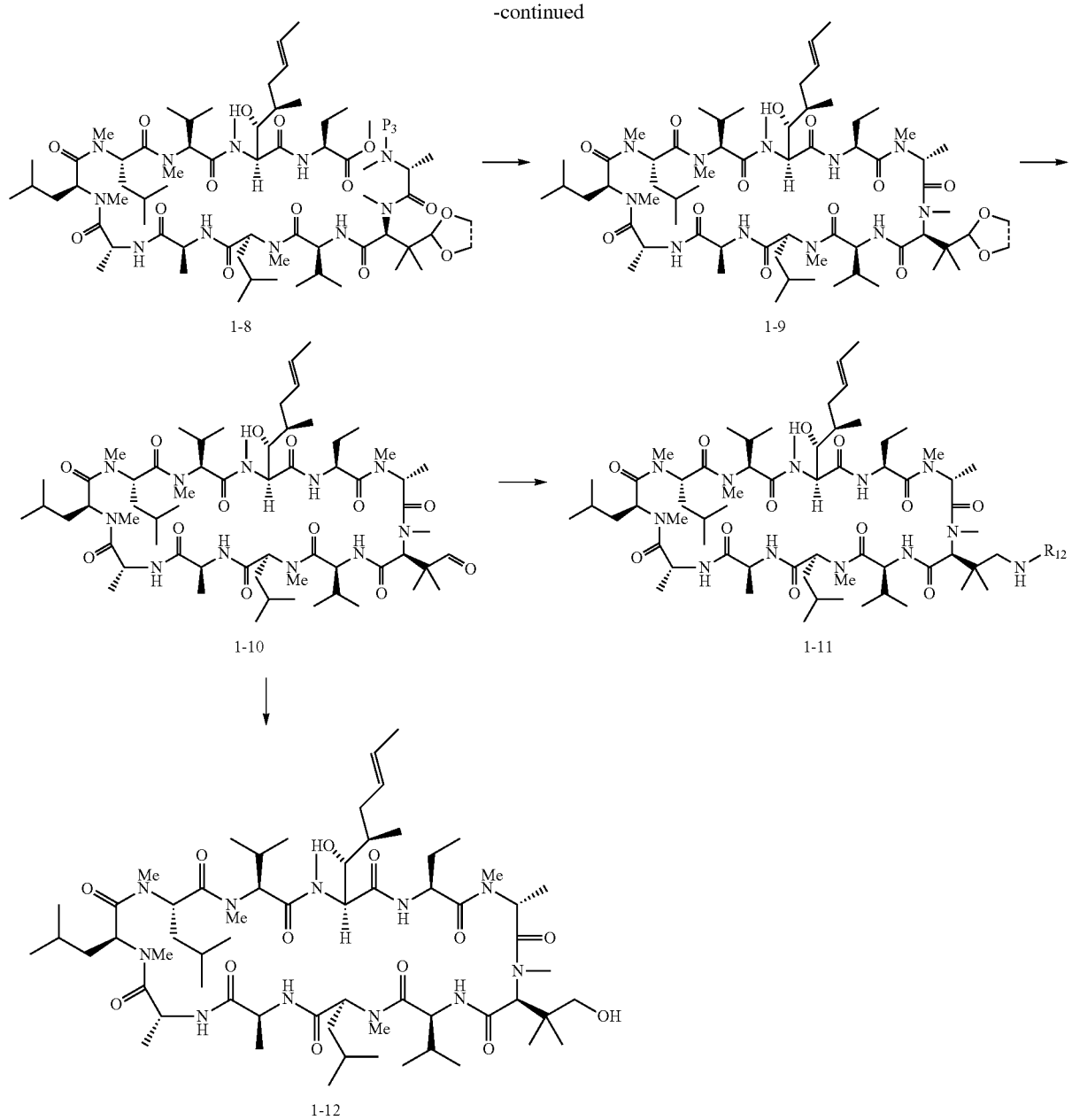

Compound of formula (1-9) is prepared from the compound of formula (1-8) by alkaline hydrolysis of methyl ester to corresponding carboxylic acid followed by amino deprotection of P1 and subsequent macrocyclization via intramolecular amide formation reaction. For alkaline hydrolysis, the representative alkali compounds include lithium hydroxide, sodium hydroxide, potassium hydroxide, and the like. Suitable solvents for alkaline hydrolysis include, but are not limited to, methanol, ethanol, isopropanol, butanol, THF, 1, 4-dioxane and mixtures there of. The amino deprotection is conducted using the condition which depends on the nature of P1 group. A more detailed discussion of the procedures, reagents and conditions for removing protecting groups is described in literature, for example, by T. W. Greene and P. G. M. Wuts in "*Protective Groups in Organic Synthesis*" 3$^{rd}$ ed., John Wiley & Son, Inc., 1999.

The regent for intramolecular amide formation reaction can be selected from, but not limited to DCC, EDC, di-isopropyl carbodiimide, BOP-Cl, PyBOP, PyAOP, TFFH and HATU. Suitable bases include, but are not limited to, triethylamine, diisopropylethylamine, DBU, N-methylmorpholine and DMAP. The coupling reaction is carried out in an aprotic solvent such as, but not limited to, CH$_2$Cl$_2$, DMF and THF. The reaction temperature can vary from 0° C. to about 50° C. The acid used for regenerating aldehyde compound of formula (1-10) from the compound of formula (1-9) can be selected from, but not limited to, TFA, HCl in dioxane, methanesulfonic acid. A more detailed discussion of the procedures, reagents and conditions for removing protecting groups is described in literature, for example, by T. W. Greene and P. G. M. Wuts in "*Protective Groups in Organic Synthesis*" 3$^{rd}$ ed., John Wiley & Son, Inc., 1999. The aldehyde compound of formula (1-10) is subjected either reduction or reductive amination to provide either alcohol compound of formula (1-12) or amino compound of formula (1-11), respectively. Reducing agents include, but not limited to sodium borohydride, sodium cyanoborohydride and sodium triacethoxyborohydride.

Scheme 2 depicted another process to prepare for the novel cyclosporine analogues of the present invention by modification of compound of formula (1-12) or compound of formula (1-11). Thus, compound of formula (1-11) or (1-12) was transformed to the compound of formula (V, as previously defined) by different functional group transformation reactions. A thorough discussion of different functional group transformation reactions is described in literature, for example, by Richard C. Larock in "Comprehensive Organic Transformations" 2$^{rd}$ ed., John Wiley & Son, Inc., 1999. Compound formula (V) was further transformed to compound formula (II, as previously defined) through an olefin cross metathesis (CM) reaction as a key step.

A number of account and literature regarding CM reaction are reported; i.e., Chatterjee, A. K.; Choi, T-L; Sanders, D. P.; Grubbs, R. H., *J. Am. Chem. Soc.,* 2003, 125, 11360; Scholl, S; Ding, S.; Lee, C. W.; Grubbs, R. H., *Org. Lett.* 1999, 1, 953; Hoveyda, A. H.; Zhugralin, A. R., *Nature,* 2007, 450, 243. The catalyst used in cross metathesis reactions are, such as but not limited to Grubbs catalyst 1$^{st}$ and 2$^{nd}$ generation, Hoveyda-Grubbs catalyst 1$^{st}$ and 2$^{nd}$ generation, Zhan-1A, Zhan-1B and Zhan-1C. The catalysts used in catalytic hydrogenation are such as, but not limited to, 5% palladium on carbon, 10% palladium on carbon, PtO$_2$, palladium hydroxide.

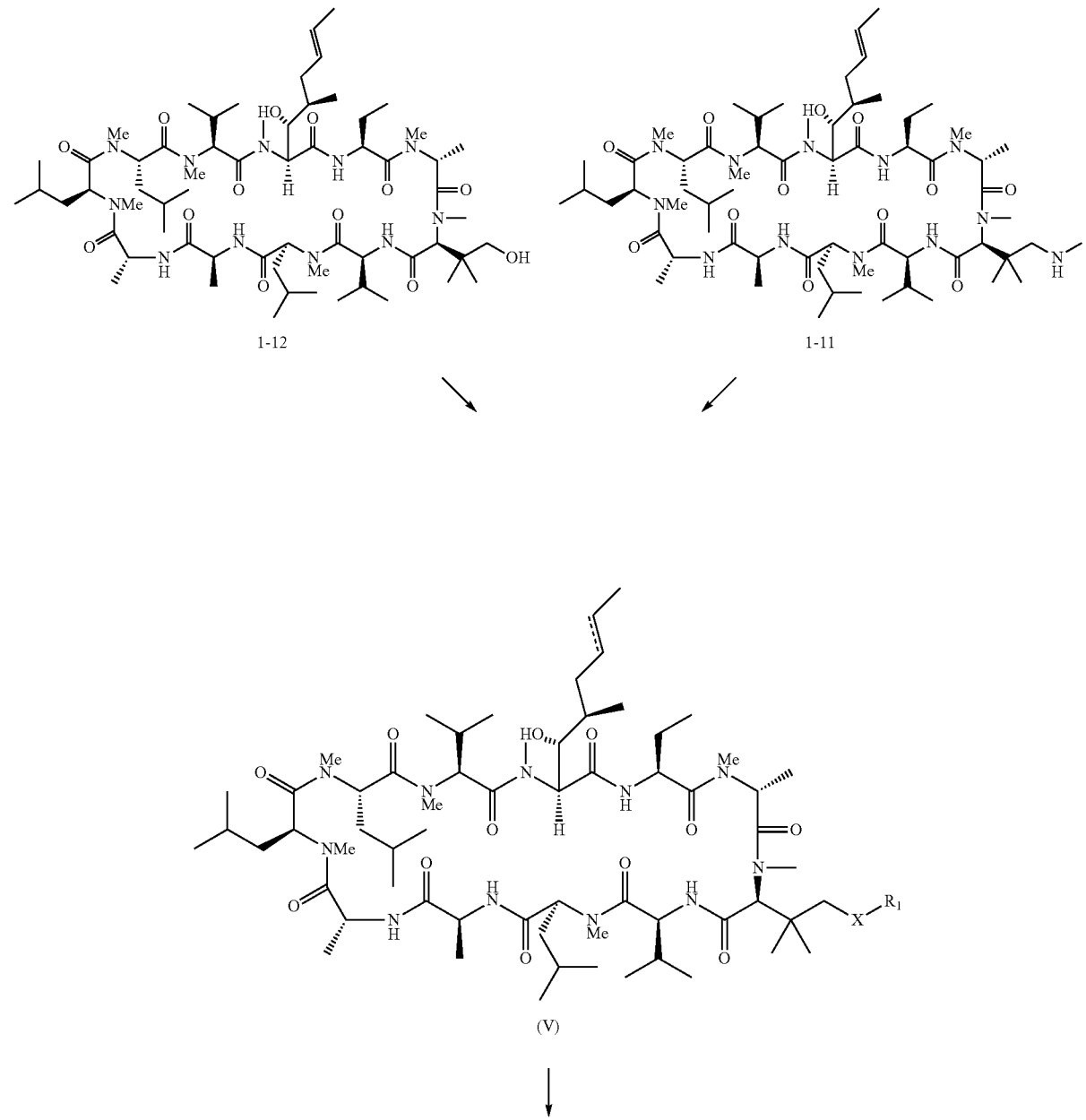

Scheme 2

-continued

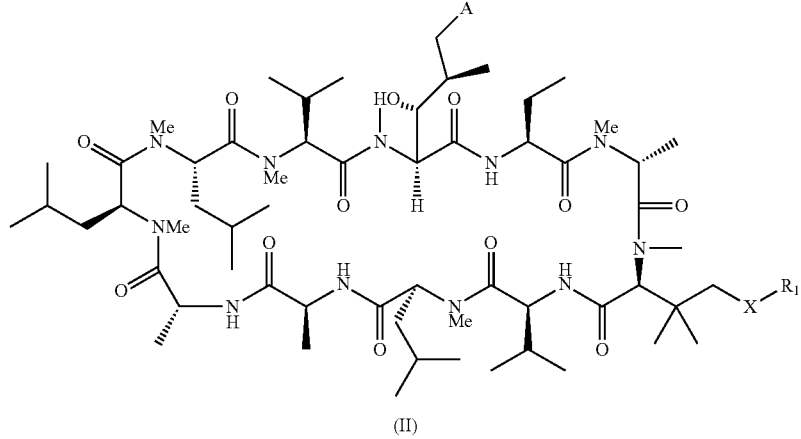

(II)

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

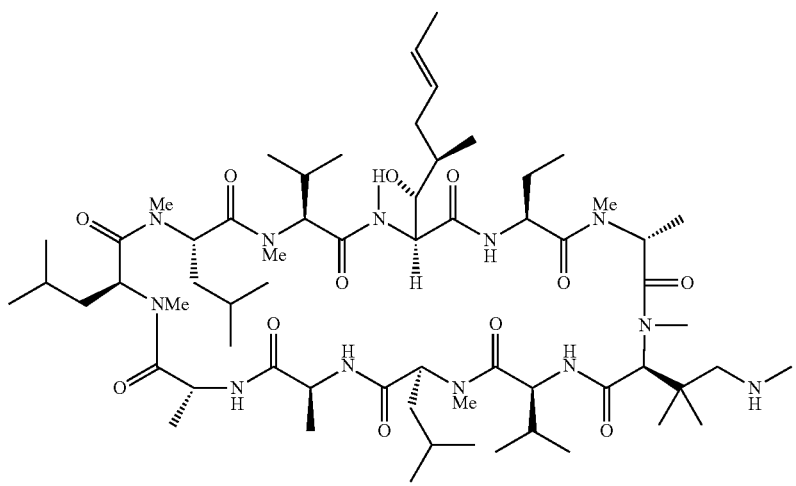

Step 1-1:

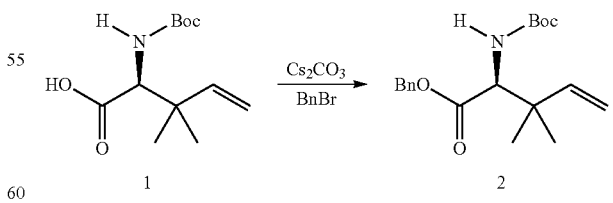

To a mixture of 1 (7.396 g, 30.4 mmol) in dry DMF (59 mL) was added cesium carbonate (10.103 g, 31.0 mmol) at 0° C. and stirred for 35 min, treated with benzyl bromide (3.9 mL, 31.83 mmol) for 2 min and stirred between 3° C. and 6.5° C. for 2 hrs. Then, it was allowed to warm to room temperature and stirred for 2 hrs. The reaction was cooled to 0° C., quenched by addition of 1N—HCl (31 mL, pH~4), diluted with MTBE (300 mL), washed with H₂O (3 times) and brine. The organic layer was dried over Na₂SO₄, filtered, concentrated to dryness. The residue was purified by SiO₂ column chromatography with 0~10% ethyl acetate in hexanes to provide the compound 2 (10.05 g) as a colorless oil, MS: (ESI) m/z 333.97 (M+H)⁺.

Step 1-2:

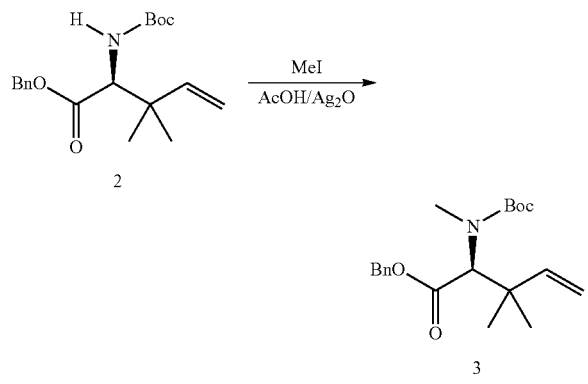

A mixture of 2 (10.05 g, 30.14 mmol) and silver oxide (17.5 g, 75.36 mmol) in dry DMF (75 mL) was degassed and filled with N₂. Then, acetic acid (1.73 mL, 30.14 mmol) and iodomethane (28.1 mL, 452.13 mmol) were added to the reaction, and vigorously stirred at room temperature for 24 hrs in the dark place. The completion of the reaction was confirmed by hplc. The reaction mixture was diluted with MTBE (100 mL), filtered through a pad of celite, washed with saturated NaHCO₃ sol'n and separated. The aqueous layer was extracted with MTBE. The combined organic layer was washed with H₂O (3 times) and brine. The organic layer was dried over Na₂SO₄, filtered, concentrated to dryness. The residue was dried on vacuum pump to provide the compound 3 (10.318 g) as a colorless oil. MS: (ESI) m/z 347.92 (M+H)⁺, 370.27 (M+Na)⁺.

Step 1-3:

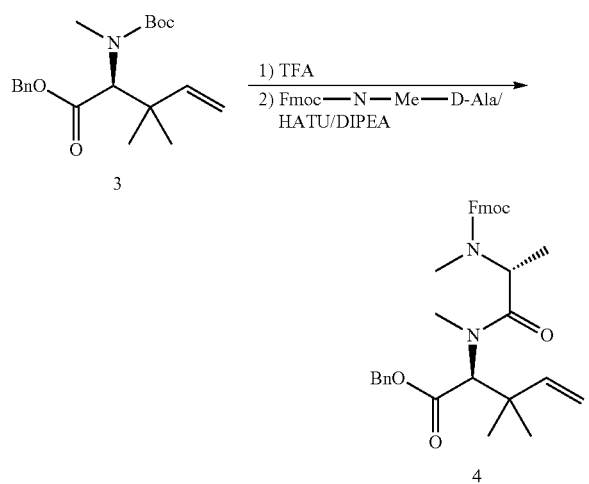

To a mixture of 3 (9.315 g, 26.8 mmol) in dry CH₂Cl₂ (74 mL) was dropwise added TFA (37.2 mL, 482.4 mmol) at 0° C. and stirred for 70 min. The reaction was basified with saturated NaHCO₃ solution-20% aqueous K₂CO₃ solution (4:1, 8 volumes to TFA) and separated. The aqueous layer was extracted with CH₂Cl₂. The combined organic layer was washed with brine, dried over Na₂SO₄, filtered, concentrated to dryness. The residue was briefly dried on vacuum pump and used for the next reaction without further purification. Thus, deprotected amine and Fmoc-N-Me-D-ala (15.7 g, 48.2 mmol) were dissolved in dry CH₂Cl₂ (54 mL), treated with DIPEA (15.4 mL, 88.44 mmol) and HATU (22.0 g, 57.89 mmol) at room temperature and stirred for 22 hrs. The reaction was concentrated in vacuo, diluted with ethyl acetate (300 mL), washed with 1N—HCl (80 mL), H₂O (50 mL) and brine. The organic layer was dried over Na₂SO₄, filtered, concentrated to dryness. The residue was purified by SiO₂ column Chromatography with 0~40% ethyl acetate in hexanes to provide the compound 4 (12.46 g) as a white foam. MS: (ESI) m/z 555.20 (M+H)⁺, 577.40 (M+Na)⁺.

Step 1-4:

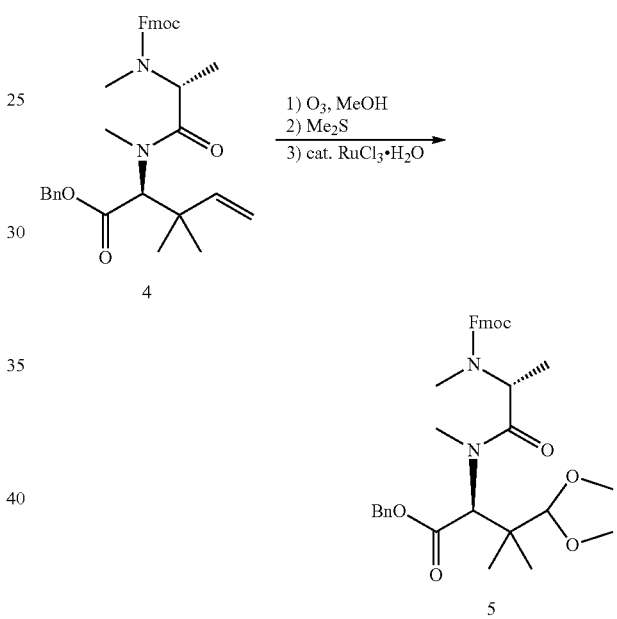

To a mixture of 4 (8.469 g, 15.29 mmol) in dry MeOH (400 mL) was passed through ozone at −78° C. until the pale blue color persisted. Subsequently, oxygen and nitrogen passed through the solution. Then, dimethyl sulfide (11 mL, 149.63 mmol) was added to the reaction, allowed to warm to room temperature and stirred for 21 hrs. The reaction was evaporated off, dissolved in dry MeOH (85 mL), treated with ruthenium chloride monohydrate (95 mg, 0.46 mmol) and stirred for ~1 day. The reaction was evaporated off, diluted with ethyl acetate (300 mL) and H₂O (50 mL) and separated. The aqueous layer was extracted with ethyl acetate (2×50 mL). The combined organic layer was washed with brine. The organic layer was dried over Na₂SO₄, filtered, concentrated to dryness. The residue was separated by SiO₂ column chromatography with 0~20% acetone in hexanes to provide the title compound with unreacted aldehyde (670 mg). Unreacted aldehyde was converted to the title compound in the same way. Two batches were combined to give the compound 5 (8.097 g) as a white foam. MS: (ESI) m/z 625.46 (M+Na)⁺.

Step 1-5:

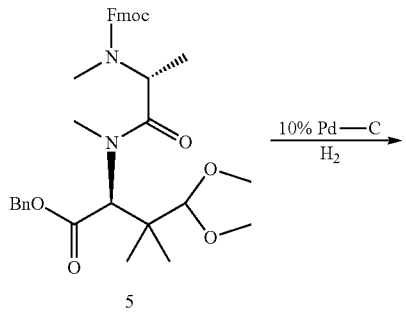

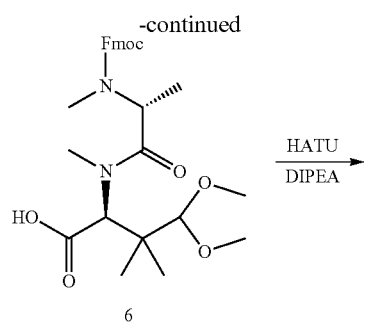

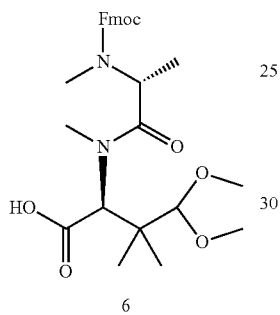

A mixture of 5 (8.088 g, 13.42 mmol) and 10% palladium-carbon (2.43 g) in ethyl acetate-t-BuOH (4:1, 400 mL) was cooled to −40° C., degassed and filled with H₂ (repeated 3 times). The reaction mixture was vigorously stirred at room temperature for 2 hrs. The reaction mixture was filtered through a pad of celite, washed with ethyl acetate-t-BuOH (4:1, 100 mL), concentrated in vacuo and dried on vacuum pump to give the compound 6 (6.58 g) as a white foam. MS: (ESI) m/z 535.38 (M+Na)⁺.

Step 1-6:

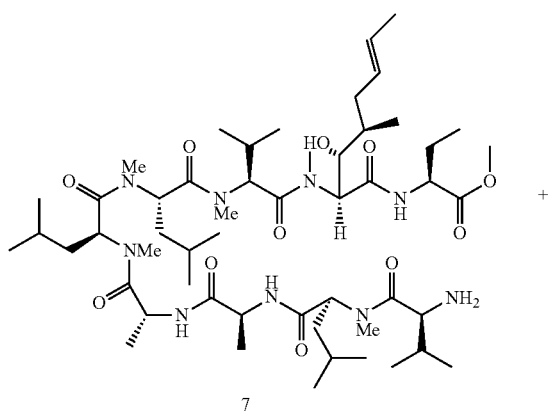

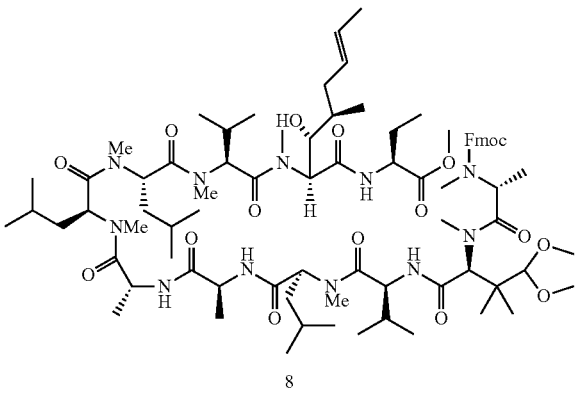

A mixture of 7 (11.973 g, 11.553 mmol) and 6 (6.58 g, 12.837 mmol) in dry CH₂Cl₂ (130 mL) was cooled to 2° C., treated with DIPEA (6.7 mL, 38.511 mmol) and HATU (5.86 g, 15.40 mmol), successively. The reaction was stirred between 2 and 9° C. for 140 min. The reaction mixture was diluted with ethyl acetate (300 mL), washed with sat. NaHCO₃ solution (70 mL) and brine (50 mL) and separated. The organic layer was dried over Na₂SO₄, filtered, concentrated to dryness. The residue was purified by SiO₂ column chromatography with 0~6% methanol in CH₂Cl₂ to provide the compound 8 (13.677 g) as a white foam. MS: (ESI) m/z 1530.72 (M+H)⁺, 1552.93 (M+Na)⁺.

Step 1-7:

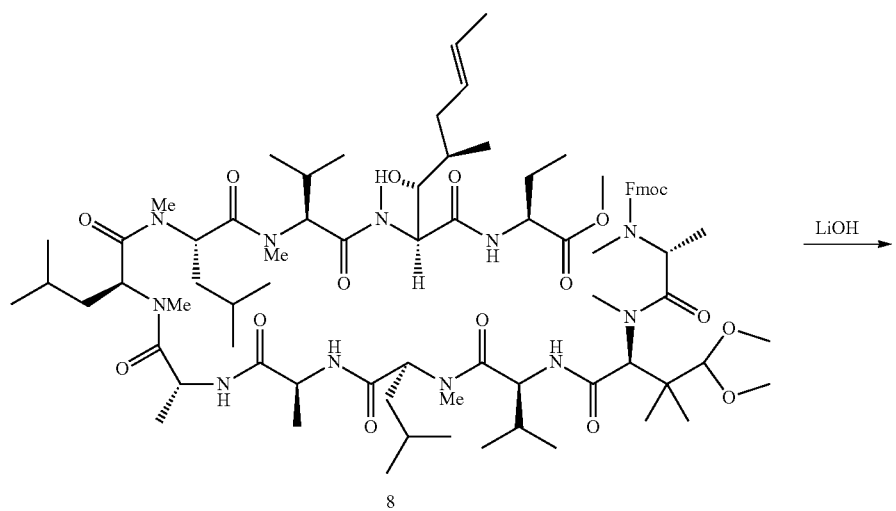

8

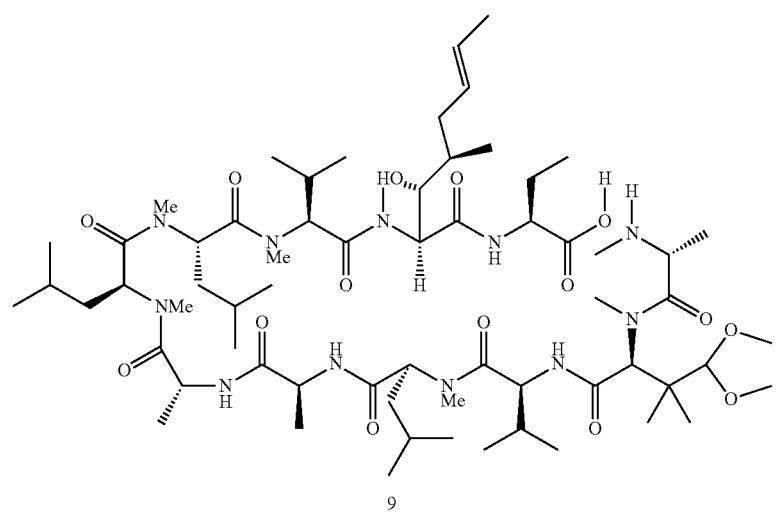

9

To a mixture of 8 (13.058 g, 8.529 mmol) in THF-MeOH—H₂O (5:2:2, 108 mL) was added lithium hydroxide monohydrate (1.789 g, 42.65 mmol) at 0° C. and stirred for 1 hr. Then, H₂O (80 mL) was added to the reaction, which was neutralized with 1N—HCl (40 mL, pH~6.5) at 0° C. The reaction was extracted with extracted with CH₂Cl₂ (2×300 mL). The combined organic layer was washed with brine, dried over Na₂SO₄, filtered and concentrated in vacuo to give compound 9 and used for the next reaction without further purification. MS: (ESI) m/z 1294.85 (M+H) 1316.95 (M+Na)⁺.

Step 1-8:

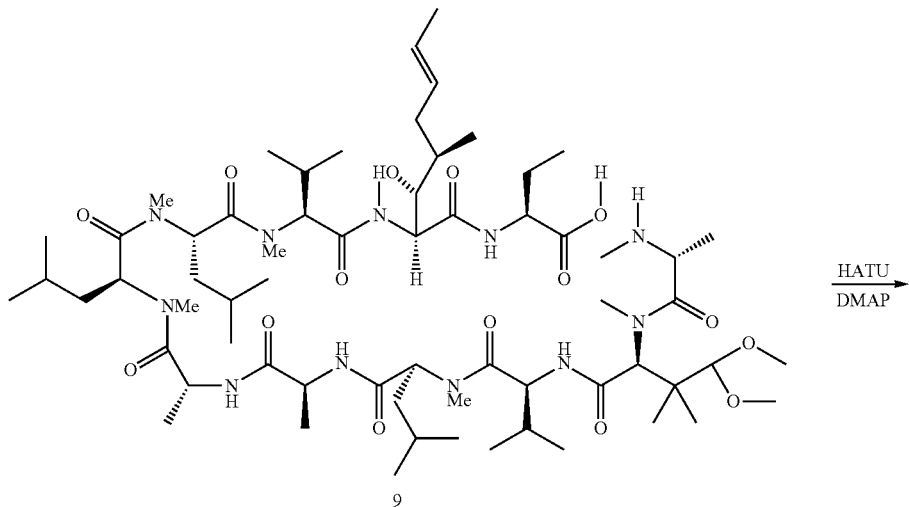

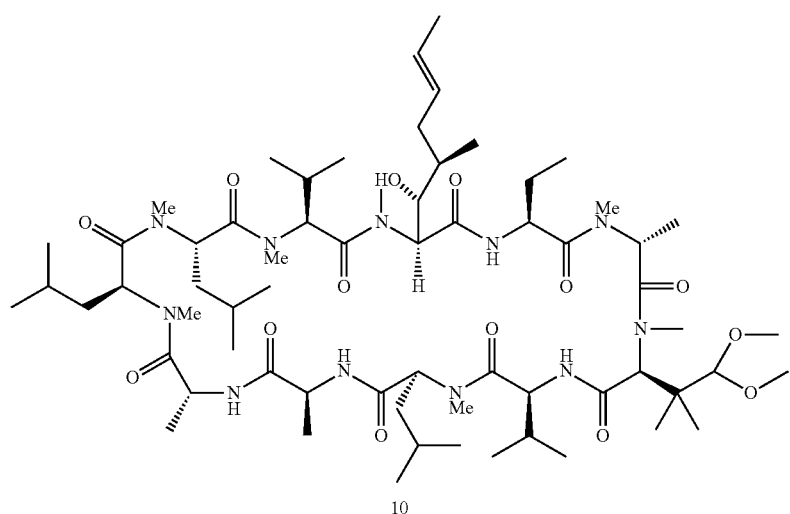

To a mixture of HATU (4.865 g, 12.79 mmol) and DMAP (1.563 g, 12.79 mmol) in dry $CH_2Cl_2$ (350 mL) was dropwise added a solution of crude 9 in dry $CH_2Cl_2$ (550 mL) at 36° C. for 1 hr and stirred at 36° C. for 14.5 hr. The reaction mixture was filtered through a fritted funnel and washed with sat. $NaHCO_3$ solution (200 mL) and brine (70 mL) and separated. The organic layer was dried over $Na_2SO_4$, filtered and concentrated to dryness.

The residue was triturated with MTBE, filtered through a frilled funnel and concentrated to dryness. The residue was purified by $SiO_2$ column chromatography with 0~6% methanol in $CH_2Cl_2$ to provide the compound 10 (7.47 g) as a white team. MS: (ESI) m/z 1276.49 $(M+H)^+$, 1298.96 $(M+Na)^+$.

Step 1-9:

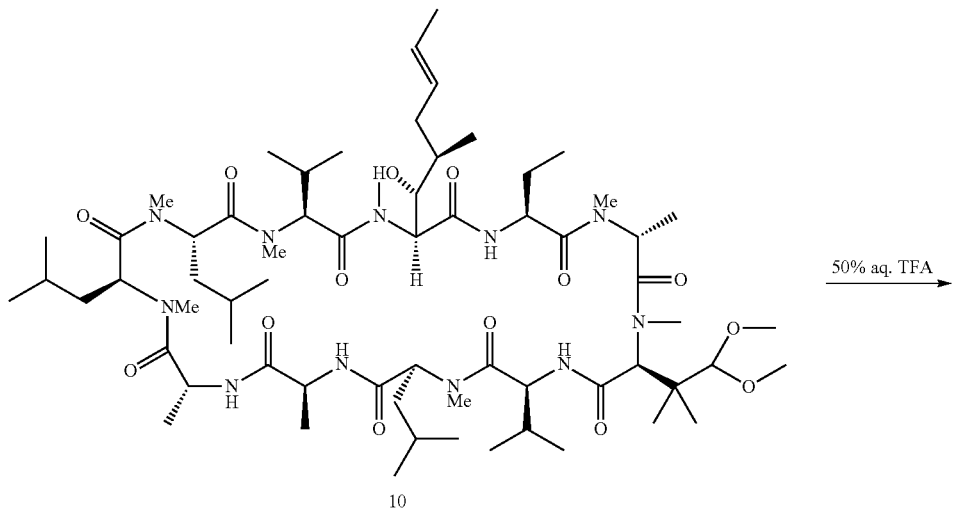

10

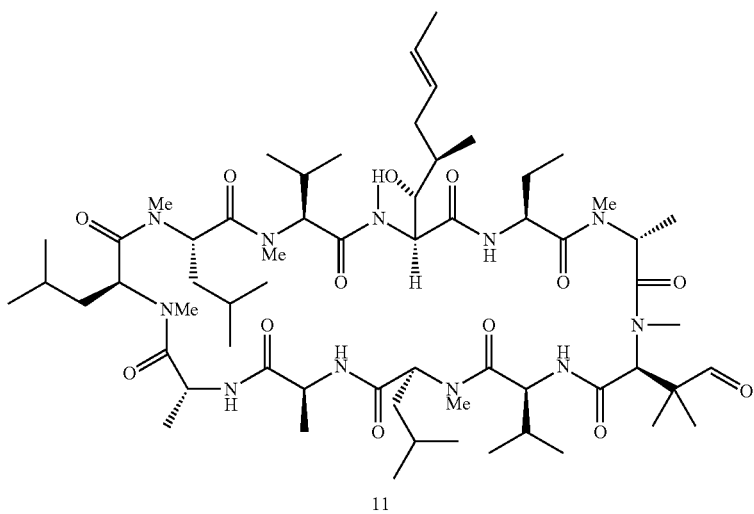

11

A mixture of 10 (5.973 g, 4.679 mmol) in dry CH$_2$Cl$_2$ (50 mL) was cooled to 0° C., treated with 50% aq. TFA (25 mL) and stirred at 0° C. for 1 hr. The reaction was poured into ice-cold sat. NaHCO$_3$ solution-20% aq. K$_2$CO$_3$ solution (4:1, 225 mL) with vigorous stirring. The reaction mixture was separated. The aqueous layer was extracted with CH$_2$Cl$_2$ (2 times). The combined organic layer was washed with brine. The organic layer was dried over Na$_2$SO$_4$, filtered, concentrated to dryness. The residue was purified by SiO$_2$ column chromatography with 0~60% acetone in hexanes to provide the compound 11 (3.037 g) as a white foam. MS: (ESI) m/z 1230.84 (M+H)$^+$, 1252.92 (M+Na)$^+$.

Step 1-10:

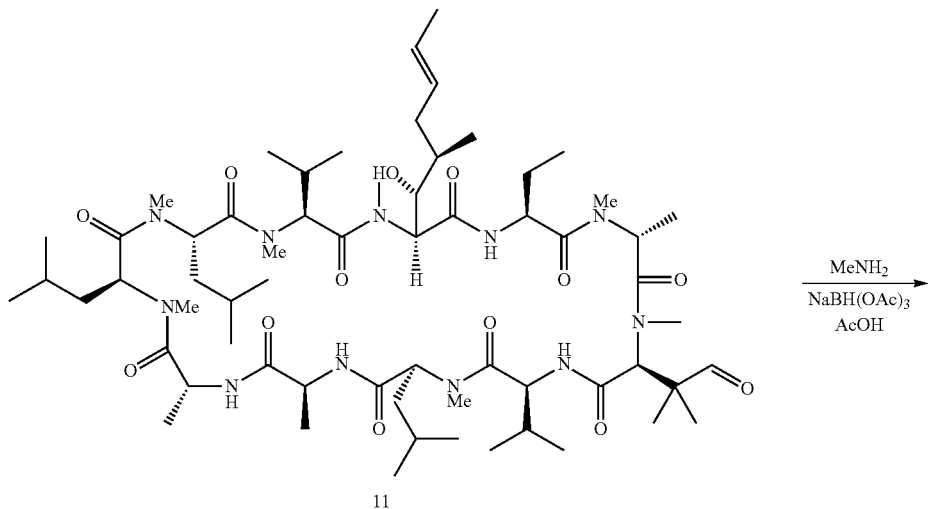

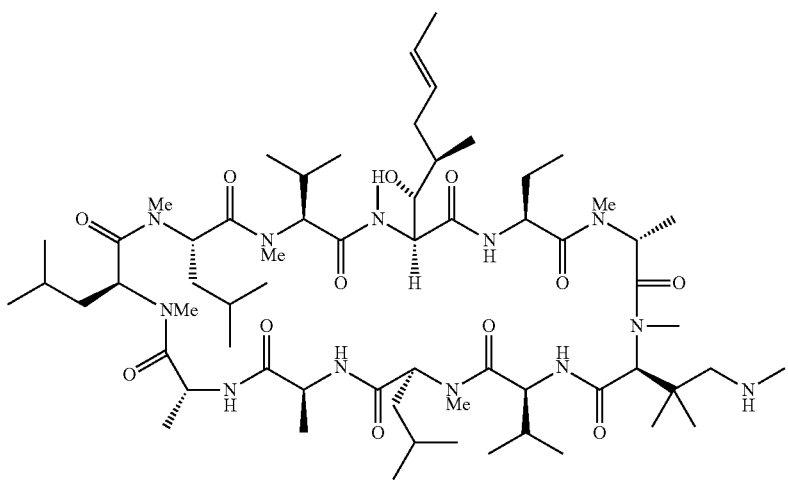

Example 1

To a mixture of 11 (296 mg, 0.24 mmol) in dry 1,2-dichloroethylene (2.4 mL) was added acetic acid (110 μL, 1.92 mmol) and MeNH$_2$ (0.84 mL, 2.0 M in THF, 1.68 mmol), successively and stirred at room temperature for 15 min. Then, NaBH(OAc)$_3$ (204 mg, 0.96 mmol) was added to the reaction and stirred at room temperature for 3.5 hrs. The reaction was diluted with CH$_2$Cl$_2$, washed with sat. NaHCO$_3$ solution, brine and separated. The organic layer was dried over Na$_2$SO$_4$, filtered and concentrated to dryness. The residue was triturated with MTBE, filtered through a fritted funnel and concentrated to dryness. The residue was purified by SiO$_2$ column chromatography with 0~9.5% methanol in CH$_2$Cl$_2$ to provide the compound of example 1 (231.9 mg) as a white foam. MS: (ESI) m/z 1246.0 (M+H)$^+$, 1267.97 (M+Na)$^+$.

Example 2

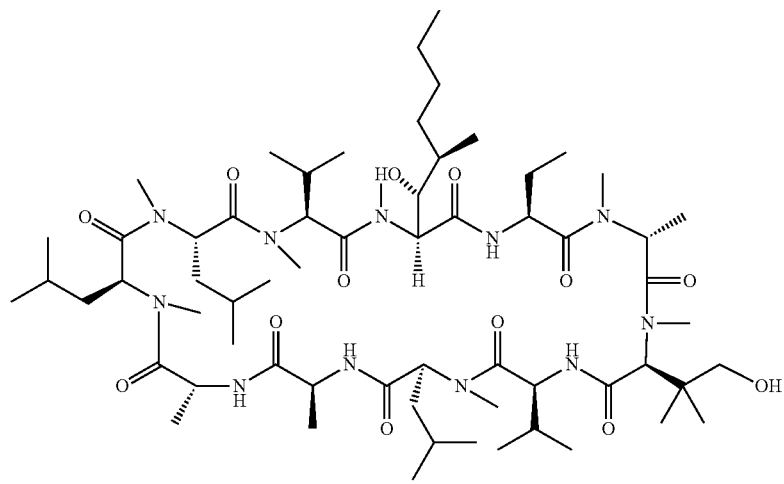

Step 2-1:

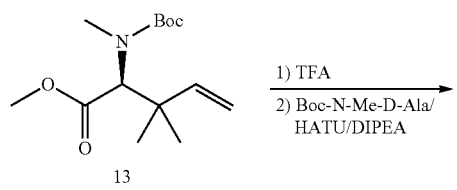

To a mixture of 1 (990 mg, 4.07 mmol) and iodomethane (1.77 mL, 28.48 mmol) in dry THF-DMF (2:1, 12 mL) was added sodium hydride (488 mg, 12.21 mmol, 60% in oil) at 0° C. and stirred for 15 min. Then, the reaction was allowed to warm to room temperature and stirred for 15 hrs. The reaction mixture was cooled to 0° C., quenched by addition of 3% citric acid (11 mL, pH~3) and extracted with MTBE (2 times). The combined organic layer was washed with H$_2$O (3 times) and brine. The organic layer was dried over Na$_2$SO$_4$, filtered, concentrated to dryness. The residue was purified by SiO$_2$ column chromatography with 0~14% ethyl acetate in hexanes to provide the compound 13 (1.075 g) as a colorless oil. MS: (ESI) m/z 172.14 (M-BOC+H)$^+$, 294.17 (M+Na)$^+$.

Step 2-2:

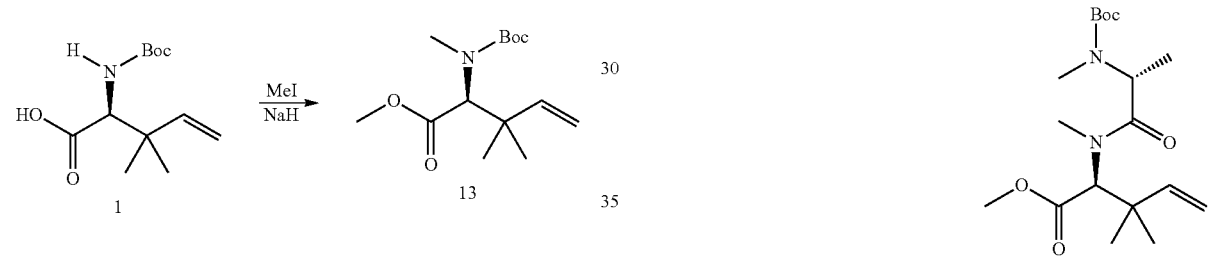

To a mixture of 13 (1.168 g, 4.3 mmol) in dry CH$_2$Cl$_2$ (8 mL) was dropwise added TFA (4 mL, 51.6 mmol) at 0° C. and stirred for 1.5 hr and diluted with CH$_2$Cl$_2$. The reaction was basified with saturated NaHCO$_3$ solution-20% aqueous K$_2$CO$_3$ solution (5:1, 8 volumes to TFA) and separated. The aqueous layer was extracted with CH$_2$Cl$_2$. The combined organic layer was washed with brine, dried over Na$_2$SO$_4$, filtered, concentrated to dryness. The residue was briefly dried on vacuum pump and used for the next reaction without further purification. Thus, deprotected amine and Boc-N-Me-D-ala (1.05 g, 5.16 mmol) were dissolved in dry CH$_2$Cl$_2$ (8.6 mL), treated with DIPEA (3 mL, 17.2 mmol) and HATU (2.45 g, 6.45 mmol) at room temperature and stirred for 7 hrs. The reaction was diluted with ethyl acetate, washed with 0.5N—HCl and separated. The aqueous layer was extracted with MTBE. The combined organic layer was washed with sat. NaHCO$_3$ solution and brine, separated, dried over Na$_2$SO$_4$, filtered and concentrated to dryness. The residue was purified by SiO$_2$ column chromatography with 0~25% ethyl acetate in hexanes to provide the compound 14 (569 mg) as a colorless oil, MS: (ESI) m/z 257.27 (M-BOC+H)$^+$, 379.34 (M+Na)$^+$.

Step 2-3:

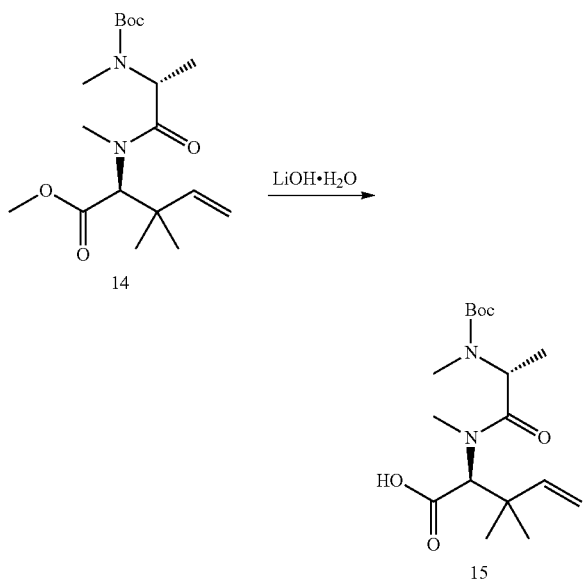

To a mixture of 14 in THF-MeOH (5:2, 14 mL) was added lithium hydroxide monohydrate (469 mg, 11.17 mmol) in $H_2O$ (4 mL) at 0° C. and stirred for 2 hrs, allowed to warm to room temperature and stirred for 2 hrs. Then, additional $H_2O$ (2 mL) was added to the reaction and stirred for 4.5 hrs. The reaction mixture was cooled to 0° C., diluted with $H_2O$ (20 mL), acidified with 1N—HCl (pH~3), extracted with $CH_2Cl_2$ (2 times). The combined organic layer was washed with sat. $NaHCO_3$ solution and brine, separated, dried over $Na_2SO_4$, filtered and concentrated to dryness. The residue was dried on vacuum pump, to provide the compound 15 (473 mg) as viscous oil and used for the next reaction without further purification. MS: (ESI) m/z 243.25 $(M-BOC+H)^+$, 365.33 $(M+Na)^+$.

Step 2-4:

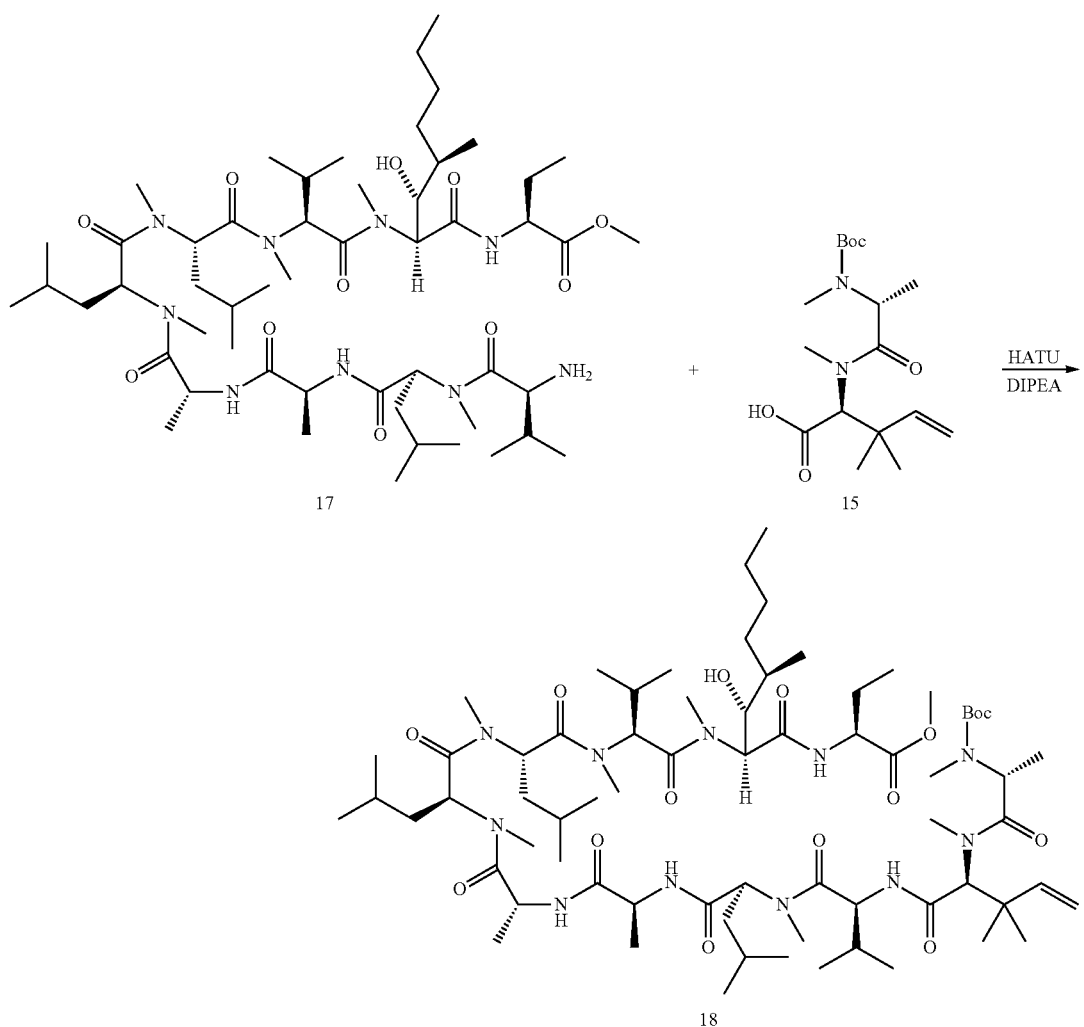

To a mixture of 15 (473 mg, 1.38 mmol) and 17 (1.363 g, 1.312 mmol) in dry $CH_2Cl_2$ (7 mL) was added DIPEA (0.607 mL, 5.53 mmol) and HATU (735 mg, 1.93 mmol) at 6° C. and stirred between 5 and 9° C. for 4 hrs. The reaction mixture was diluted with ethyl acetate, washed with sat. $NaHCO_3$ solution and separated. The aqueous layer was extracted with ethyl acetate. The combined organic layer was washed with sat. $NaHCO_3$ solution, dried over $Na_2SO_4$, filtered and concentrated to dryness. The residue was purified by $SiO_2$ column chromatography with 0~35% acetone in hexanes to provide the compound 18 (1,532 g) as a white foam, MS: (ESI) m/z 1363.52 $(M+H)^+$, 1385.49 $(M+Na)^+$.

Step 2-5:

To a mixture of 18 (1.532 g, 1.124 mmol) in THF-MeOH—$H_2O$ (5:2:2, 11.7 mL) was added lithium hydroxide monohydrate (141.4 mg, 3.37 mmol) at 0° C. and stirred at 0° C. for 1 hr. The reaction was diluted with $H_2O$ (20 mL), acidified with 1N—HCl (pH~2), extracted with ethyl acetate (2 times). The combined organic layer was washed with sat. $NaHCO_3$ solution and brine, separated, dried over $Na_2SO_4$, filtered and concentrated to dryness. The residue was dried on vacuum pump to provide the acid (1.493 g) as viscous oil and used for the next reaction without further purification. The acid (1.493 g) was dissolved in dry $CH_2Cl_2$ (15 mL), treated with TEA (7.65 mL, 89.9 mmol) at 0° C. and stirred for 1 hr. The reaction mixture was diluted with DCM, slowly

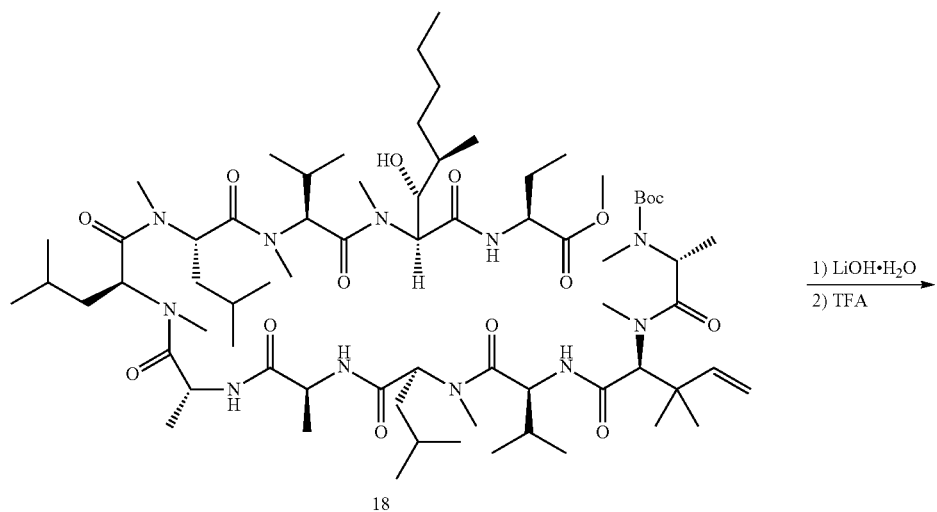

18

1) LiOH·$H_2O$
2) TFA

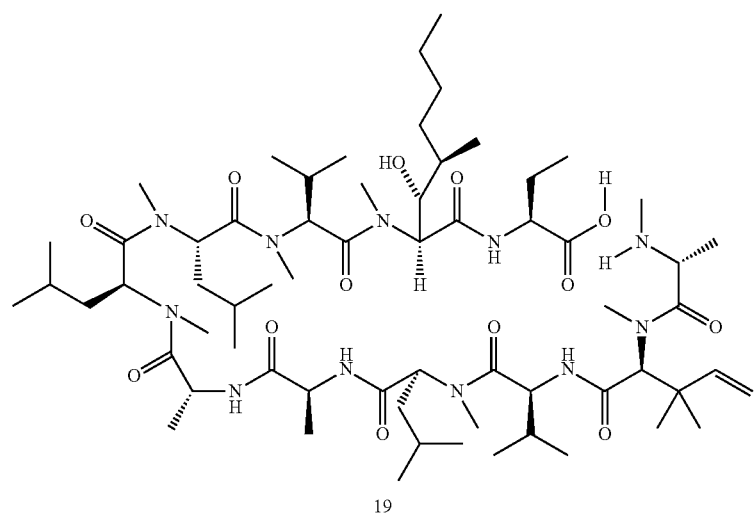

19 poured into ice-cold sat. NaHCO₃ solution-20% K₂CO₃ aq. solution (5:1, pH~8) and separated. The aqueous layer was extracted with CH₂Cl₂ (2 times). The combined organic layer was washed with brine, dried over Na₂SO₄, filtered and concentrated in vacuo, MS: (ESI) m/z 1249.19 (M+H)⁺, 1271.19 (M+Na)⁺. The residue was compound 19 and used for the next reaction without further purification.

Step 2-6:

To a mixture of HATU (461 mg, 1.213 mmol) and DMAP (162.7 mg, 1.213 mmol) in dry CH₂Cl₂ (40 mL) was dropwise added a solution of 19 (1.01 g, 0.809 mmol) in dry CH₂Cl₂ (100 mL) at 33° C. for 20 min. and stirred at 33° C. for 30 min. The reaction mixture was slowly allowed to cool to room temperature and stirred for 14 hrs. The reaction mixture was filtered through a fritted funnel and washed with sat. NaHCO₃ solution, brine and separated. The organic

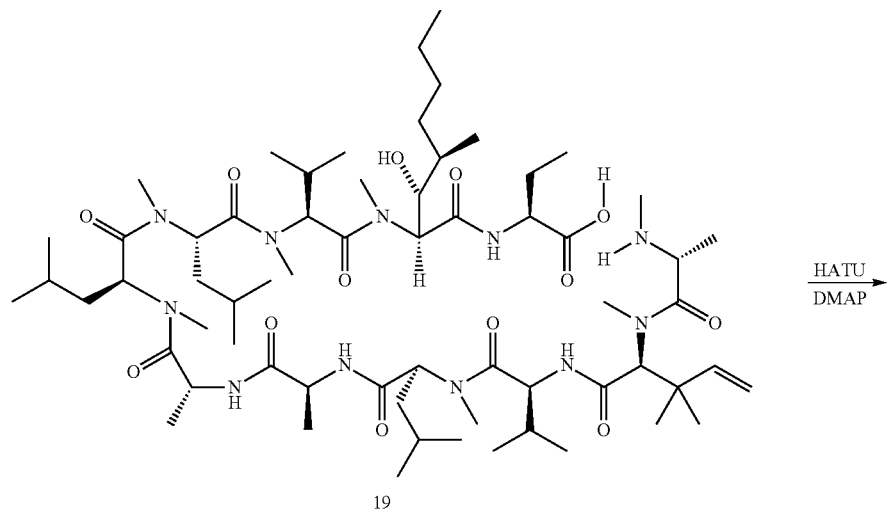

19

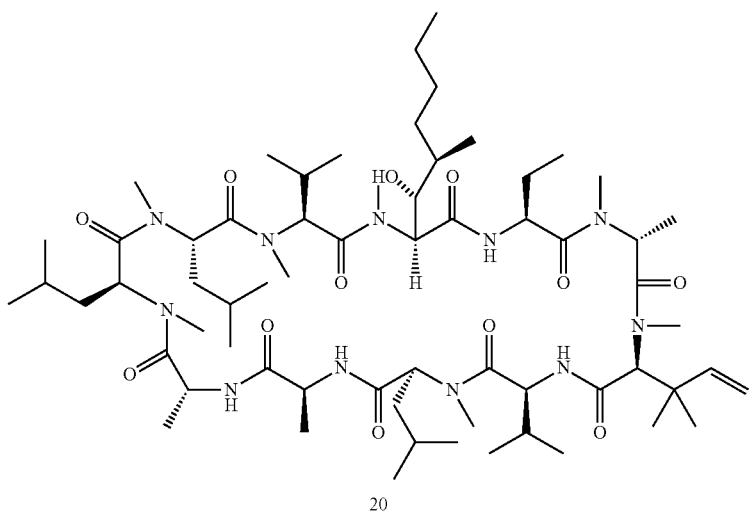

20 layer was dried over Na₂SO₄, filtered and concentrated to dryness. The residue was triturated with MTBE, filtered through a fritted funnel and concentrated to dryness. The residue was purified by SiO₂ column chromatography with 0~35% acetone iii hexane to provide the compound 20 (514 mg) as a white foam. MS: (ESI) m/z 1231.02 (M+H)⁺, 1253.01 (M+Na)⁺.

Step 2-7:

To a mixture of 20 (115 mg, 0.093 mmol) in dry MeOH (10 mL) was passed through ozone at −78° C. until the pale blue color persisted. Subsequently, oxygen and nitrogen passed through the solution. Then, dimethyl sulfide (48 µL, 0.65 mmol) was added to the reaction, slowly allowed to warm to room temperature and stirred for 16 hrs. The reaction was evaporated off, dissolved in t-BuOH-MeOH (4:1, 2 mL), cooled to 4° C., treated with sodium borohy-

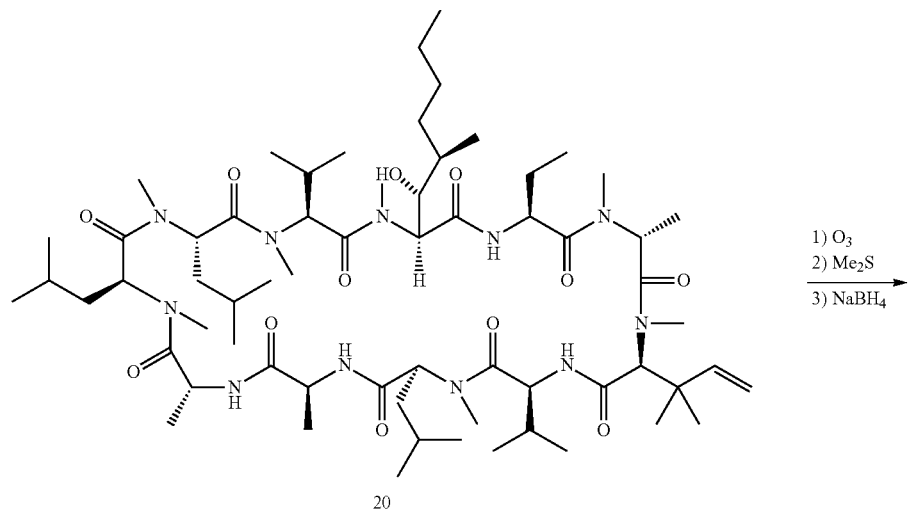

20

1) O₃
2) Me₂S
3) NaBH₄

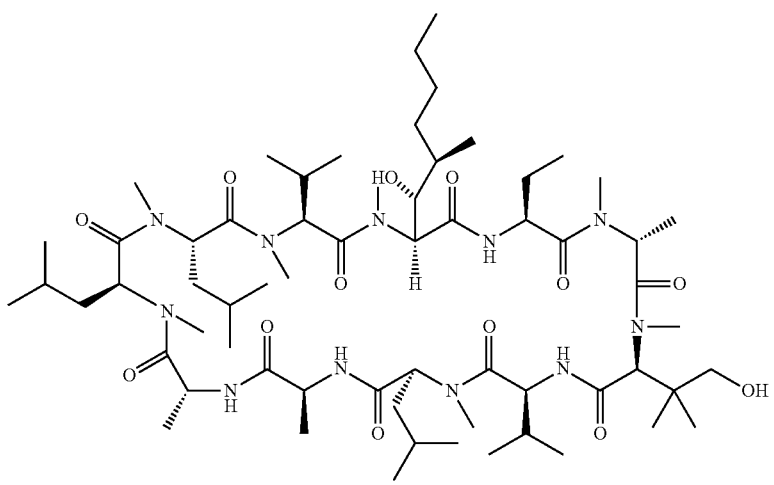

Example 2 dride (9 mg, 0.24 mmol) and stirred at 4° C. for 1 hr. The reaction was quenched by addition of sat. NH₄Cl solution, extracted with ethyl acetate. The organic layer was dried over Na₂SO₄, filtered, concentrated to dryness. A half of the residue was purified by preparative HPLC (HPLC condition: mobile phase A-20 mM NH₄HCO₃ in H₂O (HPLC grade); mobile phase B: Acetonitrile (HPLC grade); Luna column (pre-heated at 55° C.), flow rate: 20 mL/min; 60-90% B for 30 min.) to give the compound of example 2 (20 mg) as a white cotton after lyophilization. MS: (ESI) m/z 1235.34 (M+H)⁺, 1257.30 (M+Na)⁺.

Example 3

To example 2 (20 mg, 0.0161 mmol) in dry acetonitrile (0.3 mL) was added CDI (5.2 mg, 0.032 mmol) at room temperature and stirred for 19 hrs. After the reaction was completed, the reaction mixture was divided into 2 portions and concentrated, respectively. One portion was dissolved in 2M-MeNH₂ in THF (0.5 mL) and stirred at room temperature for 24 hrs. After concentration, the residue was purified by preparative HPLC (HPLC condition: mobile phase A-20 mM NH₄HCO₃ in H₂O (HPLC grade); mobile phase B: Acetonitrile (HPLC grade); semi-prep L-column (pre-heated at 55° C.), flow rate: 5 mL/min; 60-90% B for 30 min.) to give the compound of example 3 (10 mg) as a white cotton after lyophilization. MS: (ESI) m/z 1291.94 (M+H)⁺, 1314.05 (M+Na)⁺.

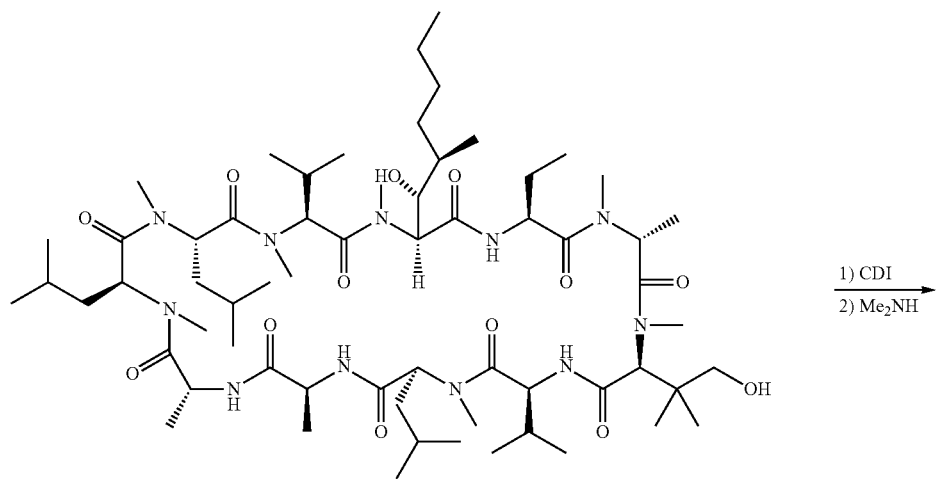

Example 2

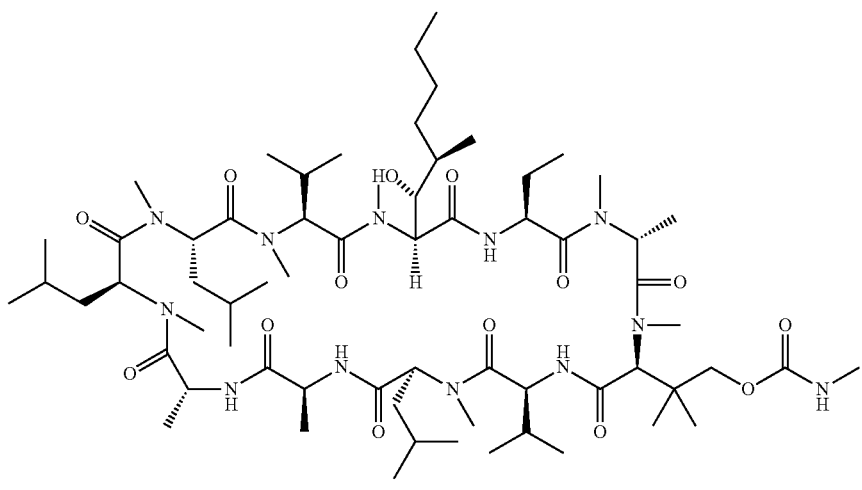

Example 3

Example 4

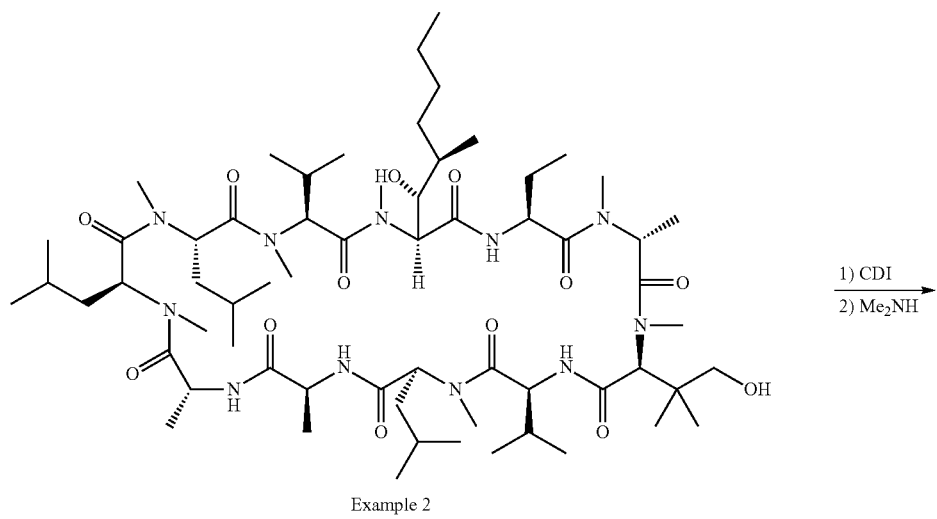

Example 2

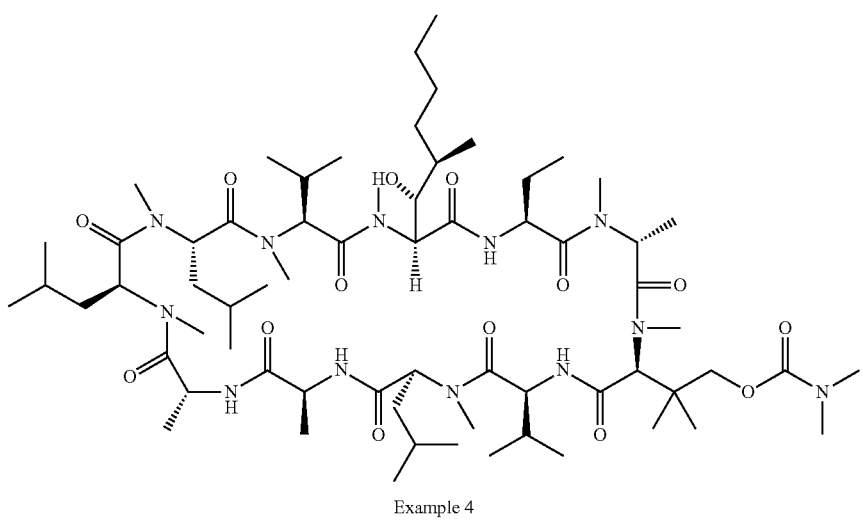

Example 4

The other portion was dissolved in 2M-Me$_2$NH in THF (0.5 mL) and stirred at room temperature for 24 hrs. After concentration, the residue was purified by preparative HPLC (HPLC condition: mobile phase A-20 mM NH$_4$HCO$_3$ in H$_2$O (HPLC grade); mobile phase B: Acetonitrile (HPLC grade); semi-pre L-column (pre-heated at 55° C.), flow rate: 5 mL/min; 70-90% B for 30 min.) to give the compound of example 4 (10 mg) as a white cotton after lyophilization. MS: (ESI) m/z 1305.95 (M+H)$^+$, 1328.05 (M+Na)$^+$.

Intermediate 3

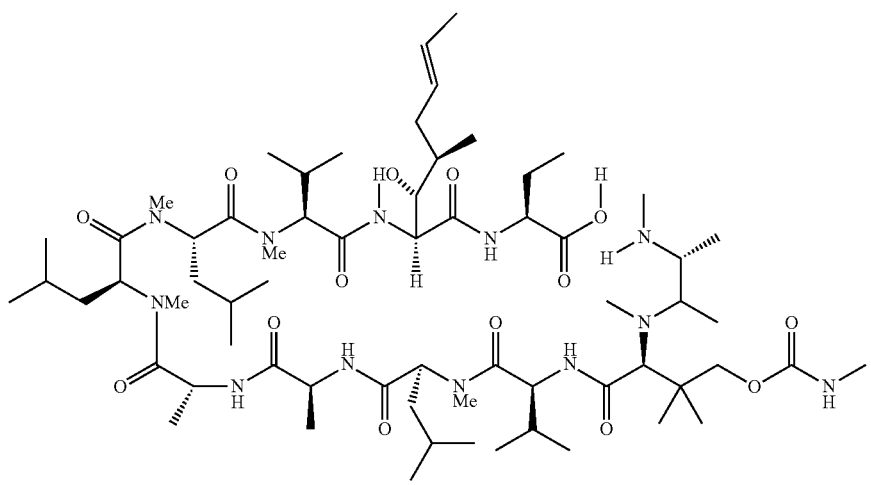

Step 3-1:

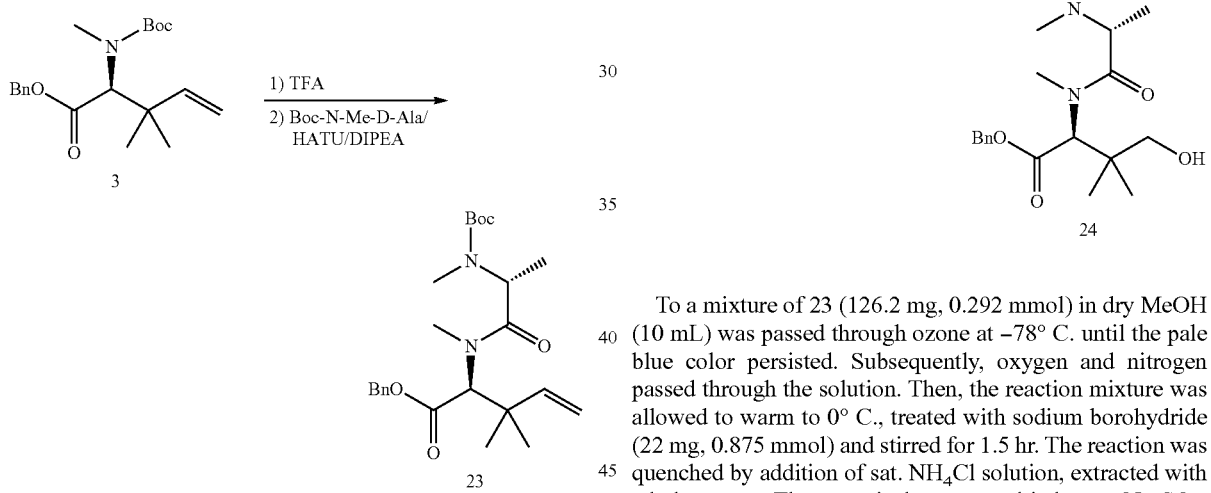

As described in the procedure for the intermediate 1, the compound 23 was synthesized from compound 3 (302 mg, 0.87 mmol) and Boc-N-Me-D-ala (530 mg, 2.61 mmol). MS: (ESI) m/z 433.07 (M+H)+, 455.32 (M+Na)−.

Step 3-2:

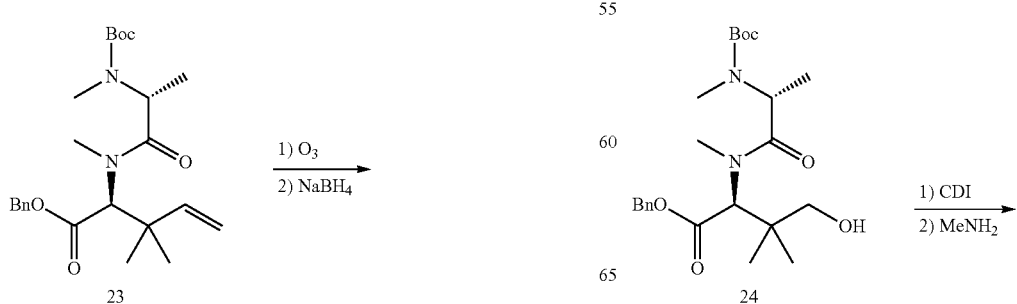

To a mixture of 23 (126.2 mg, 0.292 mmol) in dry MeOH (10 mL) was passed through ozone at −78° C. until the pale blue color persisted. Subsequently, oxygen and nitrogen passed through the solution. Then, the reaction mixture was allowed to warm to 0° C., treated with sodium borohydride (22 mg, 0.875 mmol) and stirred for 1.5 hr. The reaction was quenched by addition of sat. NH4Cl solution, extracted with ethyl acetate. The organic layer was dried over Na2SO4, filtered, concentrated to dryness. The residue was purified by SiO2 column chromatography with 0~20% acetone ire hexanes to provide the compound 24 (41.5 mg) as a white foam. MS: (ESI) m/z 437.16 (M+H)+.

Step 3-3:

65
-continued
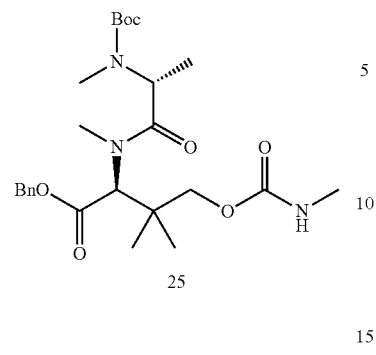
As described in the procedure for the synthesis of step 2-9, the compound 25 was synthesized from 24 (41.5 mg, 0.095 mmol). MS: (ESI) m/z 494.11 (M+H)⁺, 516.37 (M+Na)⁺.
Step 3-4:
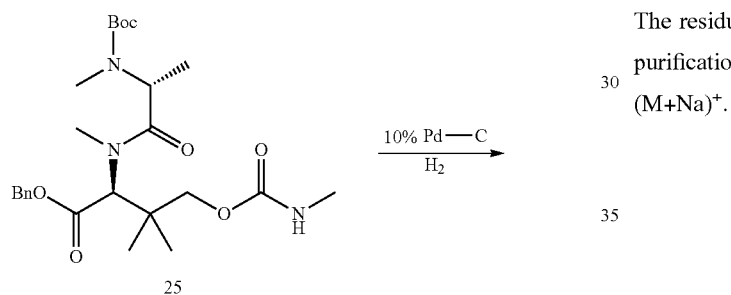
66
-continued
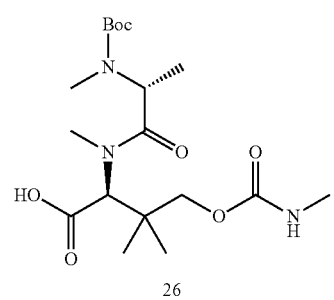
As described in the procedure of the step 1-5, the compound 26 was synthesized from 25 (97.7 mg, 0.198 mmol). The residue was used for the next reaction without further purification. MS: (ESI) m/z 404.06 (M+H)⁺, 426.30 (M+Na)⁺.
Step 3-5:
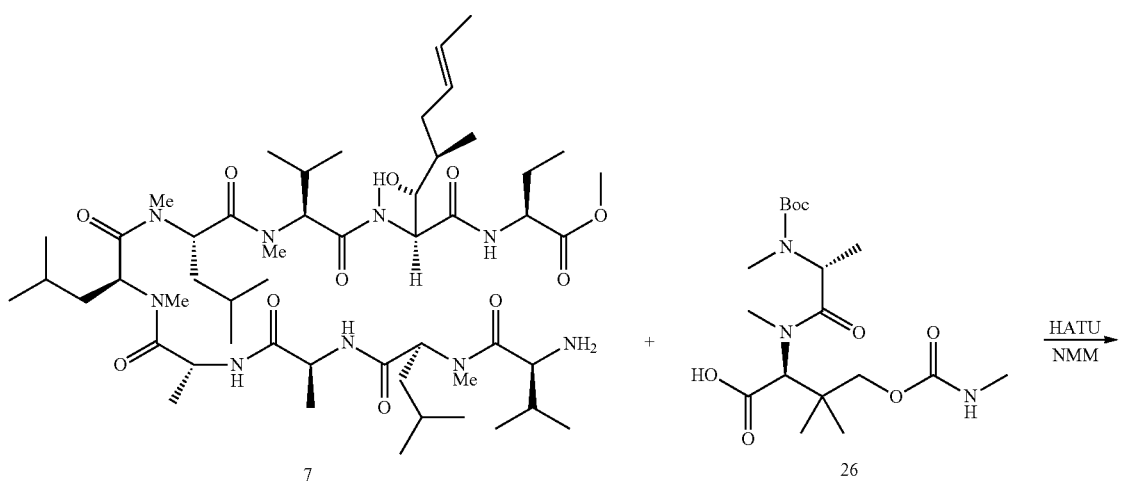

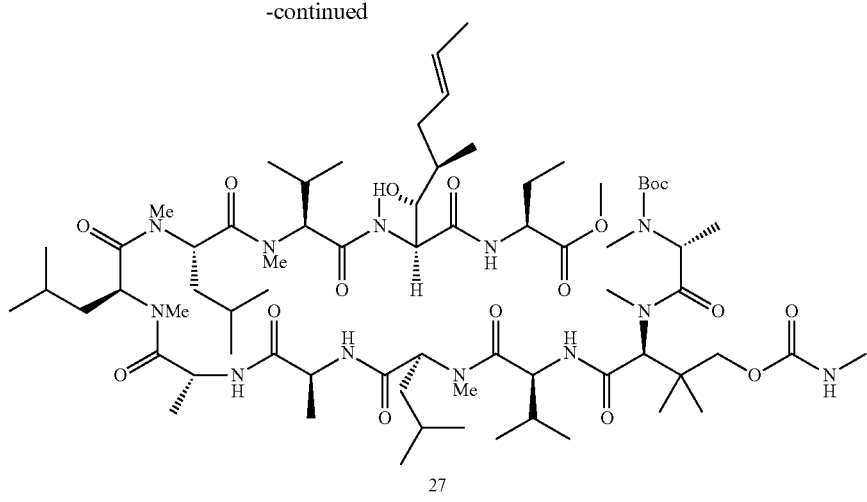

To a mixture of 26 (0.2 mmol) and 7 (194.8 mg, 0.19 mmol) in dry CH$_2$Cl$_2$ (2 mL) was added N-methylmorpholine (65.2 μL, 0.59 mmol) and HATU (97.8 mg, 0.26 mmol) at 3.5° C. and stirred between 3.5 and 12° C. for 3 hrs. The reaction mixture was diluted with ethyl acetate, washed with sat. NaHCO$_3$ solution and separated. The aqueous layer was extracted with ethyl acetate. The combined organic layer was washed with sat. NaHCO$_3$ solution, dried over Na$_2$SO$_4$, filtered and concentrated to dryness. The residue was purified by SiO$_2$ column chromatography with 0~5% methanol in CH$_2$Cl$_2$ to provide the compound 27 (200.2 mg) as a white foam. MS: (ESI) m/z 1443.88 (M+Na)$^+$.

Step 3-6:

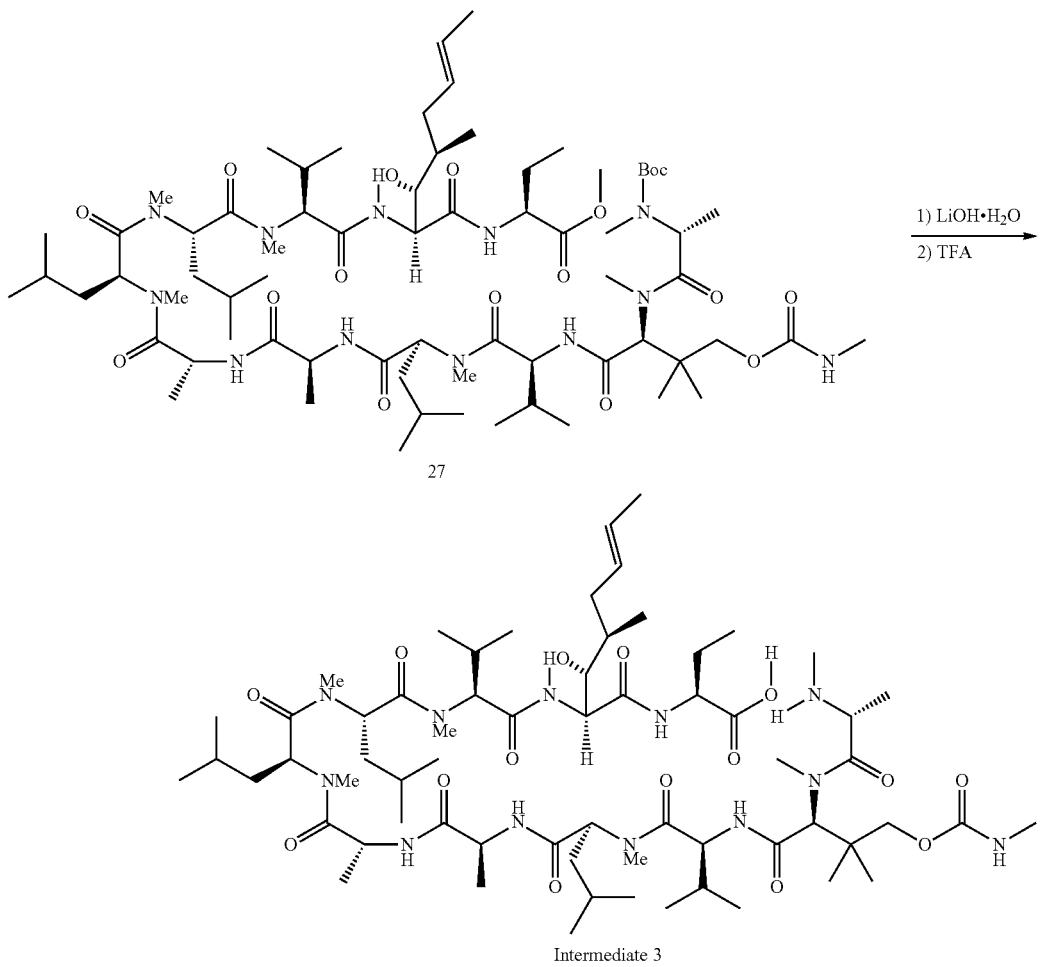

As described in the procedure of the step 2-5, intermediate 3 was synthesized from compound 27 (200 mg, 0.14 mmol).
MS: (ESI) m/z 1307.76 (M+H)⁺, 1329.95 (M+Na)⁺.
Example 5
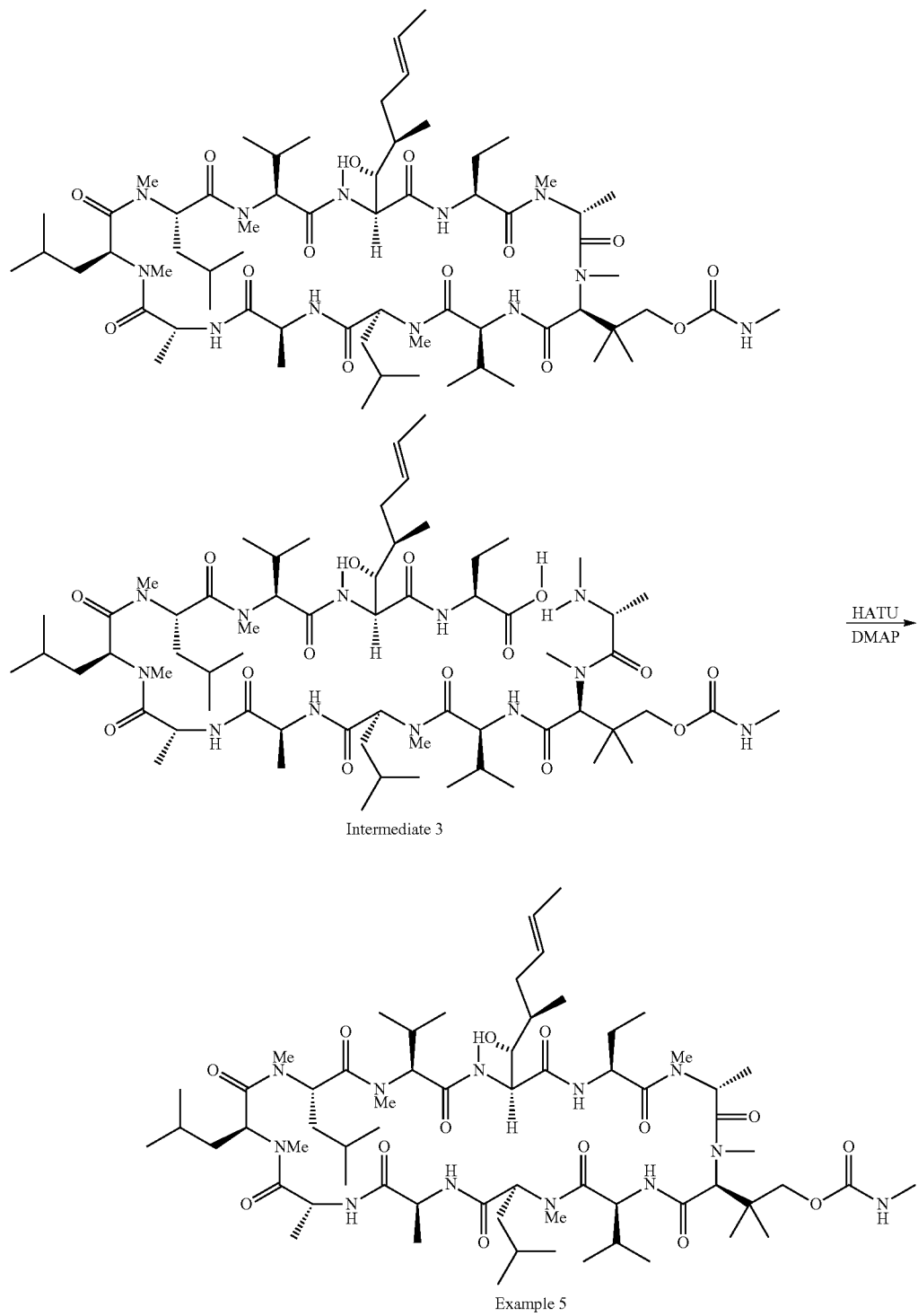
Intermediate 3
Example 5
As described in the procedure of the step 2-6, the example 5 was synthesized from intermediate 5 (0.14 mmol). MS: (ESI) m/z 1289.80 (M+H)⁺, 1311.91 (M+Na)⁺.

71
Intermediate 4
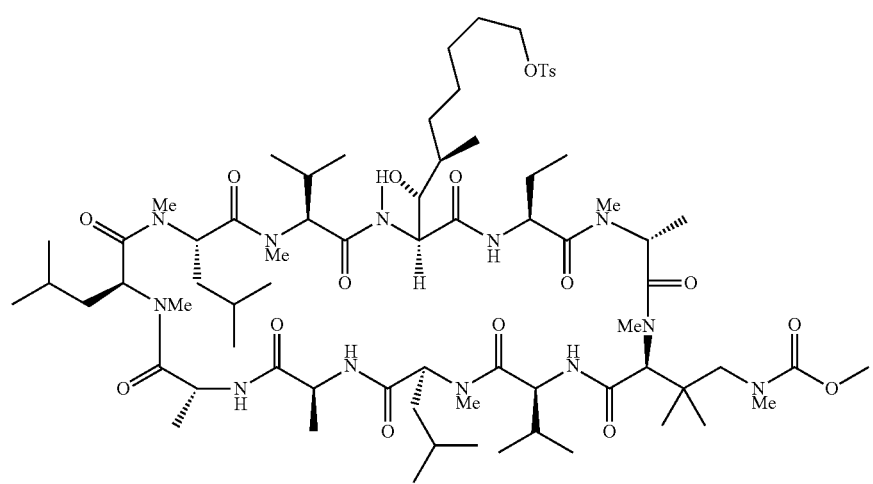
Step 4-1:
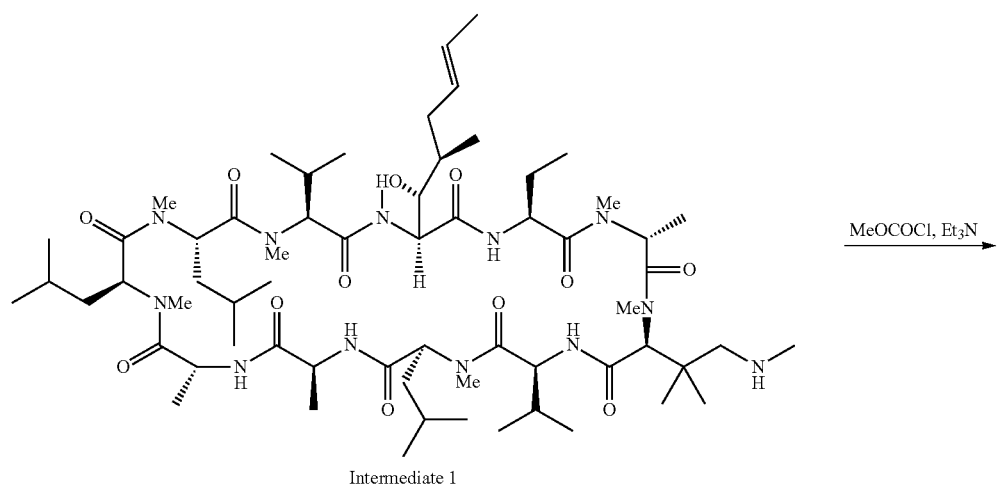
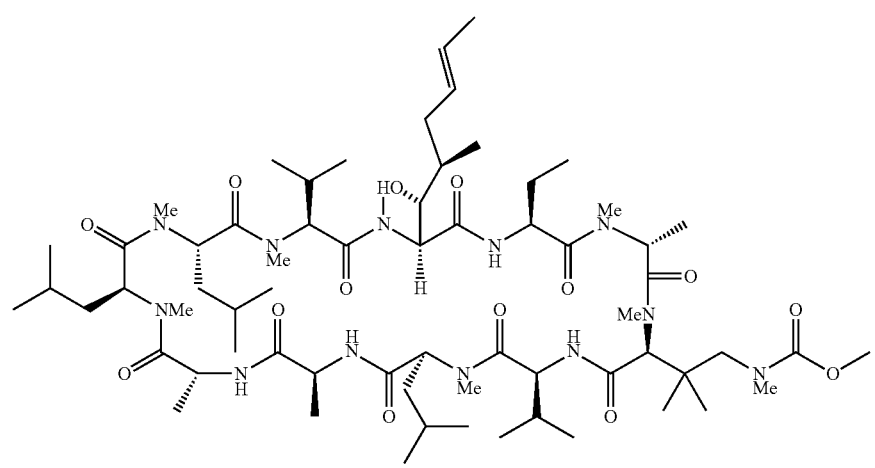

To a mixture of intermediate 1 (503 mg, 0.404 mmol) and triethylamine (169 μL, 3 eq.) in dry $CH_2Cl_2$ (2 mL) was added methyl chloroformate (93.8 μL, 3 eq.) at room temperature, and stirred for 16 hrs. The reaction was diluted with $CH_2Cl_2$, and washed with saturated aqueous $NaHCO_3$ solution and brine, successively. The organic layer was dried over $Na_2SO_4$, filtered and evaporated to dryness. The residue was purified by silica gel column chromatography with 0~50% acetone in hexanes to give the compound 28 (469 mg) as a white foam. MS: (ESI) m/z 1304.09 $(M+H)^+$, 1326.15 $(M+Na)^+$.

Step 4-2:

A mixture of 28 (392.9 mg, 0.301 mmol) and 29 (1.54 g, 12 eq.) in dry toluene (3.54 mL) was stirred at 60° C. for 1.5 hrs in the presence of Zhan-1B catalyst (11 mg, 5 mol %). The reaction mixture was then treated with 2-mercaptonicotinic acid (16.4 mg, 0.35 eq.) and DIPEA (18.8 μL, 0.36 eq.), and stirred at 60° C. for 30 min. The reaction mixture was diluted with ethyl acetate, and washed with saturated aqueous $NaHCO_3$ solution and brine, successively. The organic layer was dried over $Na_2SO_4$, filtered and evaporated to dryness. The residue was purified by silica gel column chromatography with 0~50% acetone in hexanes to give the compound 30 (389 mg) as a mixture of (E/Z)-isomers. MS: (ESI) m/z 1488.08 $(M+H)^+$, 1510.07 $(M+Na)^+$.

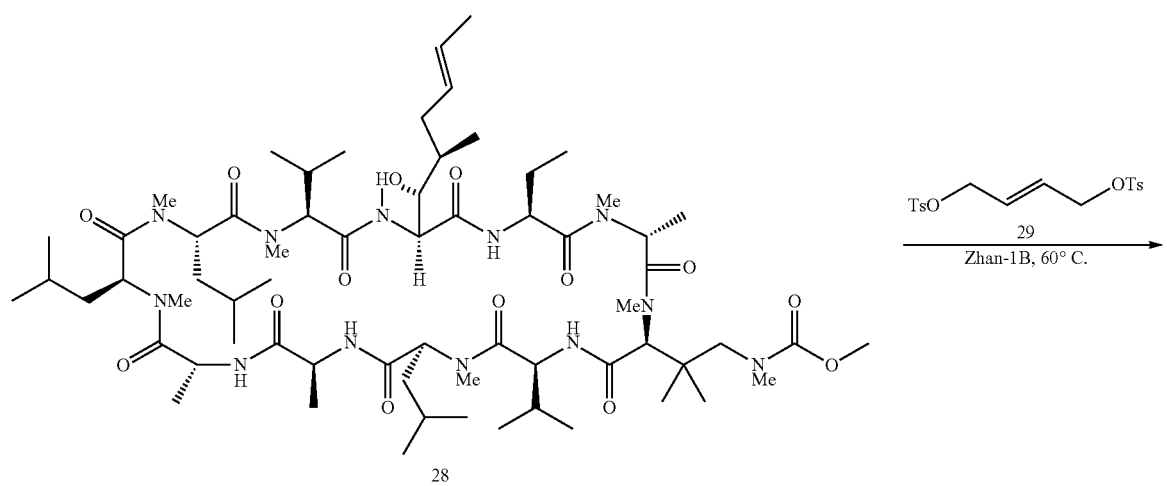

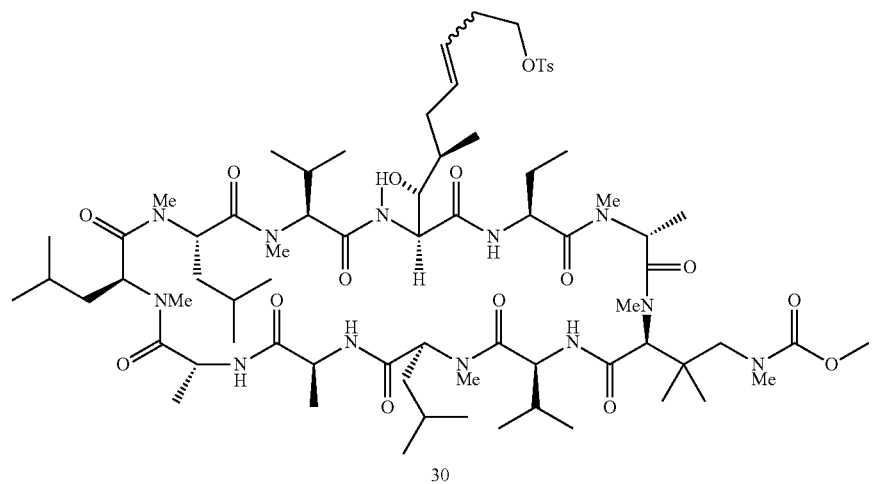

Step 4-3:
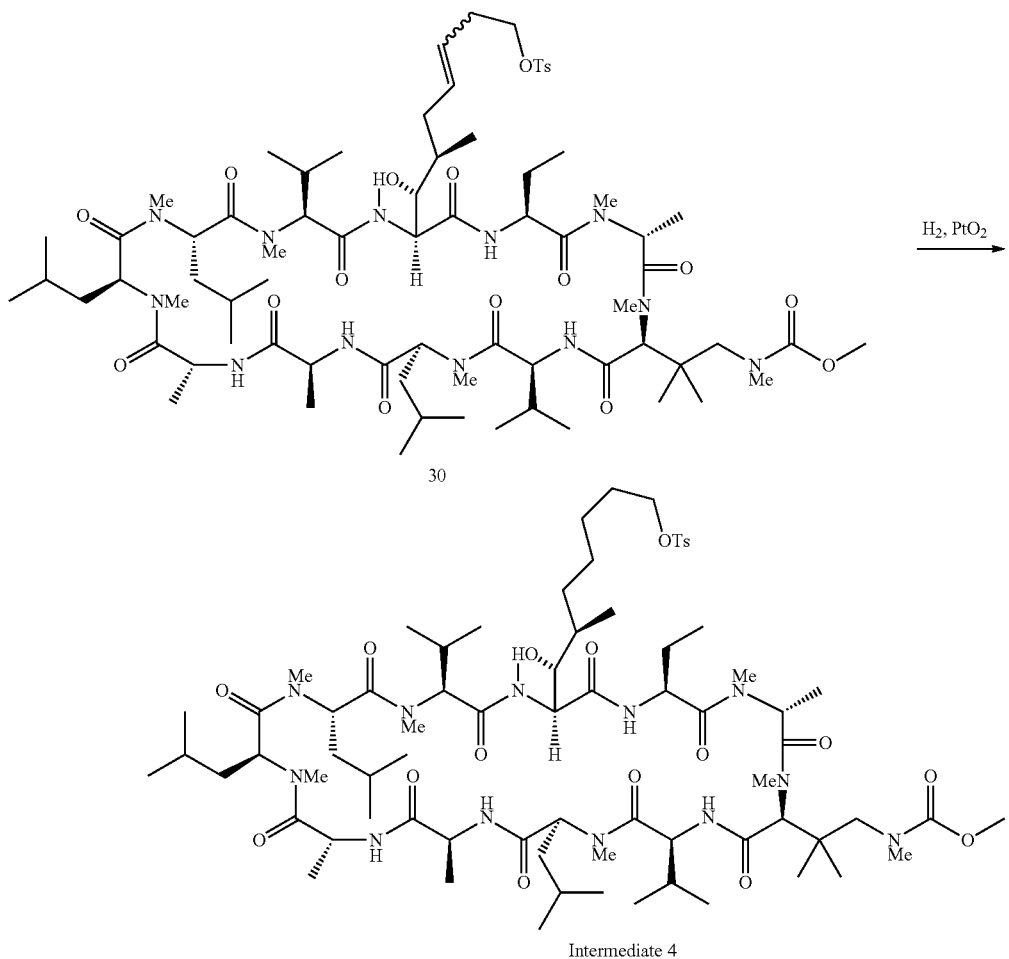
A solution of 30 (82 mg, 0.0551 mmol) in ethyl acetate (656 μL) was stirred under H₂ (1 atm) in the presence of PtO₂ (6.6 mg) at room temperature for 13.5 hrs. The reaction mixture was filtered through CELITE®, and evaporated to dryness. The crude product, intermediate 4, (87 mg) was used for the next step without purification. MS: (ESI) m/z 1490.11 (M+H)⁺, 1512.09 (M+Na)⁺.
Example 6
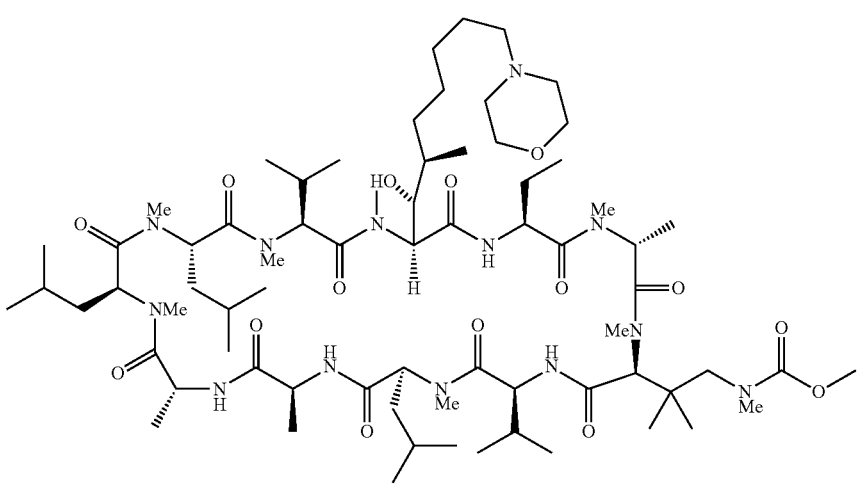

-continued

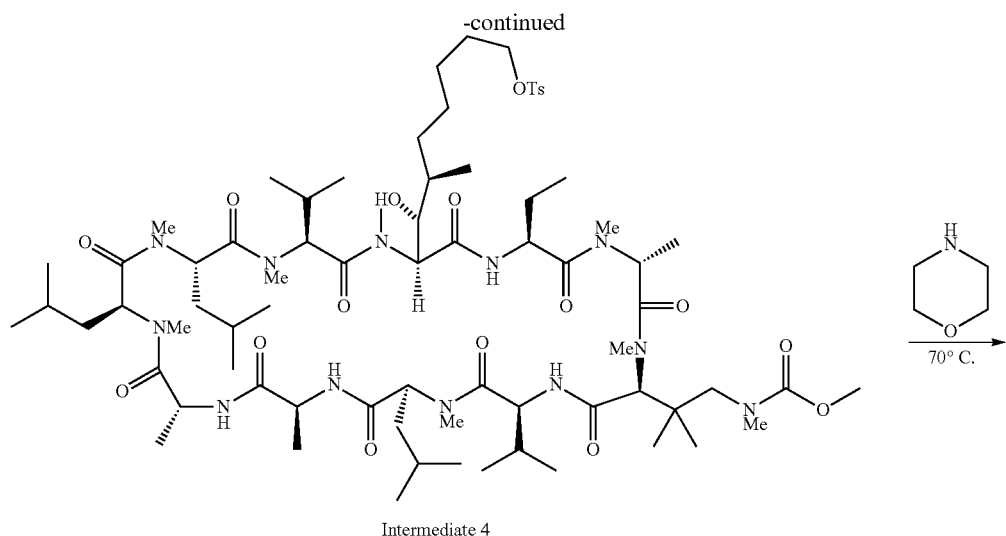

Intermediate 4

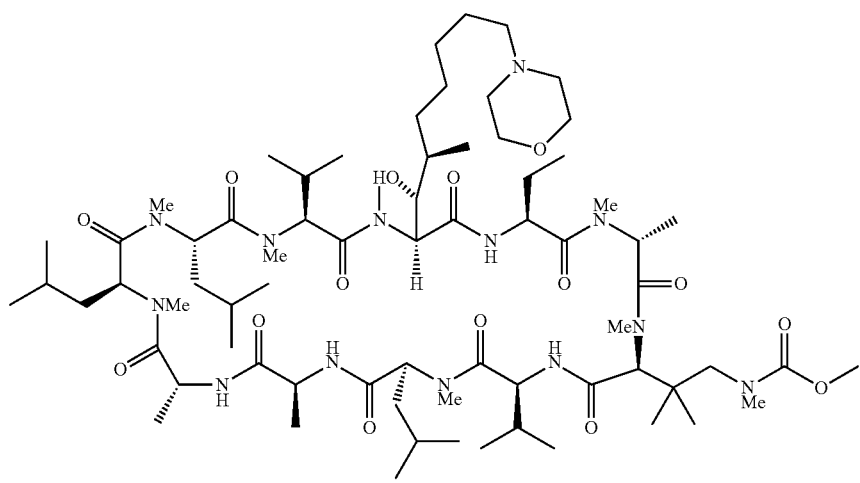

Example 6

To a solution of crude intermediate 4 (87 mg, 0.0584 mmol.) in dry dimethylformamide (325 μL) was added morpholine (25.2 μL, 5 eq.), and stirred at 70° C. for 3.5 hrs. The reaction mixture was concentrated, and purified by preparative HPLC (HPLC condition: mobile phase A-20 mM $NH_4HCO_3$ in $H_2O$ (HPLC grade); mobile phase B: Acetonitrile (HPLC grade); Luna column (pre-heated at 55° C.), flow rate: 20 mL/min; 55-90% B for 30 min.) to give the pure example 6 (48.9 mg) as a white cotton after lyophilization. MS: (ESI) m/z 1405.18 (M+H)$^+$, 1427.09 (M+Na)$^+$.

Example 7
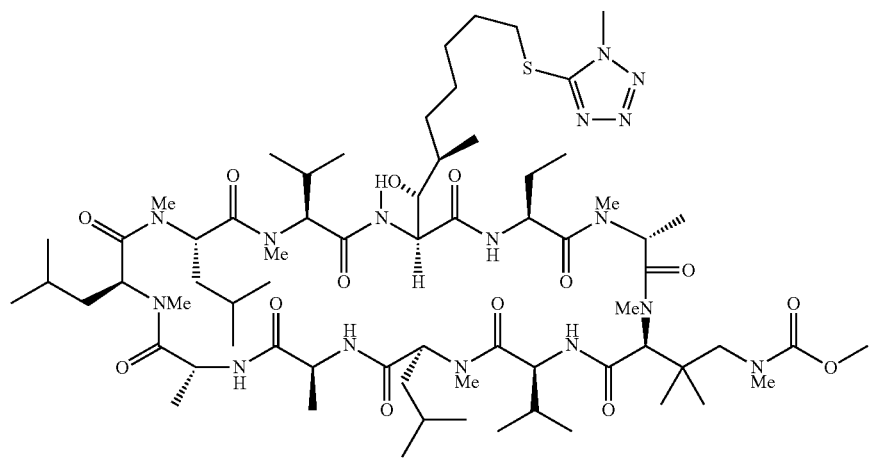
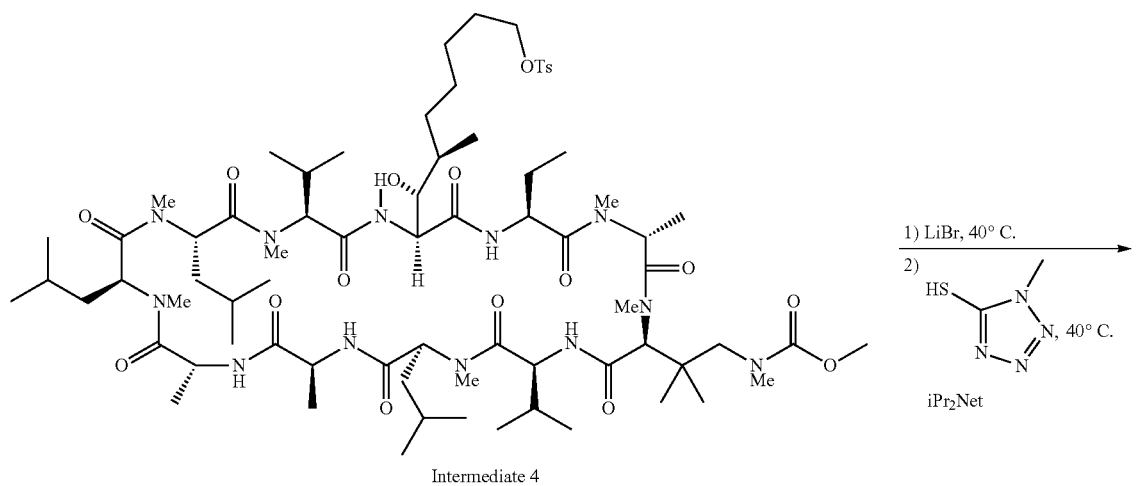
Intermediate 4
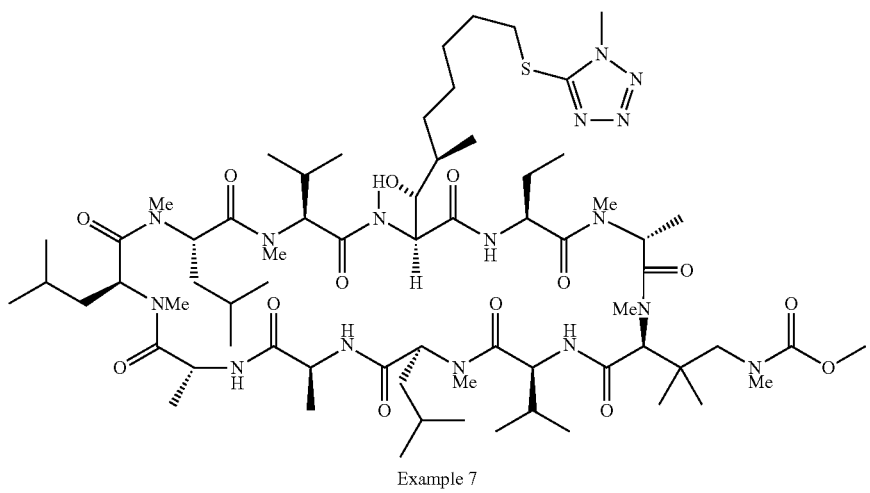
Example 7

To a solution of crude intermediate 4 (83.7 mg, 0.0562 mmol) in acetone (281 μL) was added LiBr (19.5 mg, 4 eq.) at 0° C., and stirred at 40° C. for 4 hrs. The reaction was diluted with MTBE, and washed with H₂O and brine, successively. The organic layer was dried over Na₂SO₄, filtered and evaporated to dryness. The crude bromide was used for the next step without purification.

To a mixture of crude bromide and 5-mercapto-1-methyltetrazole (26.1 mg, 4 eq.) in dry dioxane (281 μL) was added DIPEA (48.9 μL, 5 eq.), and stirred at 40° C. for 5.5 hrs. The reaction was diluted with MTBE, and washed with saturated aqueous NaHCO₃ solution and brine, successively. The organic layer was dried over Na₂SO₄, filtered and evaporated to dryness. The residue was purified by preparative HPLC (HPLC condition: mobile phase A-20 mM NH₄HCO₃ in H₂O (HPLC grade); mobile phase B: Acetonitrile (HPLC grade); Luna column (pre-heated at 55° C.), flow rate: 20 mL/min; 55-90% B for 30 min.) to give the pure example 7 (51.7 mg) as a white cotton after lyophilization. MS: (ESI) m/z 1434.16 (M+H)⁺, 1456.13 (M+Na)⁺.

Intermediate 5

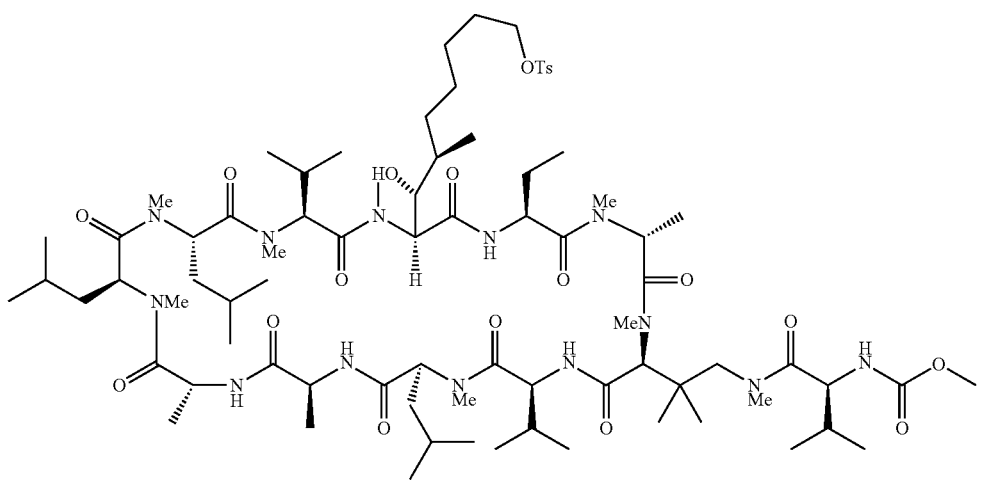

Step 5-1:

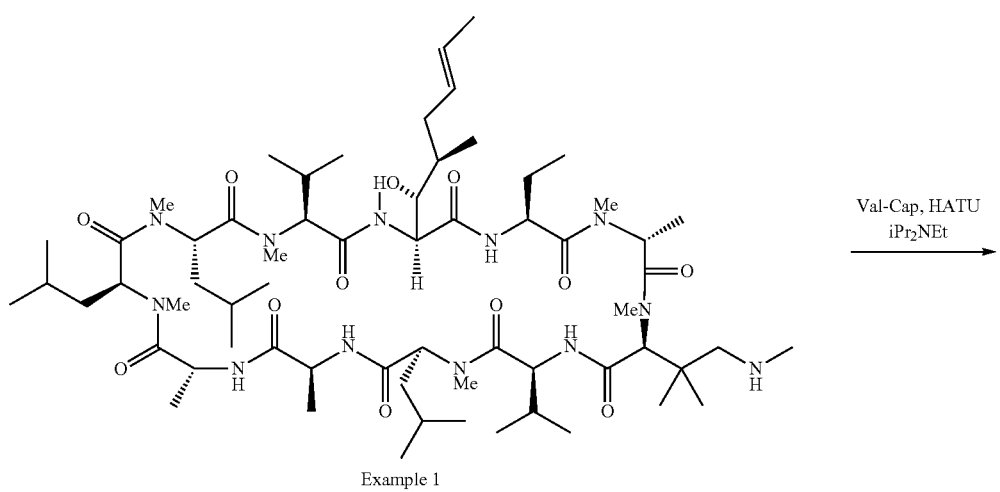

Example 1

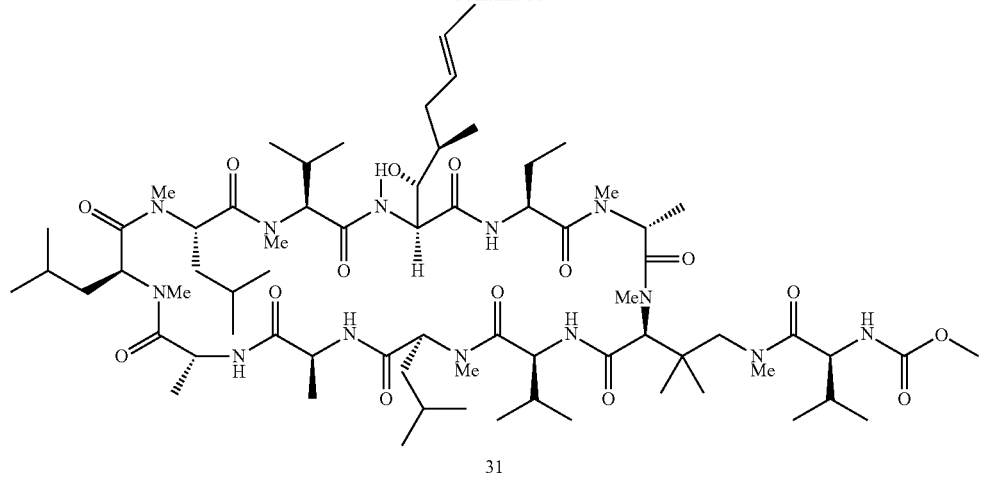

31

To a mixture of example 1 (500 mg, 0.401 mmol), val-Cap (211 mg, 3 eq.) and DIPEA (418 μL, 6 eq.) in dry CH₂Cl₂ (2 mL) was added HATU (533 mg, 3.5 eq.) at room temperature, and stirred for 16 hrs. The reaction was diluted with CH₂Cl₂, and washed with saturated aqueous NaHCO₃ solution and brine, successively. The organic layer was dried over Na₂SO₄, filtered and evaporated to dryness. The residue was purified by silica gel column chromatography with 0~40% acetone in hexanes to give the compound 31 (457 mg) as a white foam. MS: (ESI) m/z 1403.20 (M+H)⁺, 1425.20 (M+Na)⁺.

Step 5-2:

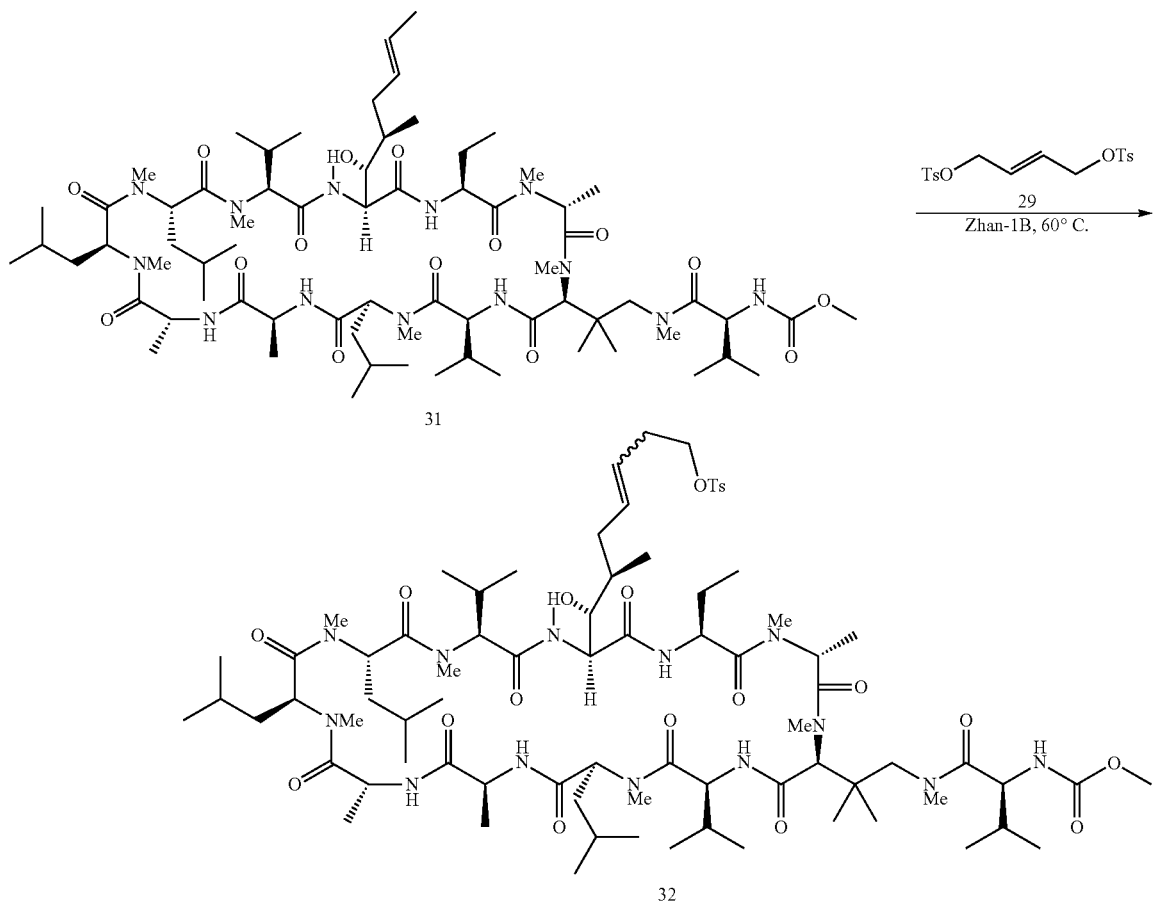

A mixture of 31 (328 mg, 0.234 mmol) and 29 (1.19 g, 12 eq.) in dry toluene (2.9 mL) was stirred at 60° C. for 75 min. in the presence of Zhan-1B catalyst (8.6 mg, 5 mol %). The reaction mixture was then treated with 2-mercaptonicotinic acid (12.8 mg, 0.35 eq.) and DIPEA (14.2 µL, 0.35 eq.), and stirred at 60° C. for 30 min. The reaction mixture was diluted with ethyl acetate, and washed with saturated aqueous NaHCO₃ solution and brine, successively. The organic layer was dried over Na₂SO₄, filtered and evaporated to dryness. The residue was purified by silica gel column chromatography with 0~50% acetone in hexanes to give the compound 32 (405 mg) as a mixture of (E/Z)-isomers. MS: (ESI) m/z 1587.07 (M+H)⁺, 1609.06 (M+Na)⁺.

Step 5-3:

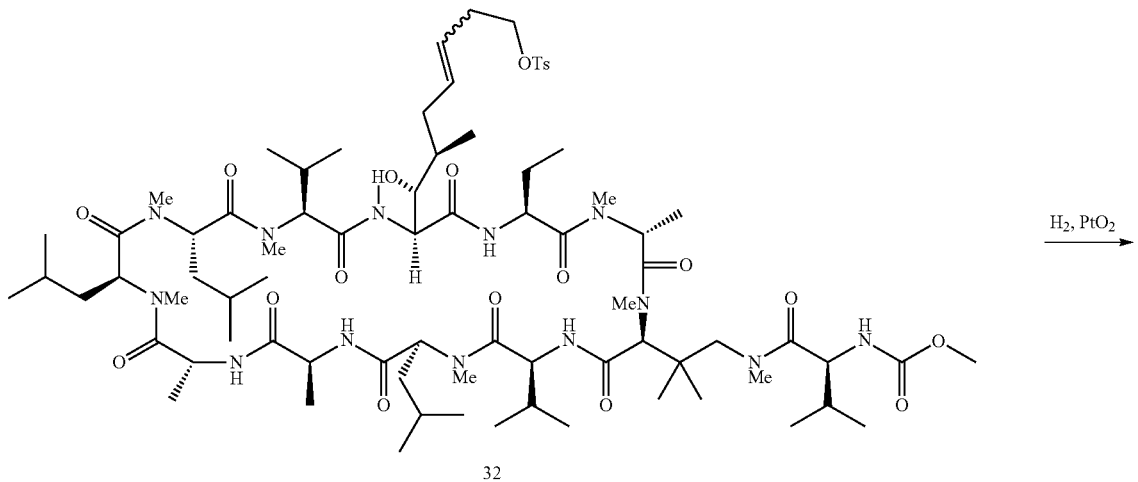

32

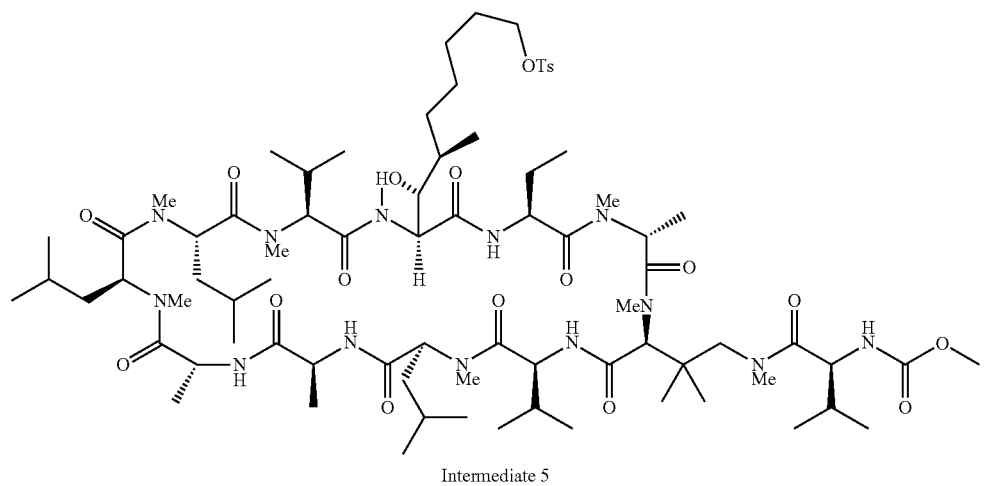

Intermediate 5

A solution of 32 (199 mg, 0.125 mmol) in ethyl acetate (1.59 mL) was stirred under H₂ (1 atm) in the presence of PtO₂ (15.9 mg) at room temperature for 10 hrs. The reaction mixture was filtered through CELITE®, and evaporated to dryness. The crude intermediate 5 (191 mg) was used for the next step without purification. MS: (ESI) m/z 1589.13 (M+H)⁺, 1611.12 (M+Na)⁺.

Example 8

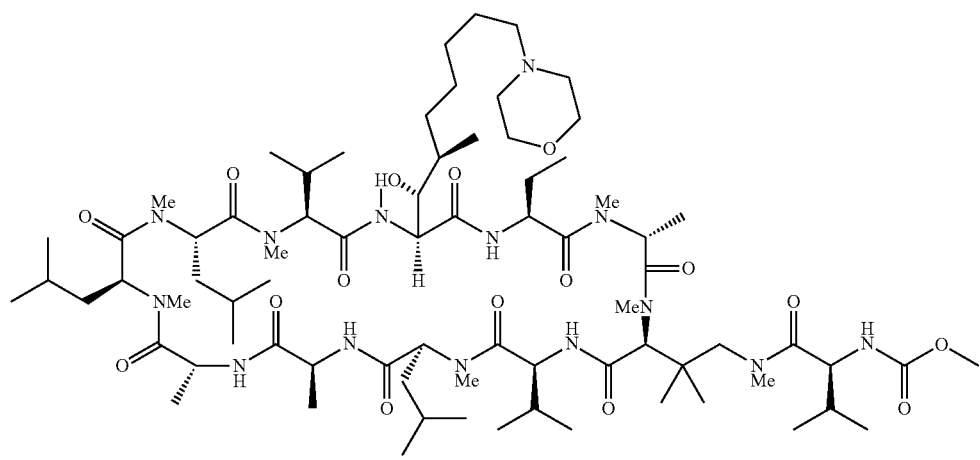

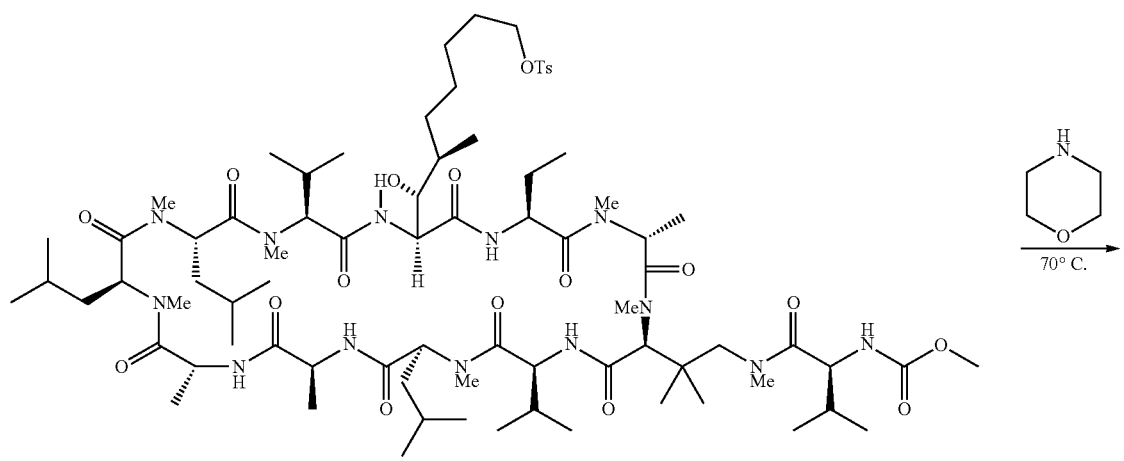

Intermediate 5

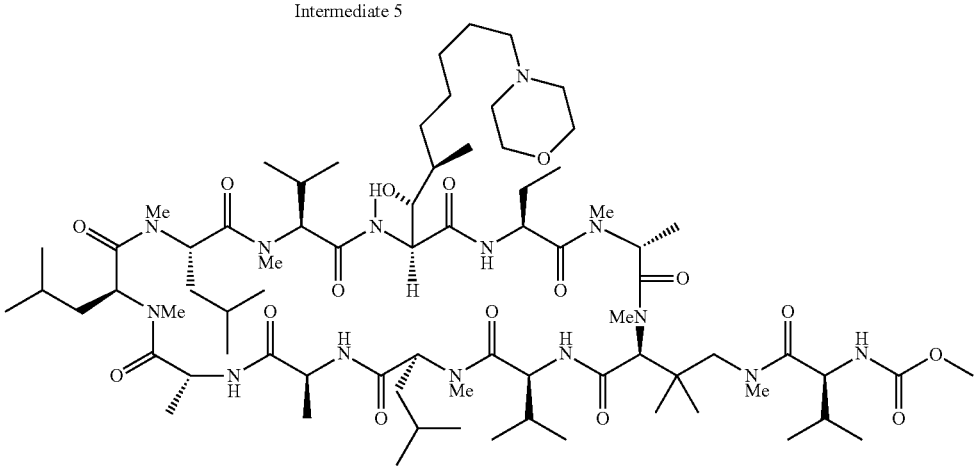

Intermediate 8

To a solution of crude intermediate 5 (129 mg, 0.0812 mmol.) in dry dimethylformamide (406 μL) was added morpholine (42 μL, 6 eq.), and stirred at 70° C. for 24 hrs. The reaction mixture was concentrated, and purified by preparative HPLC (HPLC condition: mobile phase A-20 mM NH$_4$HCO$_3$ in H$_2$O (HPLC grade); mobile phase B: Acetonitrile (HPLC grade); Luna column (pre-heated at 55° C.), flow rate: 20 mL/min; 55-90% B for 30 min.) to give the pure title example 8 (74 mg) as a white cotton after lyophilization. MS: (ESI) m/z 1504.25 (M+H)$^+$, 1526.23 (M+Na)$^+$.

Example 9
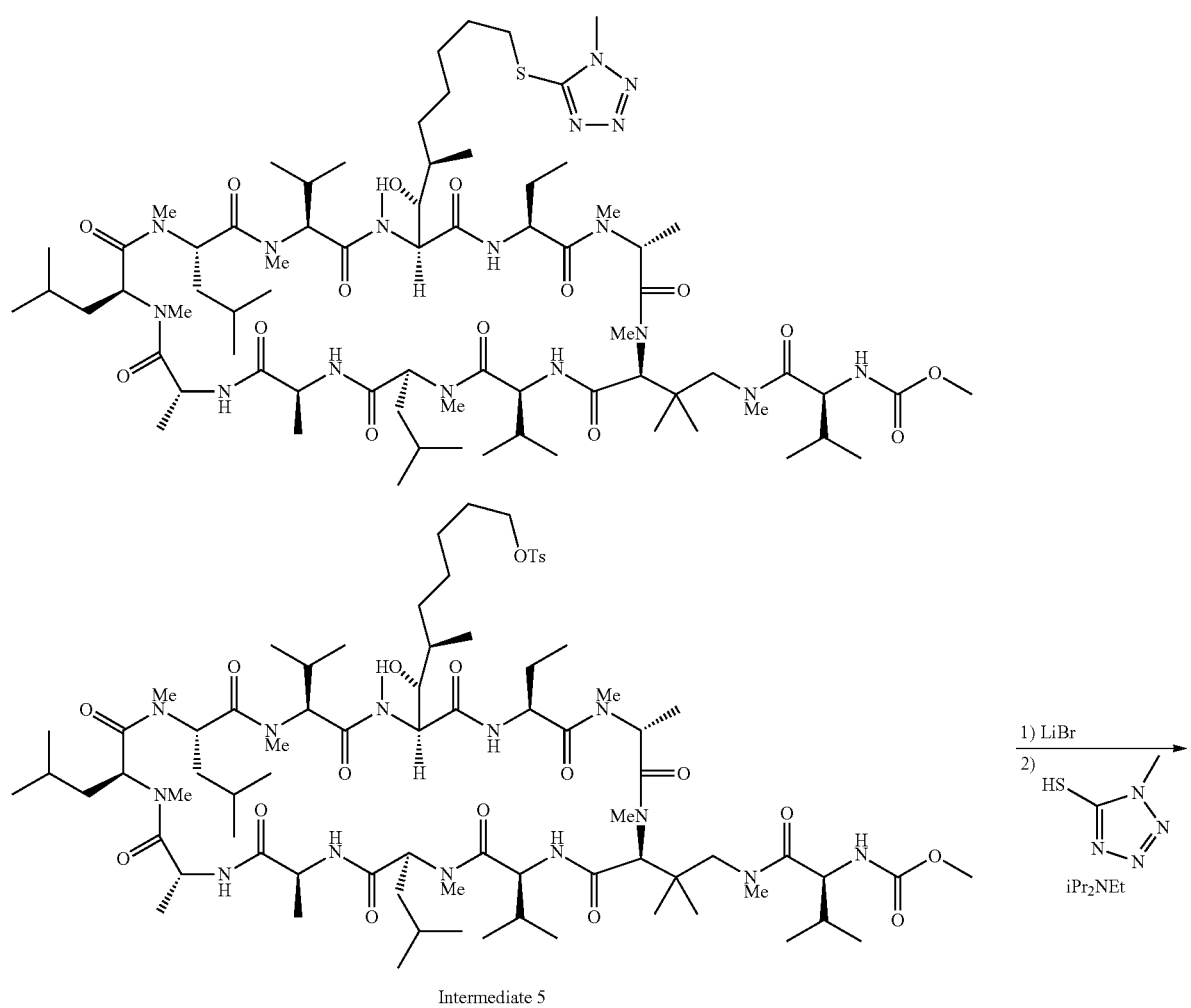
Intermediate 5
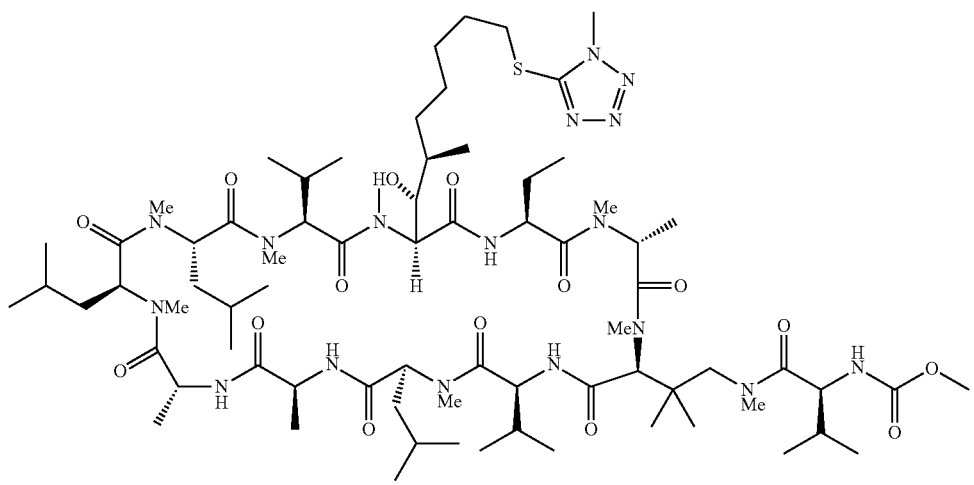
Example 9

To a solution of crude intermediate 5 (68 mg, 0.0428 mmol) in acetone (214 µL) was added LiBr (14.8 mg, 4 eq.), and stirred at 40° C. for 6.5 hrs. The reaction was diluted with MTBE, and washed with H$_2$O and brine, successively. The organic layer was dried over Na$_2$SO$_4$, filtered and evaporated to dryness. The crude bromide was used for the next step without purification.

To a mixture of crude bromide and 5-mercapto-1-methyltetrazole (19.8 mg, 4 eq.) in dry dioxane (214 µL) was added DIPEA (37.2 µL, 5 eq.), and stirred at 40° C. for 5 hrs. The reaction was diluted with MTBE, and washed with saturated aqueous NaHCO$_3$ solution and brine, successively. The organic layer was dried over Na$_2$SO$_4$, filtered and evaporated to dryness. The residue was purified by preparative HPLC (HPLC condition: mobile phase A-20 mM NH$_4$HCO$_3$ in H$_2$O (HPLC grade); mobile phase B: Acetonitrile (HPLC grade); Luna column (pre-heated at 55° C.), flow rate: 20 mL/min; 55-90% B for 30 min.) to give the pure example 9 (39.4 mg) as a white cotton after lyophilization. MS: (ESI) m/z 1533.34 (M+H)$^+$, 1555.37 (M+Na)$^+$.

Example 10

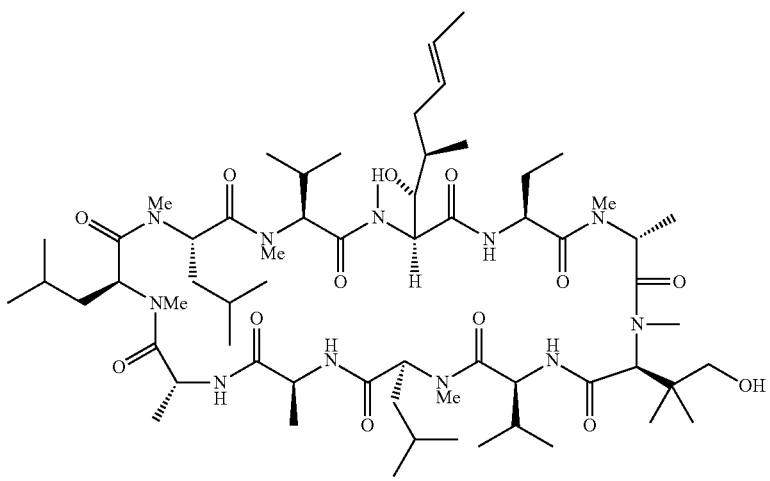

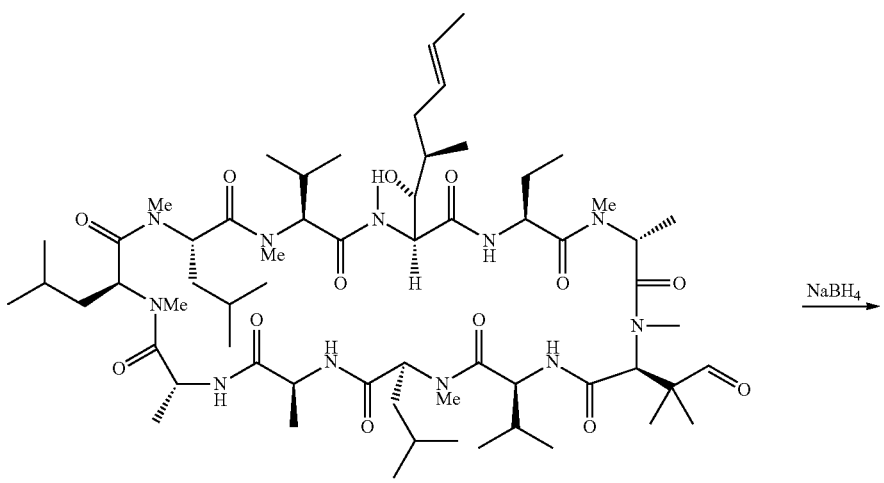

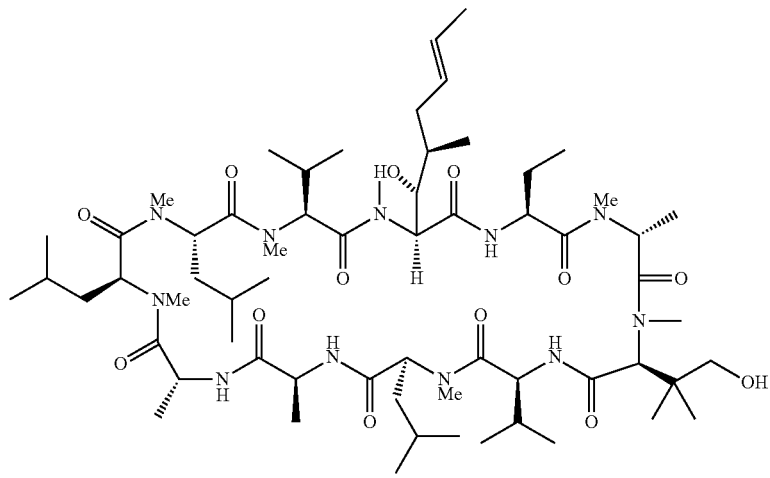

Example 10

To a mixture of 11 (3.23 mmol) in ⁱBuOH-MeOH (4:1, 30 mL) was added sodium borohydride (183 mg, 4.845 mmol) at 0° C. and stirred at room temperature for 1.5 hr, additional 0.5 eq. of sodium borohydride was added to the reaction and stirred for 40 min. The reaction was cooled to 0° C., quenched by addition of saturated NH$_4$Cl solution (20 mL), diluted with ethyl acetate (100 mL) and separated. The organic layer was stirred with 10% aqueous trisamine (30 mL) for 30 min, washed with H$_2$O and brine, separated, dried over Na$_2$SO$_4$, filtered and concentrated to dryness. The residue was purified by SiO$_2$ column chromatography with 0~45% methanol in CH$_2$Cl$_2$ to provide the title example 10 (2.217 g) as a white foam. MS: (ESI) m/z 1232.86 (M+H)$^+$, 1254.84 (M+Na)$^+$.

Example 11 and Example 12

Example 11

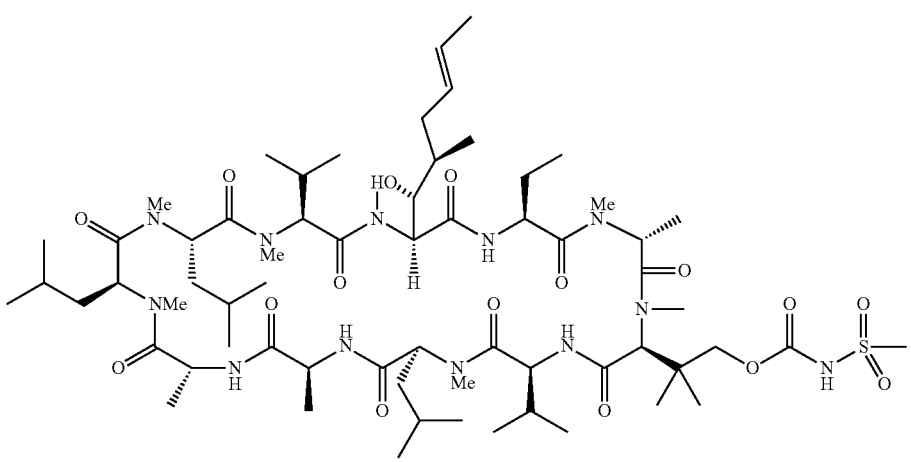

Example 12
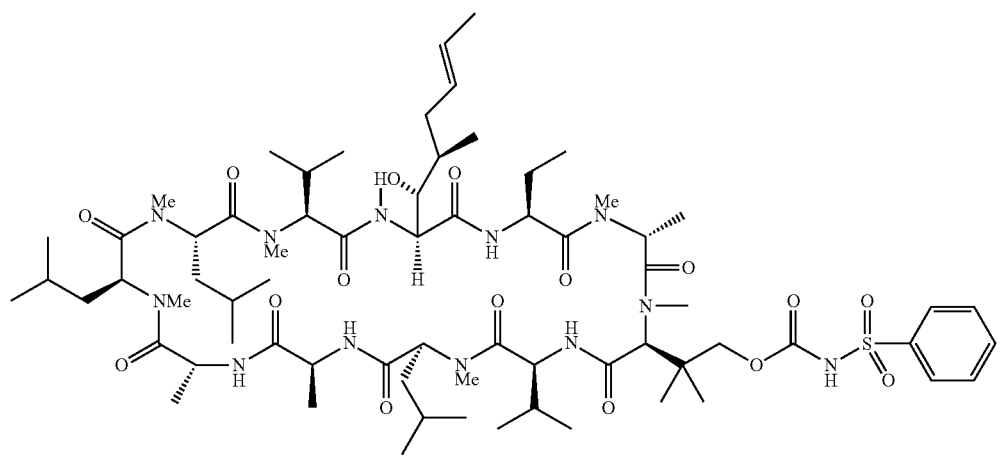
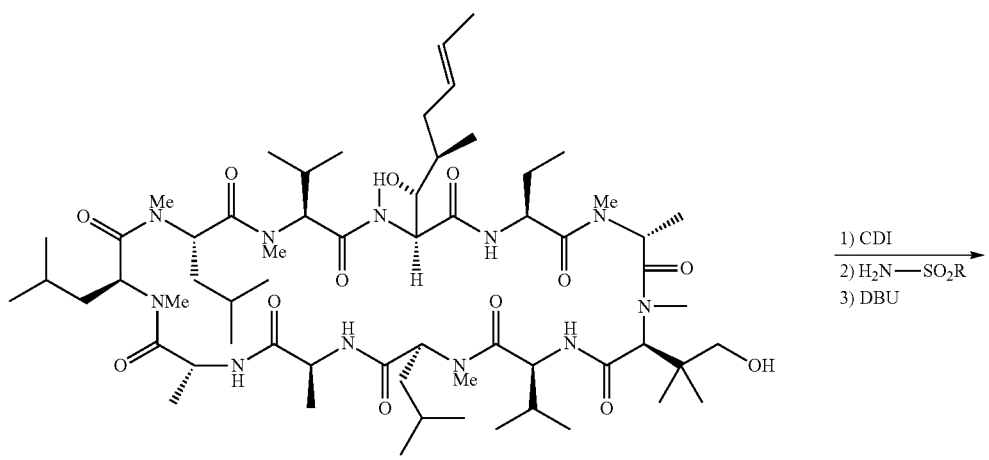
Example 10
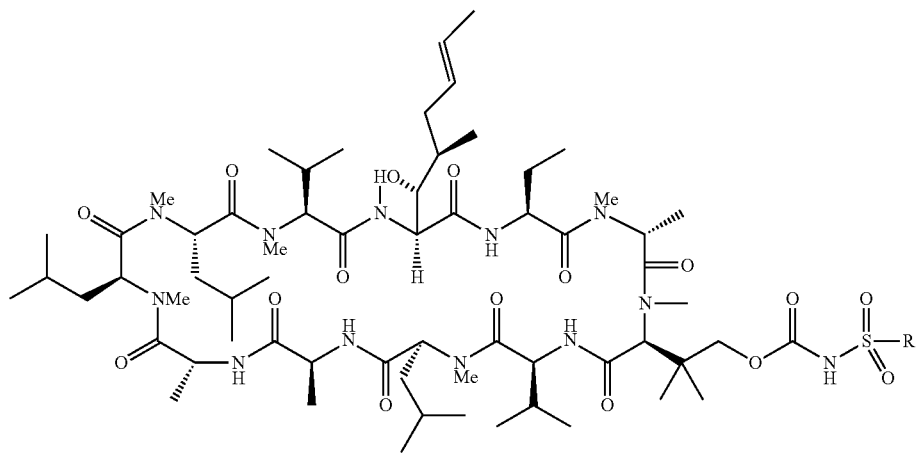
Example 11 (R = Me)
Example 12 (R = Ph)

To a mixture of example 10 (46.4 mg, 0.0376 mmol) in dry acetonitrile (0.4 mL) was added CDI (9.2 mg, 0.0564 mmol) at room temperature and stirred for 40 min. Then, additional 0.5 eq. of CDI was added to the reaction and heated at 60° C. for 50 min. After the reaction was completed, the reaction mixture was divided into 2 portions and concentrated to give the intermediate.

Example 11: One portion of intermediate was dissolved in dry DMF (0.4 mL), treated with methanesulfonamide (8.9 mg) and DBU (5 μL) and heated at 80° C. for 2 hrs. The reaction was diluted with ethylacetate, washed with $H_2O$ (×3) and brine and separated. The organic layer was dried over $Na_2SO_4$, filtered and concentrated to dryness. The residue was purified by preparative HPLC [HPLC condition: mobile phase A-20 mM $NH_4HCO_3$ in $H_2O$ (HPLC grade); mobile phase B: Acetonitrile (HPLC grade); semi-prep L-column (pre-heated at 50° C.), flow rate: 5 mL/min; 40-90% B for 30 min.] to give the title compound (11.5 mg) as a white cotton after lyophilization. MS: (ESI) m/z 1353.80 $(M+H)^+$, 1375.77 $(M+Na)^+$.

Example 12: The title Example 12 (5.1 mg) was prepared according the procedure described in the synthesis of Example 11 from the other portion of intermediate and benzenesulfonamide (14.7 mg). MS: (ESI) m/z 1415.75 $(M+H)^+$, 1437.79 $(M+Na)^+$.

Example 13 and Example 14

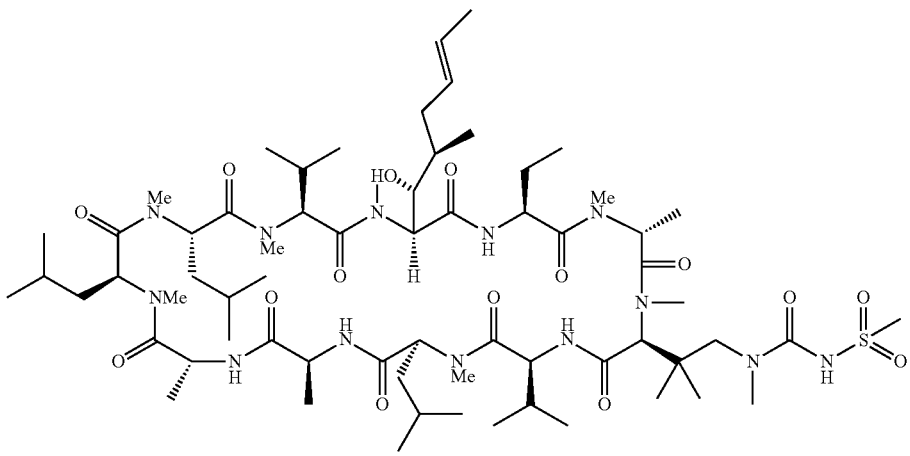

Example 13

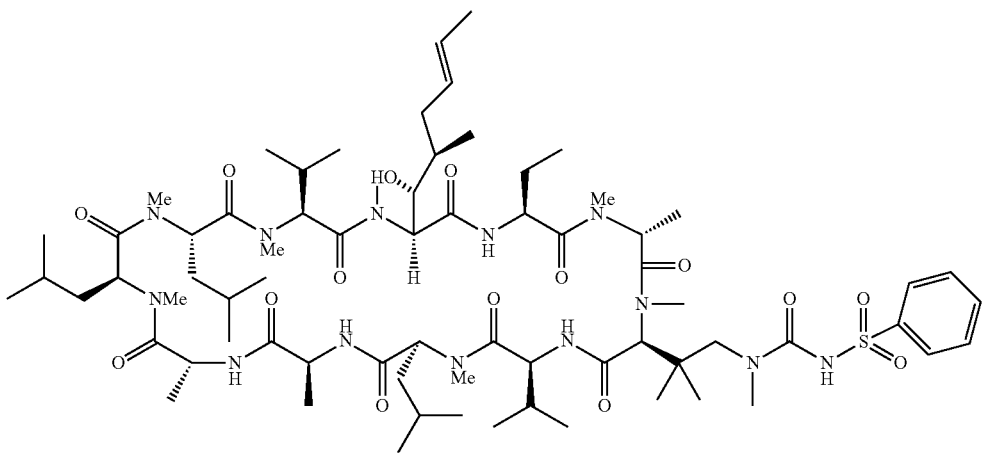

Example 14

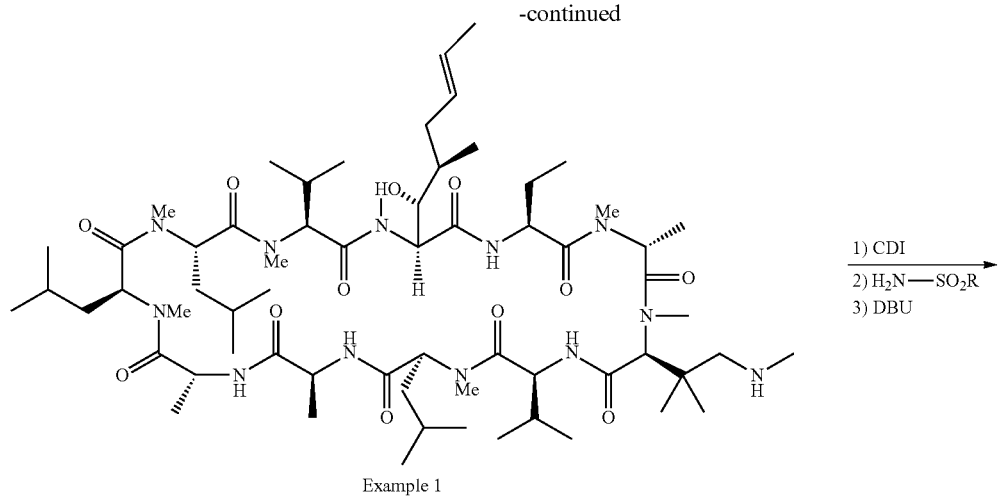

Example 1

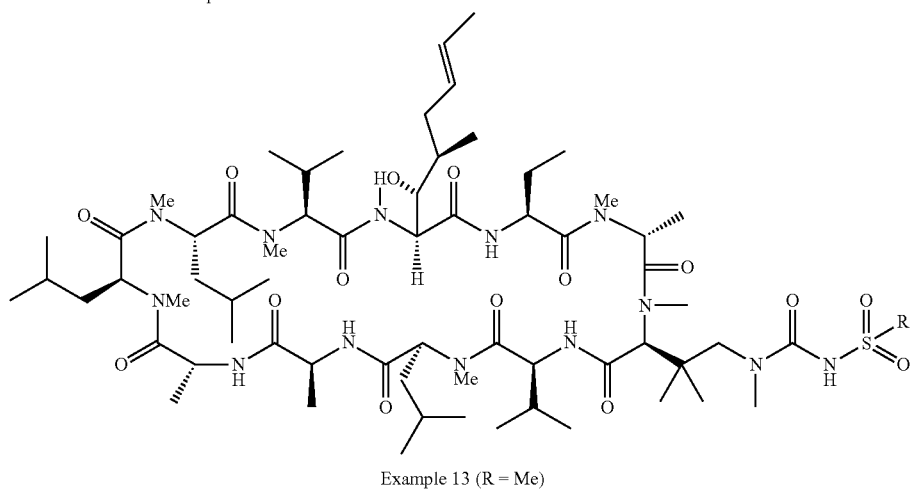

Example 13 (R = Me)
Example 14 (R = Ph)

To a mixture of example 1 (41.8 mg, 0.0335 mmol) in dry acetonitrile (0.4 mL) was added CDI (8.2 mg, 0.0503 mmol) at room temperature and stirred for 40 min. Then, additional 3 eq. of CDI was added to the reaction and heated at 60° C. for 2.5 hrs. After the reaction was completed, the reaction mixture was divided into 2 portions and concentrated to give the intermediate.

Example 13: One portion of intermediate was dissolved in dry DMF (0.4 mL), treated with methanesulfonamide (8 mg) and DBU (5 µL) and heated at 80° C. for 24 hrs. The reaction was diluted with ethylacetate, washed with $H_2O$ (×3) and brine and separated. The organic layer was dried over $Na_2SO_4$, filtered and concentrated to dryness. The residue was purified by preparative HPLC [HPLC condition: mobile phase A-20 mM $NH_4HCO_3$ in $H_2O$ (HPLC grade); mobile phase B: Acetonitrile (HPLC grade); semi-prep L-column (pre-heated at 50° C.), flow rate: 5 mL/min; 40-95% B for 30 min.] to give the title compound (4.8 mg) as a white cotton after lyophilization. MS: (ESI) m/z 1366.88 $(M+H)^+$, 1388.86 $(M+Na)^+$.

Example 14: The title Example 14 (3 mg) was prepared according the procedure described in the synthesis of Example 13 from the other portion of intermediate and benzenesulfonamide (13.2 mg). MS: (ESI) m/z 1428.91 $(M+H)^+$, 1450.88 $(M+Na)^+$.

BIOLOGICAL ACTIVITY

1. HCV Replicon Cell Lines

HCV replicon cell lines (kindly provided by R. Bartenschlager) isolated from colonies as described by Lohman et al. (Lohman et al. (1999) Science 285: 110-113, expressly incorporated by reference in its entirety) and used for all experiments. The HCV replicon has the nucleic acid sequence set forth in EMBL Accession No.: AJ242651, the coding sequence of which is from nucleotides 1801 to 8406.

The coding sequence of the published HCV replicon was synthesized and subsequently assembled in a modified plasmid pBR322 (Promega, Madison, Wis.) using standard molecular biology techniques. One replicon cell line ("SGR 11-7") stably expresses HCV replicon RNA which consists of (i) the HCV 5'UTR fused to the first 12 amino acids of the capsid protein, (ii) the neomycin phosphotransferase gene (neo), and (iii) the IRES from encephalomyocarditis virus (EMCV) and (iv) HCV NS2 to NS5B genes and the HCV 3'UTR. Another replicon cell line ("Huh-luc/neo-ET") described by Vrolijk et. al. (Vrolijk et. al. (2003) Journal of Virological Methods 110:201-209, expressly incorporated by reference in its entirety) stably expresses HCV replicon RNA which consists of (i) the HCV 5'UTR fused to the first 12 amino acids of the capsid protein, (ii) the firefly luciferase reporter gene, (iii) the ubiquitin gene, (iv) the neomycin phosphotransferase gene (neo), and (v) the IRES from encephalomyocarditis virus (EMCV) and (vi) HCV NS3 to NS5B genes that harbor cell culture adaptive mutations (E1202G, T12801, K1846T) and the HCV 3'UTR.

These cell lines are maintained at 37° C., 5% $CO_2$, 100% relative humidity in DMEM (Cat #11965-084, Invitrogen), with 10% fetal calf serum ("FCS", Invitrogen), 1% non-essential amino acids (Invitrogen), 1% of Glutamax (Invitrogen), 1% of 100× penicillin/streptomycin (Cat #15140-122, Invitrogen) and Geneticin (Cat #10131-027, Invitrogen) at 0.75 mg/ml or 0.5 mg/ml for 11-7 and Huh-luc/neo-ET cells, respectively.

2. HCV Replicon Assay—qRT-PCR $EC_{50}$ values of single agent compounds were determined by HCV RNA detection using quantitative RT-PCR, according to the manufacturer's instructions, with a TAQMAN® One-Step RT-PCR Master Mix Reagents Kit (Cat #AB 4309169, Applied Biosystems) on an ABI Model 7500 thermocycler. $EC_{50}$ values of combinations are similarly determined by HCV RNA detection using quantitative RT-PCR. The TAQMAN primers to use for detecting and quantifying HCV RNA obtained from Integrated DNA Technologies. HCV RNA is normalized to GAPDH RNA levels in drug-treated cells, which is detected and quantified using the Human GAPDH Endogenous Control Mix (Applied Biosystems, AB 4310884E). Total cellular RNA is purified from 96-well plates using the RNAqueous 96 kit (Ambion, Cat #AM1812). Chemical agent cytotoxicity is evaluated using an MTS assay according to the manufacturer's directions (Promega).

3. HCV Replicon Assay—Luciferase

Since clinical drug resistance often develops in viral infections following single agent therapies, there is a need to assess the additive, antagonistic, or synergistic properties of combination therapies. We use the HCV replicon system to assess the potential use of the compound of the present invention or in combination therapies with Interferon alpha, cyclosporine analogs and inhibitors targeting other HCV proteins. The acute effects of a single or combinations of drugs are studied in the "Huh-luc/neo-ET" replicon with each chemical agent titrated in an X or Y direction in a 6 point two-fold dilution curve centered around the EC50 of each drug. Briefly, replicon cells are seeded at 7,000 cells per well in 90 ul DMEM (without phenol red, Invitrogen Cat. #31053-036) per well with 10% FCS, 1% non-essential amino acids, 1% of Glutamax and 1% of 100× penicillin/streptomycin and incubated overnight at 37° C., 5% $CO_2$, 100% relative humidity. 16-20 h after seeding cells, test compounds previously solubilized and titrated in dimethyl sulfoxide ("DMSO") from each X plate and Y plate are diluted 1:100 in DMEM (without phenol red, Invitrogen Cat. #31053-036) with 10% FCS, 1% non-essential amino acids, 1% of Glutamax and 1% of 100× penicillin/streptomycin and added directly to the 96-well plate containing cells and growth medium at a 1:10 dilution for a final dilution of compound and DMSO of 1:1000 (0.2% DMSO final concentration). Drug treated cells are incubated at 37° C., 5% $CO_2$, 100% relative humidity for 72 hours before performing a luciferase assay using 100 ul per well BriteLite Plus (Perkin Elmer) according to the manufacturer's instructions. Data analysis utilizes the method published by Prichard and Shipman (Antiviral Research, 1990. 14:181-205). Using this method, the combination data are analyzed for antagonistic, additive, or synergistic combination effects across the entire combination surface created by the diluted compounds in combination.

The compounds of the present invention can be effective against the HCV 1a genotype. It should also be understood that the compounds of the present invention can inhibit multiple genotypes of HCV. In one embodiment, compounds of the present invention are active against the 1a, 1b, 2a, 2b, 3a, 4a, and 5a genotypes. Table 1 shows the $EC_{50}$ values of representative compounds of the present invention against the HCV 1a genotype from the above described Luciferase assay. $EC_{50}$ ranges against HCV 1a are as follows: A>1 µM; B 0.1-1 µM; C 0.01~0.1 µM; D<0.01 µM.

TABLE 1

| Genotype-1a Replicon $EC_{50}$ | |
|---|---|
| Example | $EC_{50}$ 1a |
| 1 | C |
| 2 | C |
| 3 | C |
| 4 | C |
| 5 | C |
| 6 | C |
| 7 | C |
| 8 | C |
| 9 | C |
| 11 | A |
| 12 | B |
| 13 | B |
| 14 | B |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by the formula (I):

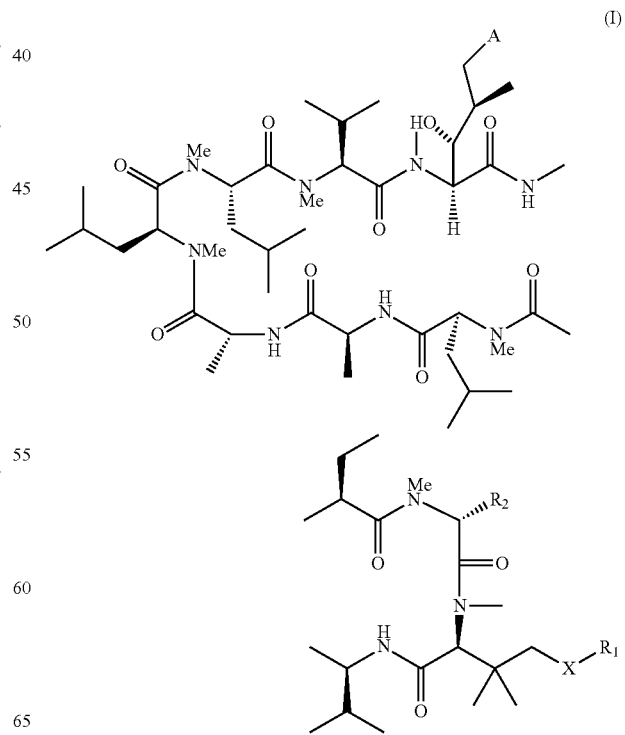

or a pharmaceutically acceptable salt thereof, wherein:

$R_1$ and A are each independently selected from:
a) $R_{11}$, where $R_{11}$ is selected from:
  1) Hydrogen;
  2) Deuterium;
  3) $C_1$-$C_8$ alkyl;
  4) Substituted $C_1$-$C_8$ alkyl;
  5) $C_2$-$C_8$ alkenyl;
  6) Substituted $C_2$-$C_8$ alkenyl;
  7) $C_2$-$C_8$ alkynyl;
  8) Substituted $C_2$-$C_8$ alkynyl;
  9) $C_3$-$C_{12}$ cycloalkyl;
  10) Substituted $C_3$-$C_{12}$ cycloalkyl;
  11) Aryl;
  12) Substituted aryl;
  13) Heterocycloalkyl;
  14) Substituted heterocycloalkyl;
  15) Heteroaryl; and
  16) Substituted heteroaryl;
b) —C(O)O$R_{11}$, where $R_{11}$ is as previously defined;
c) —C(O)$R_{11}$, where $R_{11}$ is as previously defined;
d) —C(O)OCH$_2$-T-$R_{12}$, where T is —O— or —S— and $R_{12}$ is selected from:
  1) $C_1$-$C_8$ alkyl;
  2) Substituted $C_1$-$C_8$ alkyl;
  3) $C_2$-$C_8$ alkenyl;
  4) Substituted $C_2$-$C_8$ alkenyl;
  5) $C_2$-$C_8$ alkynyl;
  6) Substituted $C_2$-$C_8$ alkynyl;
  7) $C_3$-$C_{12}$ cycloalkyl;
  8) Substituted $C_3$-$C_{12}$ cycloalkyl;
  9) Aryl;
  10) Substituted aryl;
  11) Heterocycloalkyl;
  12) Substituted heterocycloalkyl;
  13) Heteroaryl; or
  14) Substituted heteroaryl;
e) —C(O)N($R_{13}$)($R_{14}$), where $R_{13}$ and $R_{14}$ are independently selected from $R_{11}$ and $R_{11}$ is as previously defined or $R_{13}$ and $R_{14}$, together with the nitrogen atom to which they are attached, form a substituted or unsubstituted heterocycloalkyl;
f) —C(O)S$R_{11}$, where $R_{11}$ is as previously defined;
g) —C(S)O$R_{11}$, where $R_{11}$ is as previously defined;
h) —C(O)OCH$_2$OC(O)$R_{12}$, where $R_{12}$ is as previously defined; and
i) —C(S)S$R_{11}$, where $R_{11}$ is as previously defined;

$R_2$, is selected from: hydrogen or methyl;

X is selected from the group consisting of: O, S(O)$_m$, wherein m=0, 1, or 2, and —N($R_{12}$)—, wherein $R_{12}$ is $R_{11}$, and $R_{11}$ is as previously defined, or $R_{12}$ and $R_1$ are combined together with the nitrogen atom to which they are attached to form a substituted or unsubstituted heterocycloalkyl.

2. A compound according to claim 1, which is represented by the formula (II):

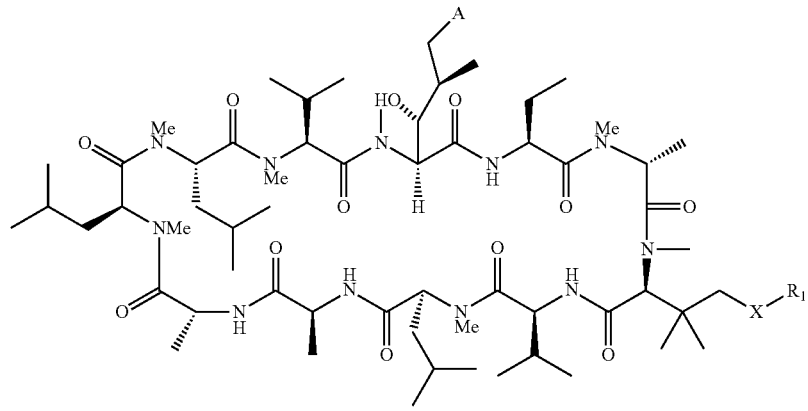

(II)

or a pharmaceutically acceptable salt thereof, wherein $R_1$, X and A are as defined in claim 1.

3. A compound according to claim 1, which is represented by the formula (III):

(III)

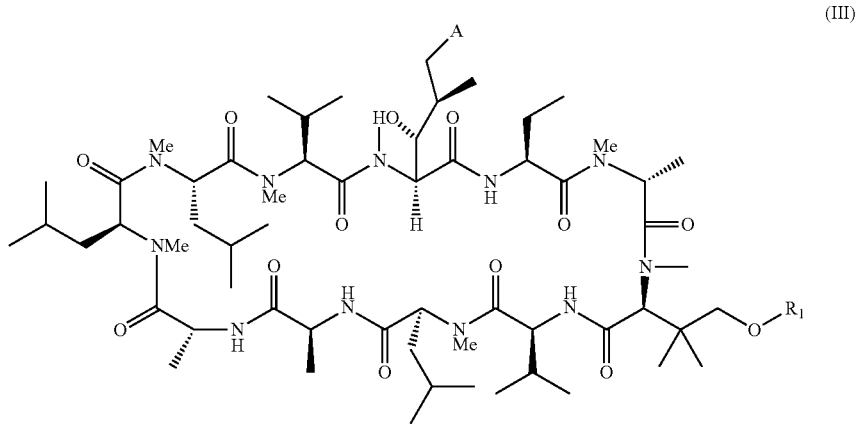

or a pharmaceutically acceptable salt thereof, wherein $R_1$ and A are as defined in claim 1.

4. A compound according to claim 1, which is represented by the Formula (IV):

(IV)

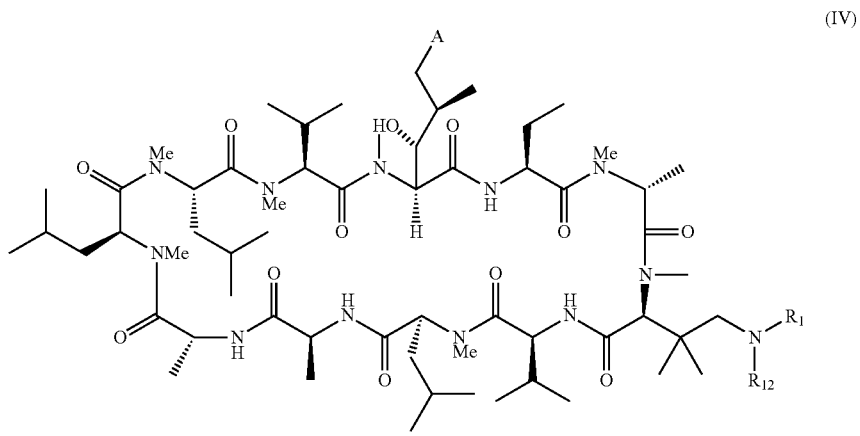

or a pharmaceutically acceptable salt thereof, wherein $R_1$, $R_{12}$ and A are as defined in claim 1.

5. A compound according to claim 1, wherein A is selected from the groups listed below, or a pharmaceutically acceptable salt thereof:

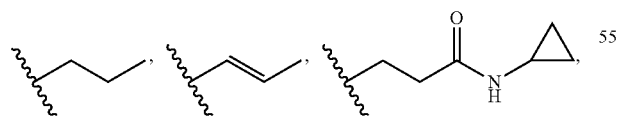

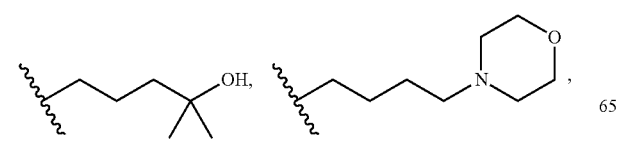

-continued

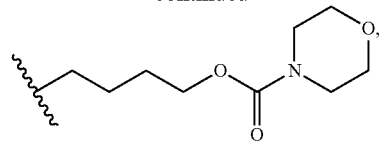

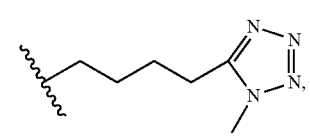

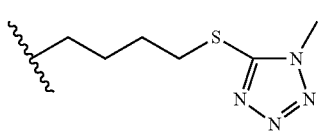

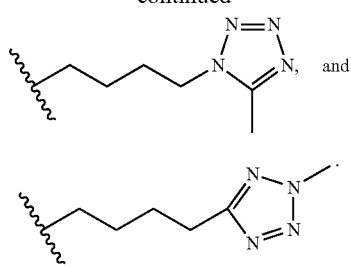

6. A compound according to claim 1, wherein X—R₁ is selected from the groups listed below, or a pharmaceutically acceptable salt thereof:

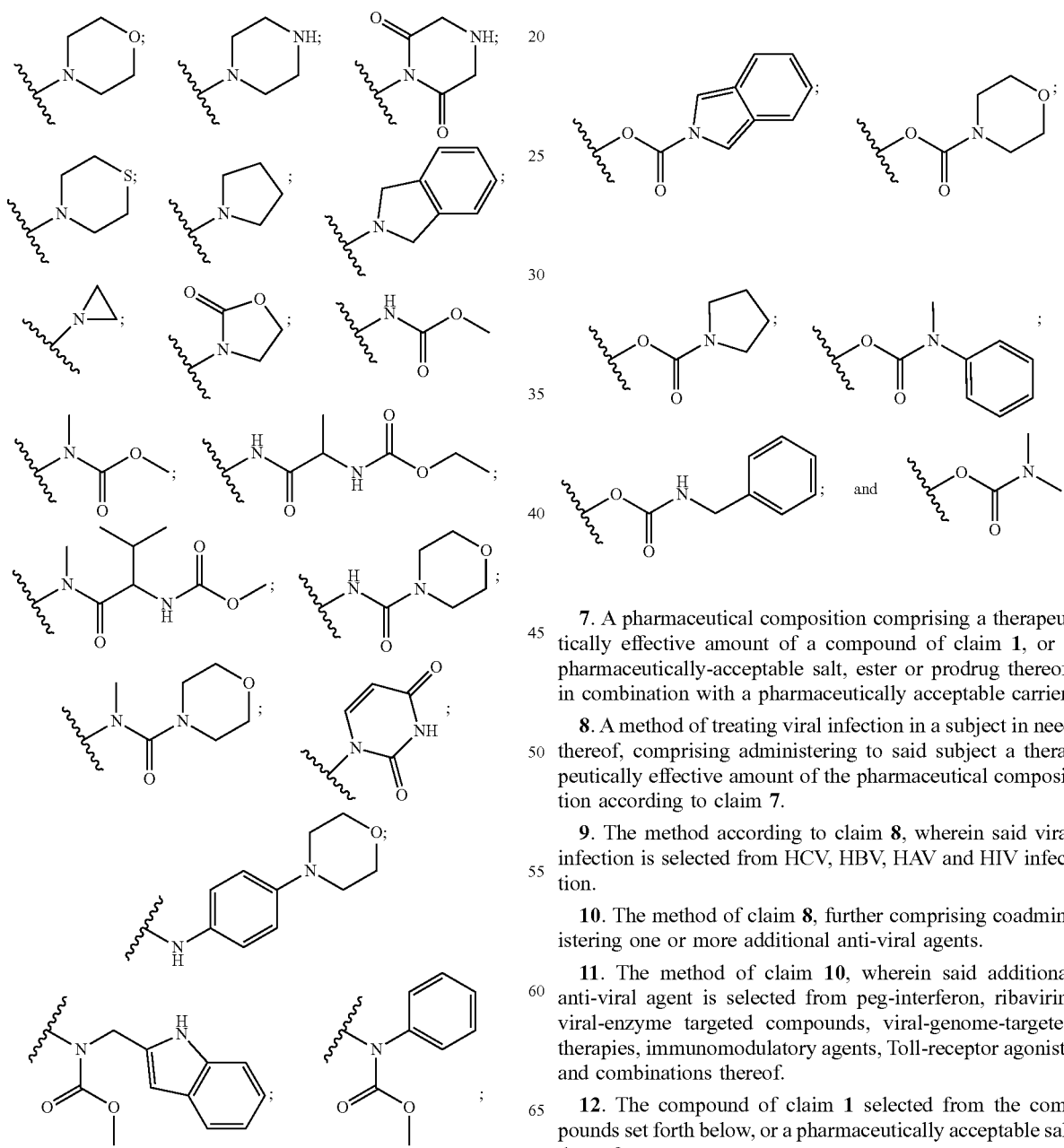

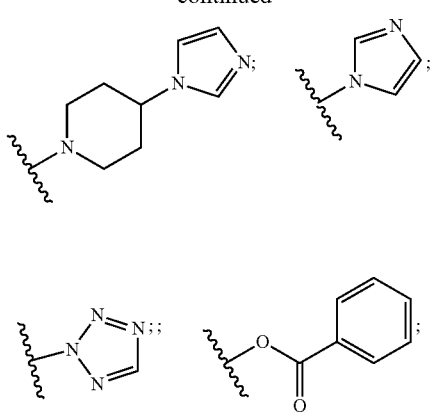

7. A pharmaceutical composition comprising a therapeutically effective amount of a compound of claim 1, or a pharmaceutically-acceptable salt, ester or prodrug thereof, in combination with a pharmaceutically acceptable carrier.

8. A method of treating viral infection in a subject in need thereof, comprising administering to said subject a therapeutically effective amount of the pharmaceutical composition according to claim 7.

9. The method according to claim 8, wherein said viral infection is selected from HCV, HBV, HAV and HIV infection.

10. The method of claim 8, further comprising coadministering one or more additional anti-viral agents.

11. The method of claim 10, wherein said additional anti-viral agent is selected from peg-interferon, ribavirin, viral-enzyme targeted compounds, viral-genome-targeted therapies, immunomodulatory agents, Toll-receptor agonists and combinations thereof.

12. The compound of claim 1 selected from the compounds set forth below, or a pharmaceutically acceptable salt thereof:

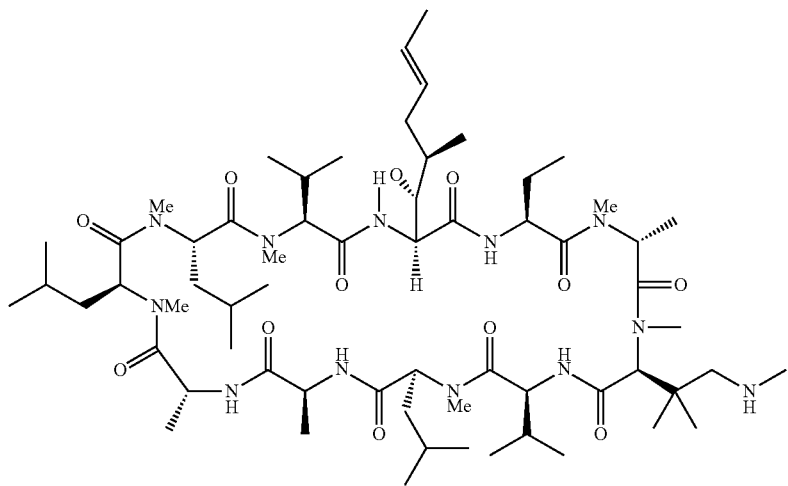
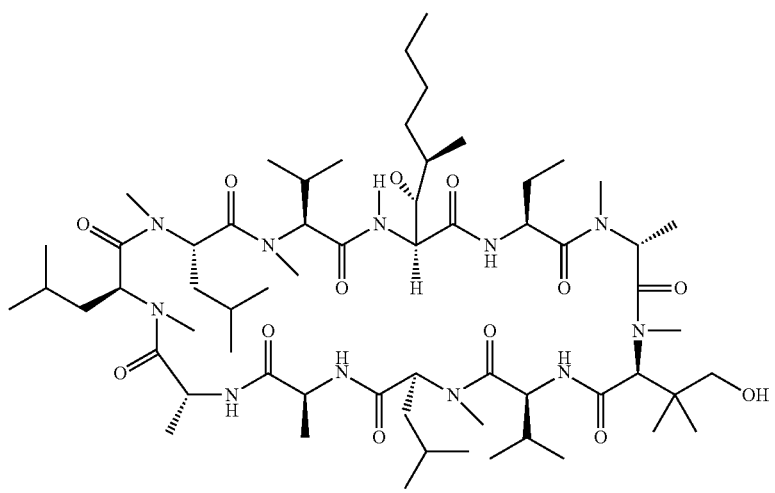
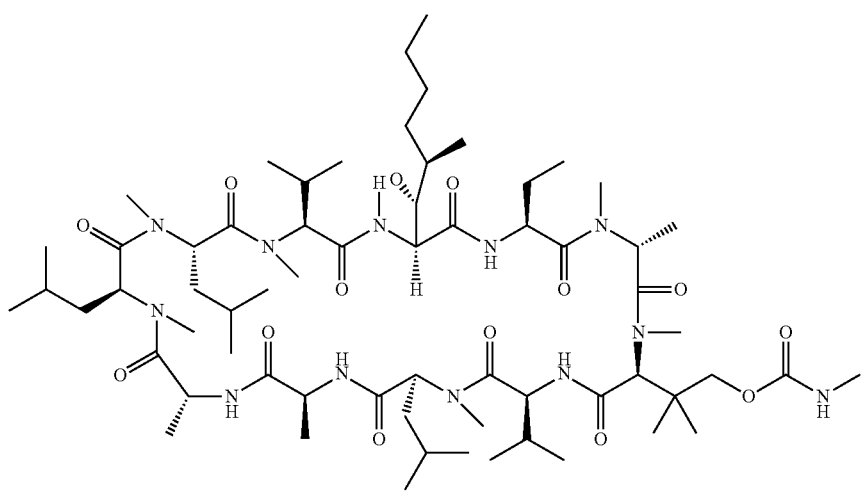

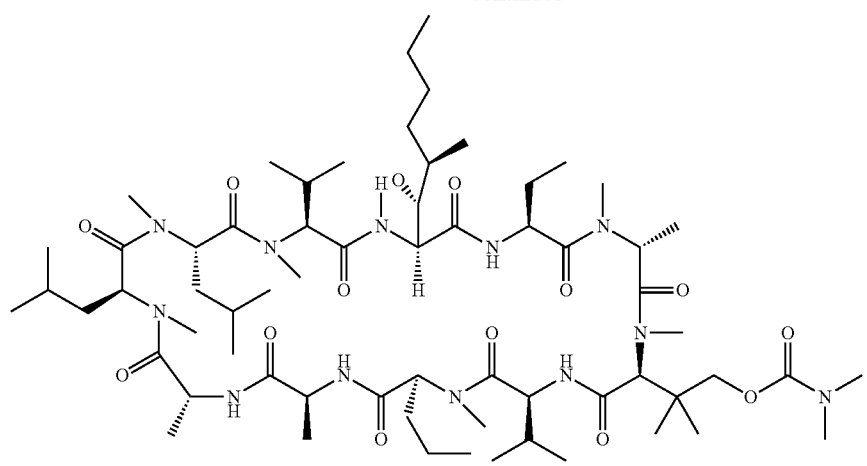
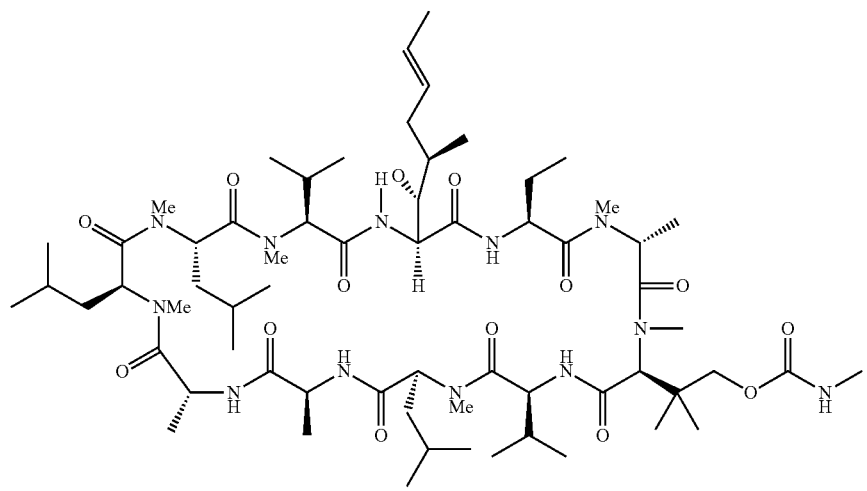
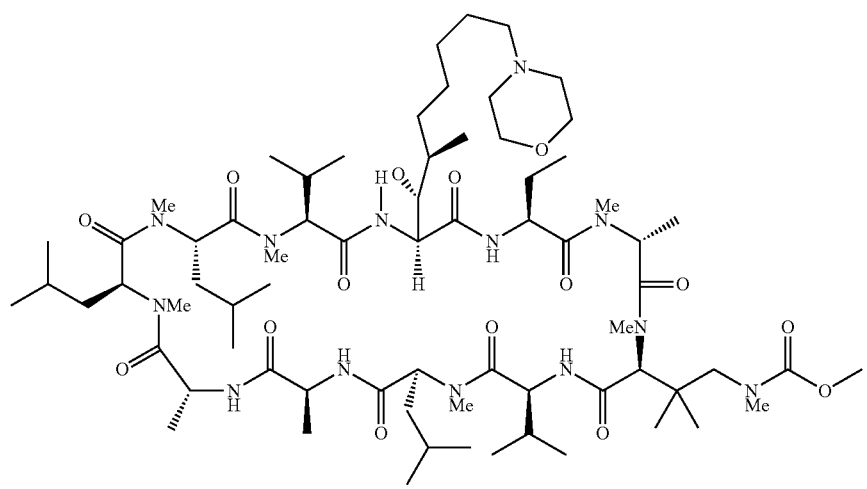

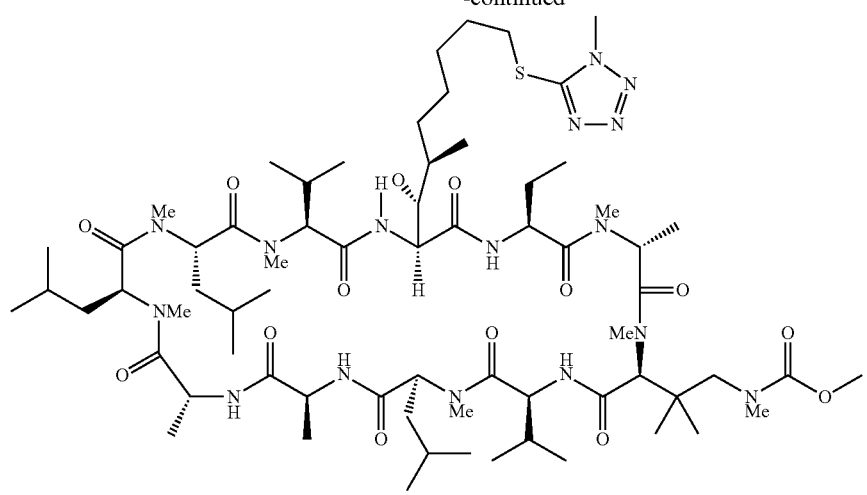
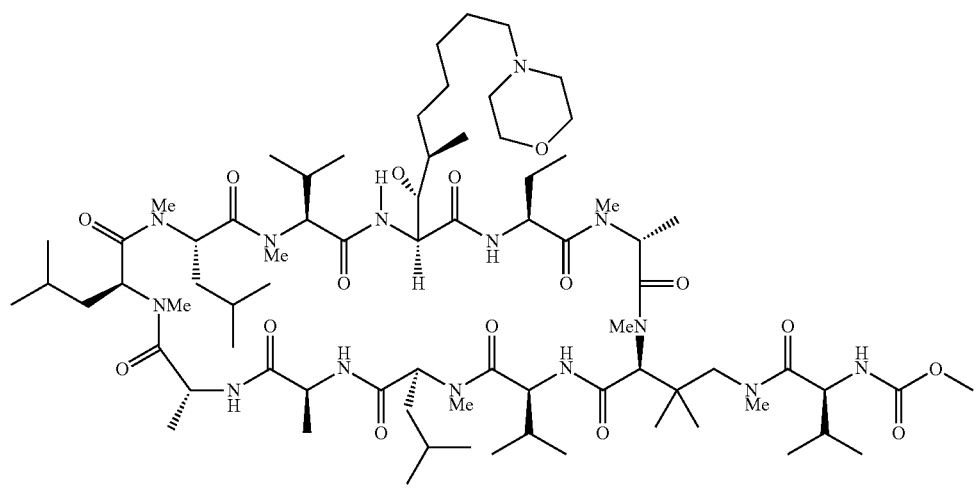
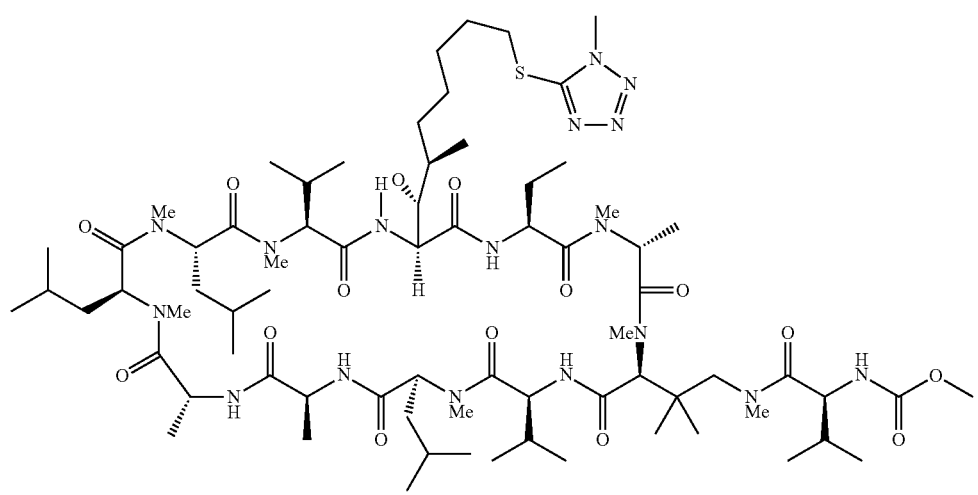

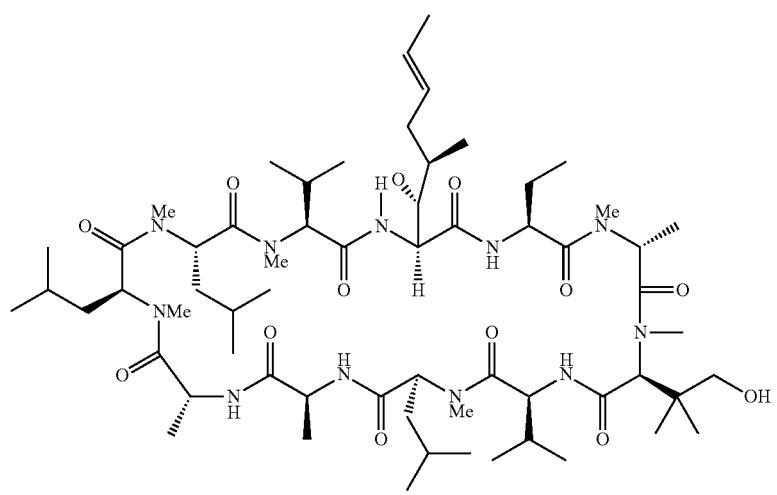
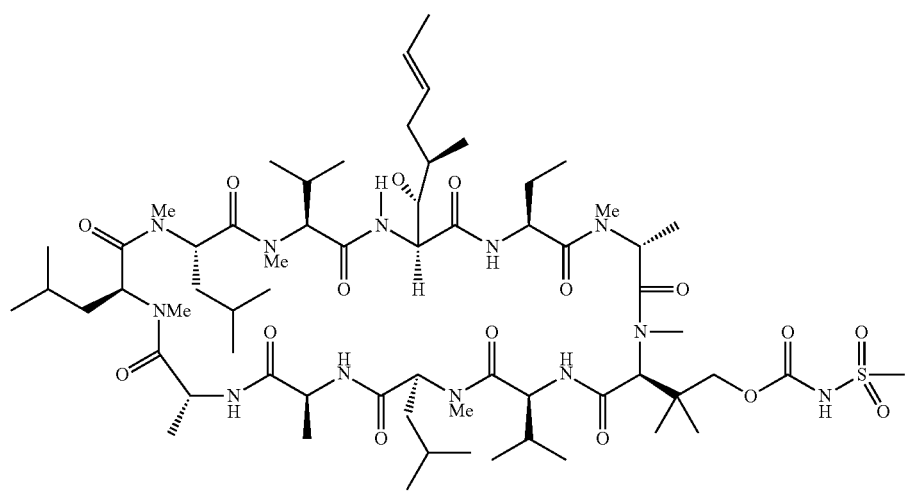
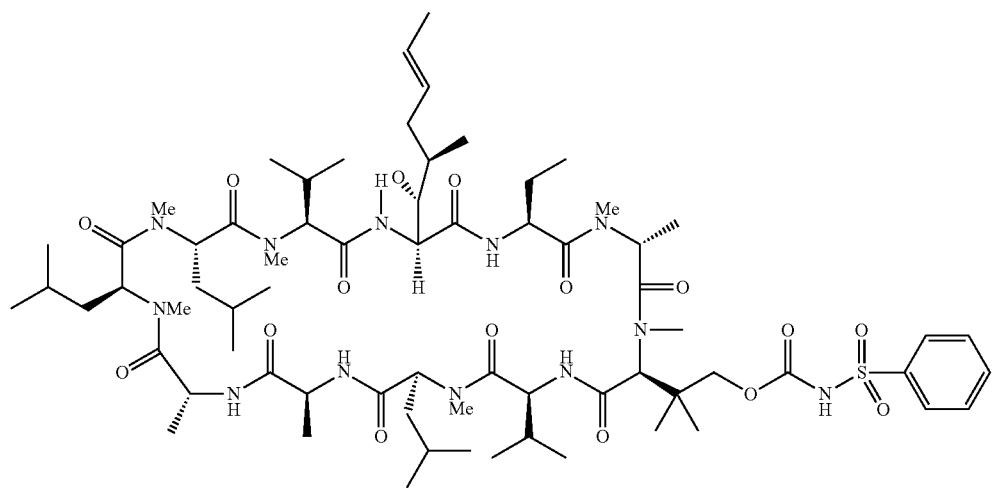

-continued
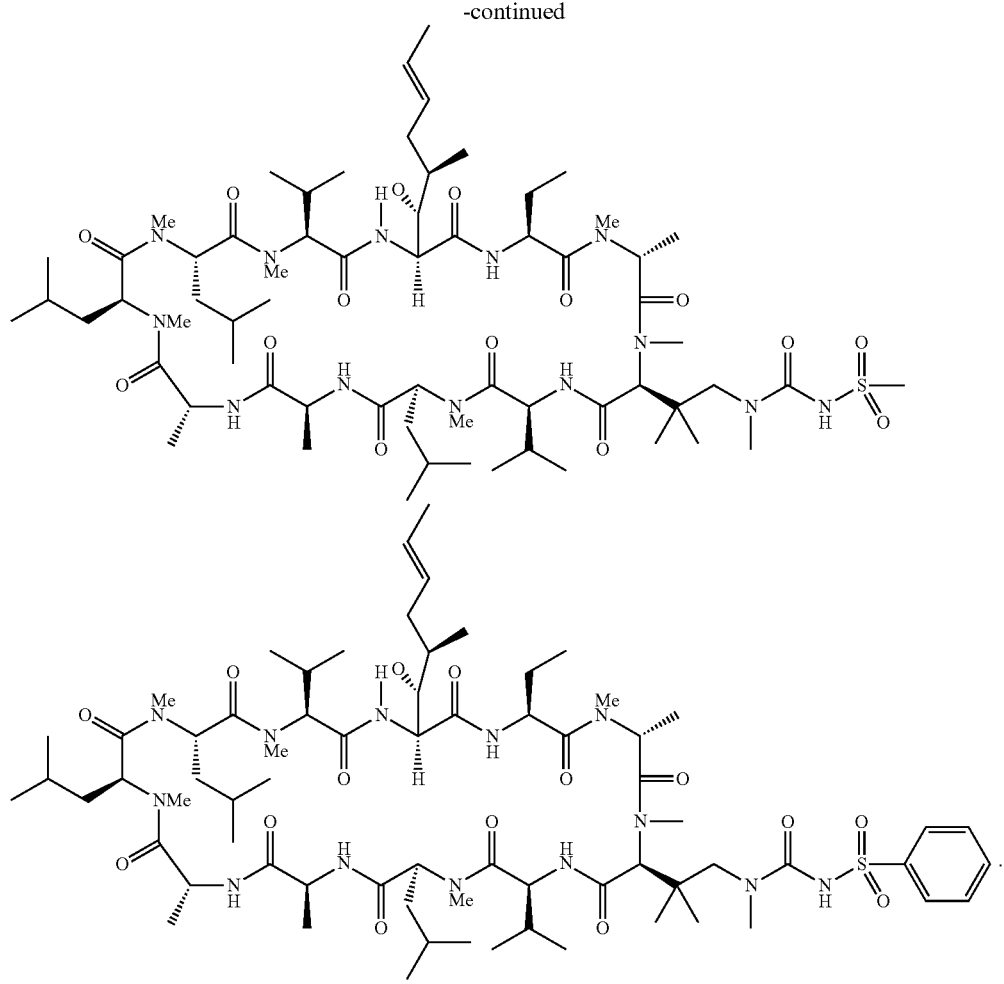
* * * * *